United States Patent
Duer et al.

(10) Patent No.: US 9,976,192 B2
(45) Date of Patent: May 22, 2018

(54) WAVEGUIDE-BASED DETECTION SYSTEM WITH SCANNING LIGHT SOURCE

(71) Applicant: LDIP, LLC, Thousand Oaks, CA (US)

(72) Inventors: Reuven Duer, Thousand Oaks, CA (US); Yun-Pei Chang, Arcadia, CA (US); Ashutosh Shastry, Santa Clara, CA (US)

(73) Assignee: LDIP, LLC, Thousand Oaks, CA (US)

( * ) Notice: Subject to any disclaimer, the term of this patent is extended or adjusted under 35 U.S.C. 154(b) by 0 days. days.

(21) Appl. No.: 15/284,396

(22) Filed: Oct. 3, 2016

(65) Prior Publication Data

US 2017/0023477 A1 Jan. 26, 2017

Related U.S. Application Data

(63) Continuation-in-part of application No. 15/245,062, filed on Aug. 23, 2016, which is a continuation of
(Continued)

(51) Int. Cl.
*G01N 21/00* (2006.01)
*C12Q 1/70* (2006.01)
(Continued)

(52) U.S. Cl.
CPC ........ *C12Q 1/703* (2013.01); *B01L 3/502715* (2013.01); *C12Q 1/6825* (2013.01);
(Continued)

(58) Field of Classification Search
CPC .......... G02B 6/4226; G02B 6/00; G02B 6/26; G01N 21/00; H01J 3/14
(Continued)

(56) References Cited

U.S. PATENT DOCUMENTS

| 4,394,060 A | 7/1983 | Verber et al. |
| 4,444,879 A | 4/1984 | Foster et al. |

(Continued)

FOREIGN PATENT DOCUMENTS

| EP | 598213 B1 | 7/1997 |
| EP | 737308 B1 | 3/1998 |

(Continued)

OTHER PUBLICATIONS

Andrew.Cmu.Edu; Evanescent Waves; printed from http://andrew.cmu.edu/user/dcprieve/Evanescent%20waves.htm on Aug. 22, 2012; 2 pages.

(Continued)

*Primary Examiner* — Isiaka Akanbi
(74) *Attorney, Agent, or Firm* — Shay Glenn LLP

(57) ABSTRACT

The invention provides methods and devices for generating optical pulses in one or more waveguides using a spatially scanning light source. A detection system, methods of use thereof and kits for detecting a biologically active analyte molecule are also provided. The system includes a scanning light source, a substrate comprising a plurality of waveguides and a plurality of optical sensing sites in optical communication with one or more waveguide of the substrate, a detector that is coupled to and in optical communication with the substrate, and means for spatially translating a light beam emitted from said scanning light source such that the light beam is coupled to and in optical communication with the waveguides of the substrate at some point along its scanning path. The use of a scanning light source allows the coupling of light into the waveguides of the substrate in a simple and cost-effective manner.

7 Claims, 55 Drawing Sheets

Related U.S. Application Data application No. 14/194,437, filed on Feb. 28, 2014, now Pat. No. 9,423,397, which is a continuation-in-part of application No. 12/769,364, filed on Apr. 28, 2010, now Pat. No. 8,675,199, which is a continuation-in-part of application No. 11/683,808, filed on Mar. 8, 2007, now Pat. No. 7,951,583, and a continuation-in-part of application No. 12/209,295, filed on Sep. 12, 2008, now Pat. No. 8,288,157.

(60) Provisional application No. 61/173,771, filed on Apr. 29, 2009, provisional application No. 61/223,550, filed on Jul. 7, 2009, provisional application No. 60/743,458, filed on Mar. 10, 2006, provisional application No. 60/971,878, filed on Sep. 12, 2007, provisional application No. 62/235,977, filed on Oct. 1, 2015.

(51) Int. Cl.
*G01N 21/64* (2006.01)
*C12Q 1/68* (2018.01)
*B01L 3/00* (2006.01)
*G02B 6/42* (2006.01)
*G01N 33/543* (2006.01)

(52) U.S. Cl.
CPC ... *G01N 21/6428* (2013.01); *G01N 33/54373* (2013.01); *G02B 6/4226* (2013.01); B01L 2300/0636 (2013.01); B01L 2300/0654 (2013.01); *G01N 21/6452* (2013.01); G01N 2021/6463 (2013.01); G01N 2201/0853 (2013.01); G01N 2201/10 (2013.01)

(58) Field of Classification Search
USPC .................................. 356/311, 432, 445–446
See application file for complete search history.

(56) References Cited

U.S. PATENT DOCUMENTS

| | | |
|---|---|---|
| 4,478,485 A | 10/1984 | Khoe et al. |
| 4,515,430 A | 5/1985 | Johnson |
| 4,651,343 A | 3/1987 | Laor |
| 4,744,623 A | 5/1988 | Prucnal et al. |
| 4,746,179 A | 5/1988 | Dahne et al. |
| 4,799,797 A | 1/1989 | Huggins |
| 4,815,843 A | 3/1989 | Tiefenthaler et al. |
| 4,820,016 A | 4/1989 | Cohen et al. |
| 4,838,631 A | 6/1989 | Chande et al. |
| 4,850,666 A | 7/1989 | Izutsu et al. |
| RE33,064 E * | 9/1989 | Carter ............. G01N 33/54373 356/414 |
| 4,876,446 A | 10/1989 | Kambe et al. |
| 4,881,789 A | 11/1989 | Levinson |
| 4,889,407 A | 12/1989 | Markle et al. |
| 4,906,837 A | 3/1990 | Doneen et al. |
| 4,940,328 A | 7/1990 | Hartman |
| 4,978,503 A | 12/1990 | Shanks et al. |
| 4,998,792 A | 3/1991 | Boerstler et al. |
| 5,031,987 A | 7/1991 | Norling |
| 5,075,494 A | 12/1991 | Gassen |
| 5,077,878 A | 1/1992 | Armiento et al. |
| 5,081,012 A | 1/1992 | Flanagan et al. |
| 5,120,131 A | 6/1992 | Lukosz |
| 5,121,457 A | 6/1992 | Foley et al. |
| 5,151,480 A | 9/1992 | Podszun et al. |
| 5,173,747 A | 12/1992 | Boiarski et al. |
| 5,208,111 A | 5/1993 | Decher et al. |
| 5,217,568 A | 6/1993 | Tessier et al. |
| 5,340,715 A * | 8/1994 | Slovacek ............. G01N 21/648 250/458.1 |
| 5,344,784 A | 9/1994 | Attridge |
| 5,377,008 A | 12/1994 | Ridgway et al. |
| 5,439,647 A | 8/1995 | Saini |
| 5,440,388 A | 8/1995 | Erickson |
| 5,444,805 A | 8/1995 | Mayer |
| 5,455,178 A | 10/1995 | Fattinger |
| 5,479,260 A | 12/1995 | Fattinger |
| 5,494,798 A | 2/1996 | Gerdt et al. |
| 5,496,701 A | 3/1996 | Pollard-Knight |
| 5,512,492 A | 4/1996 | Herron et al. |
| 5,547,839 A | 8/1996 | Dower et al. |
| 5,573,956 A | 11/1996 | Hanning |
| 5,577,137 A | 11/1996 | Groger et al. |
| 5,581,646 A | 12/1996 | Tsukamoto et al. |
| 5,585,639 A | 12/1996 | Dorsel et al. |
| 5,600,744 A | 2/1997 | Takahashi |
| 5,614,386 A | 3/1997 | Metzker et al. |
| 5,621,031 A | 4/1997 | Leimann et al. |
| 5,623,561 A | 4/1997 | Hartman |
| 5,631,170 A | 5/1997 | Attridge |
| 5,635,608 A | 6/1997 | Haugland et al. |
| 5,640,234 A | 6/1997 | Roth et al. |
| 5,671,303 A | 9/1997 | Shieh et al. |
| 5,677,196 A * | 10/1997 | Herron .................. C08G 65/329 356/244 |
| 5,677,769 A | 10/1997 | Bendett |
| 5,710,000 A | 1/1998 | Sapolsky et al. |
| 5,712,937 A | 1/1998 | Asawa et al. |
| 5,728,529 A | 3/1998 | Metzker et al. |
| 5,734,768 A | 3/1998 | Kim et al. |
| 5,737,457 A | 4/1998 | Saini et al. |
| 5,800,992 A | 9/1998 | Fodor et al. |
| 5,814,565 A | 9/1998 | Reichert et al. |
| 5,822,472 A | 10/1998 | Danielzik et al. |
| 5,830,766 A | 11/1998 | Attridge et al. |
| 5,832,165 A | 11/1998 | Reichert et al. |
| 5,861,242 A | 1/1999 | Chee et al. |
| 5,872,243 A | 2/1999 | Gee et al. |
| 5,919,712 A * | 7/1999 | Herron .................. C07C 281/02 385/12 |
| 5,998,796 A | 12/1999 | Liu et al. |
| 6,027,880 A | 2/2000 | Cronin et al. |
| 6,040,403 A | 3/2000 | Starzewski |
| 6,057,466 A | 5/2000 | Starzewski et al. |
| 6,078,705 A | 6/2000 | Neuschafer et al. |
| 6,108,463 A | 8/2000 | Herron et al. |
| 6,110,749 A | 8/2000 | Obremski et al. |
| 6,137,117 A | 10/2000 | Feldstein et al. |
| 6,141,465 A | 10/2000 | Bischel et al. |
| 6,191,852 B1 | 2/2001 | Paffhausen et al. |
| 6,222,619 B1 | 4/2001 | Herron et al. |
| 6,228,575 B1 | 5/2001 | Gingeras et al. |
| 6,239,876 B1 | 5/2001 | Brandenberg |
| 6,242,267 B1 | 6/2001 | Herron et al. |
| 6,287,871 B1 | 9/2001 | Herron et al. |
| 6,316,274 B1 | 11/2001 | Herron et al. |
| 6,335,793 B1 | 1/2002 | Freeman et al. |
| 6,361,947 B1 | 3/2002 | Dong et al. |
| 6,384,912 B2 | 5/2002 | Kraus et al. |
| 6,389,186 B1 | 5/2002 | DiGiovanni et al. |
| 6,395,558 B1 | 5/2002 | Duveneck et al. |
| 6,396,995 B1 | 5/2002 | Stuelpnagel et al. |
| 6,437,345 B1 | 8/2002 | Bruno-Raimondi et al. |
| 6,465,241 B2 | 10/2002 | Haronian et al. |
| 6,469,785 B1 | 10/2002 | Duveneck et al. |
| 6,483,096 B1 | 11/2002 | Kunz et al. |
| 6,492,468 B1 | 12/2002 | Chen et al. |
| 6,498,041 B1 | 12/2002 | Tabacco et al. |
| 6,522,408 B1 | 2/2003 | Bruck et al. |
| 6,580,941 B2 | 6/2003 | Webb |
| 6,618,536 B1 | 9/2003 | Heideman et al. |
| 6,632,609 B2 | 10/2003 | Lizardi |
| 6,661,938 B2 | 12/2003 | Lim et al. |
| 6,713,264 B2 | 3/2004 | Luttermann et al. |
| 6,759,663 B2 | 7/2004 | Tsipouras |
| 6,767,733 B1 * | 7/2004 | Green .................... B01L 3/502 422/82.11 |
| 6,777,244 B2 | 8/2004 | Pepper et al. |
| 6,785,432 B2 | 8/2004 | Letant et al. |
| 6,801,677 B1 | 10/2004 | Grace et al. |

(56) References Cited

U.S. PATENT DOCUMENTS

| | | |
|---|---|---|
| 6,830,936 B2 | 12/2004 | Anderson et al. |
| 6,847,746 B2 | 1/2005 | Uchiyama |
| 6,870,165 B2 | 3/2005 | Amirkhanian et al. |
| 6,947,634 B2 | 9/2005 | Tanaka et al. |
| 6,951,715 B2 | 10/2005 | Cunningham et al. |
| 6,956,651 B2 | 10/2005 | Lackritz et al. |
| 6,961,490 B2 | 11/2005 | Maisenhoelder et al. |
| 6,974,673 B2 | 12/2005 | Lockhart |
| 6,987,898 B2 | 1/2006 | Tran |
| 7,046,893 B2 | 5/2006 | Dorn et al. |
| 7,057,031 B2 | 6/2006 | Olejnik et al. |
| 7,058,255 B1 | 6/2006 | Fang |
| 7,101,945 B2 | 9/2006 | Dorn et al. |
| 7,122,012 B2 | 10/2006 | Bouton et al. |
| 7,175,811 B2 | 2/2007 | Bach et al. |
| 7,203,386 B2 | 4/2007 | Krol et al. |
| 7,227,147 B2 | 6/2007 | Riehle et al. |
| RE39,772 E | 8/2007 | Herron et al. |
| 7,292,336 B2 | 11/2007 | Cunningham et al. |
| 7,308,166 B1 | 12/2007 | Peng et al. |
| 7,313,424 B2 | 12/2007 | Mayevsky et al. |
| 7,349,080 B2 | 3/2008 | Aklian |
| 7,358,079 B2 | 4/2008 | Schürmann-Mader et al. |
| 7,373,063 B2 | 5/2008 | Nakata et al. |
| 7,396,675 B2 | 7/2008 | Pawlak et al. |
| 7,410,784 B2 | 8/2008 | Hatch |
| 7,444,053 B2 | 10/2008 | Schmidt et al. |
| 7,447,391 B2 | 11/2008 | Peled et al. |
| 7,483,140 B1 | 1/2009 | Cho et al. |
| 7,545,494 B2 | 6/2009 | Haiml et al. |
| 7,627,201 B2 | 12/2009 | Tiefenthaler |
| 7,708,945 B1 | 5/2010 | Abel et al. |
| 7,764,374 B2 | 7/2010 | Hubner et al. |
| 7,768,650 B2 | 8/2010 | Bazlenko |
| 7,811,754 B2 | 10/2010 | Herron et al. |
| 7,820,983 B2 | 10/2010 | Lundquist et al. |
| 7,838,847 B2 | 11/2010 | Lundquist et al. |
| 7,879,598 B2 | 2/2011 | Zesch et al. |
| 7,922,976 B2 | 4/2011 | Dutta et al. |
| 7,951,583 B2 | 5/2011 | Duer |
| 8,187,866 B2 | 5/2012 | Duer |
| 8,238,993 B2 | 8/2012 | Maynard et al. |
| 8,288,157 B2 | 10/2012 | Duer |
| 8,675,199 B2 | 3/2014 | Duer |
| 8,747,751 B2 | 6/2014 | Duer et al. |
| 9,423,397 B2 | 8/2016 | Duer |
| 9,528,939 B2 | 12/2016 | Duer |
| 2001/0055462 A1 | 12/2001 | Seibel |
| 2002/0045811 A1 | 4/2002 | Kittrell et al. |
| 2002/0114576 A1 | 8/2002 | Schroeder |
| 2002/0126936 A1 | 9/2002 | Lockhart |
| 2002/0126938 A1 | 9/2002 | Lockhart |
| 2002/0168780 A1 | 11/2002 | Liu et al. |
| 2002/0172457 A1 | 11/2002 | Tapalian et al. |
| 2002/0197456 A1 | 12/2002 | Pope |
| 2003/0063851 A1 | 4/2003 | Hillendahl et al. |
| 2003/0091277 A1 | 5/2003 | Mei |
| 2003/0108274 A1 | 6/2003 | Haronian |
| 2003/0108291 A1 | 6/2003 | Duveneck et al. |
| 2003/0138208 A1 | 7/2003 | Pawlak et al. |
| 2003/0169956 A1 | 9/2003 | Lange et al. |
| 2004/0008919 A1 | 1/2004 | Freeman et al. |
| 2004/0020987 A1 | 2/2004 | Nishioka et al. |
| 2004/0022475 A1 | 2/2004 | Pennington |
| 2004/0023396 A1 | 2/2004 | Boyd et al. |
| 2004/0036949 A1 | 2/2004 | Trezza |
| 2004/0046128 A1 | 3/2004 | Abel et al. |
| 2004/0052489 A1 | 3/2004 | Duveneck et al. |
| 2004/0081384 A1 | 4/2004 | Datesman et al. |
| 2004/0105644 A1 | 6/2004 | Dawes |
| 2004/0142370 A1 | 7/2004 | Dosmann et al. |
| 2004/0191119 A1 | 9/2004 | Zanzucchi et al. |
| 2004/0197044 A1 | 10/2004 | Bloom |
| 2005/0018949 A1 | 1/2005 | Yan |
| 2005/0043139 A1 | 2/2005 | Kennedy |
| 2005/0088648 A1 | 4/2005 | Grace et al. |
| 2005/0089261 A1 | 4/2005 | Shimazaki |
| 2005/0110989 A1 | 5/2005 | Schermer |
| 2005/0145783 A1 | 7/2005 | Zheng |
| 2005/0153320 A1 | 7/2005 | Herron et al. |
| 2005/0163659 A1 | 7/2005 | Duveneck et al. |
| 2005/0175273 A1 | 8/2005 | Lida et al. |
| 2005/0195394 A1 | 9/2005 | Ma et al. |
| 2005/0196102 A1 | 9/2005 | Yamazaki et al. |
| 2005/0201657 A1 | 9/2005 | Tiefenthaler |
| 2005/0201659 A1 | 9/2005 | Strecker |
| 2005/0227231 A1 | 10/2005 | Tcherkassov |
| 2005/0254744 A1 | 11/2005 | Freeman |
| 2006/0008227 A1 | 1/2006 | Schmidt et al. |
| 2006/0014151 A1 | 1/2006 | Ogura et al. |
| 2006/0061754 A1 | 3/2006 | Turner et al. |
| 2006/0072873 A1 | 4/2006 | Tekippe et al. |
| 2006/0073491 A1 | 4/2006 | Joseph et al. |
| 2006/0078889 A1 | 4/2006 | Bhattacharjee et al. |
| 2006/0098927 A1 | 5/2006 | Schmidt et al. |
| 2006/0115230 A1 | 6/2006 | Komoguchi et al. |
| 2006/0183145 A1 | 8/2006 | Turner |
| 2007/0077595 A1 | 4/2007 | Koo et al. |
| 2007/0222704 A1 | 9/2007 | Huang |
| 2007/0231458 A1 | 10/2007 | Gale et al. |
| 2007/0231880 A1 | 10/2007 | Chang-Yen et al. |
| 2008/0117418 A1 | 5/2008 | Claps et al. |
| 2008/0128627 A1* | 6/2008 | Lundquist .......... G01N 21/6452 250/363.01 |
| 2008/0243181 A1 | 10/2008 | Schneider et al. |
| 2009/0069199 A1 | 3/2009 | Brandenburg |
| 2009/0142790 A1* | 6/2009 | Fang ................ G01N 33/54373 435/29 |
| 2010/0072396 A1 | 3/2010 | Agranat et al. |
| 2010/0167413 A1 | 7/2010 | Lundquist et al. |
| 2010/0202925 A1 | 8/2010 | Sonnleitner |
| 2010/0248352 A1 | 9/2010 | Song et al. |
| 2010/0256016 A1 | 10/2010 | Blair et al. |
| 2010/0279429 A1 | 11/2010 | Hildenbrand et al. |
| 2011/0028346 A1 | 2/2011 | Chakravarty et al. |
| 2012/0196383 A1 | 8/2012 | Nitkowski et al. |
| 2012/0231532 A1 | 9/2012 | Duer |
| 2013/0063726 A1 | 3/2013 | Monro et al. |
| 2016/0033412 A1 | 2/2016 | Tan et al. |

FOREIGN PATENT DOCUMENTS

| | | |
|---|---|---|
| EP | 517516 B1 | 12/1999 |
| EP | 671626 B1 | 1/2000 |
| EP | 918984 B1 | 6/2001 |
| EP | 901620 B1 | 1/2002 |
| EP | 783683 B1 | 4/2004 |
| EP | 1413876 A2 | 4/2004 |
| EP | 901623 B1 | 6/2004 |
| EP | 1441217 A2 | 7/2004 |
| EP | 1315968 B1 | 2/2008 |
| EP | 1635177 B1 | 7/2008 |
| EP | 2154128 B1 | 12/2010 |
| EP | 2144947 B1 | 3/2011 |
| EP | 1356291 B1 | 5/2011 |
| EP | 2172503 B1 | 7/2011 |
| GB | 2377492 A | 1/2003 |
| JP | H11-281647 A | 10/1999 |
| JP | 2007101327 A | 4/2007 |
| JP | 2008513782 A | 5/2008 |
| JP | 2010160087 A | 7/2010 |
| WO | WO 94/18544 A1 | 8/1994 |
| WO | WO 94/27137 A2 | 11/1994 |
| WO | WO 95/14225 A1 | 5/1995 |
| WO | WO 95/33197 A1 | 12/1995 |
| WO | WO 96/26432 A1 | 8/1996 |
| WO | WO 97/35176 A1 | 9/1997 |
| WO | WO 97/35181 A1 | 9/1997 |
| WO | WO 97/35203 A1 | 9/1997 |
| WO | WO 97/39370 A1 | 10/1997 |
| WO | WO 99/14594 A1 | 3/1999 |
| WO | WO 99/45354 A2 | 9/1999 |
| WO | WO01/55691 A2 | 8/2001 |
| WO | WO02/37148 A2 | 5/2002 |

(56) References Cited

FOREIGN PATENT DOCUMENTS

| WO | WO02/40998 A2 | 5/2002 |
|---|---|---|
| WO | WO 02/46756 A1 | 6/2002 |
| WO | WO 02/066983 A2 | 8/2002 |
| WO | WO 03/006625 A2 | 1/2003 |
| WO | WO 03/021253 A2 | 3/2003 |
| WO | WO04/013616 A | 2/2004 |
| WO | WO 04/020987 A1 | 3/2004 |
| WO | WO04/23142 A1 | 3/2004 |
| WO | WO04/023143 A2 | 3/2004 |
| WO | WO 05/043139 A1 | 5/2005 |
| WO | WO 05/084367 A2 | 9/2005 |
| WO | WO 06/135782 A2 | 12/2006 |
| WO | WO 2007/070869 A2 | 6/2007 |
| WO | WO 2007/094817 A2 | 8/2007 |
| WO | WO 2007/123763 A2 | 11/2007 |
| WO | WO 2008/069973 A2 | 6/2008 |
| WO | WO2010/030251 A2 | 3/2010 |
| WO | WO2012/033466 A1 | 3/2012 |

OTHER PUBLICATIONS

Batzer et al.; Enhanced evolutionary PCR using Oligonucleotides with Inosine at the 3'-terminus; Nucleic Acid Res.; vol. 19; No. 18; p. 5081; Jul. 1991.
Bieche et al.; Quantitation of MYC Gene Expression in Sporadic Breast Tumors with a Real-time Reverse Transcription-PCR Assay; Cancer Res: vol. 59, No. 12, pp. 2759-2765; Jun. 1999.
Burgess et al.; A New Photolabile Protecting Group for Nucleotides; Abstracts of Papers Part 2.; 211th ACS National Meeting, American Chemical Society; New Orleans, LA; Mar. 24-28, 1996.
Chee et al.; Accessing Genetic Information with High Density DNA Arrays; Science; vol. 274, pp. 610-614; Oct. 1996.
Herron et al.; Orientation and Activity of Immobilized antibodies in: Biopolymers at Interfaces, 2nd Edition; Surfacant Science Series; Marcel Dekker, New York; vol. 110, pp. 115-163; Jan. 2003.
Herron et al.; Planar Waveguide Biosensors for Point-of-Care Clinical and Molecular Diagnositics in: Fluorescence Sensors and Biosensors; R. B. Thompson, Ed. CRC Press Taylor & Francis Group; Boca Raton, FL; pp. 283-332; Dec. 2005.
Hutchison, Clyde A.; DNA sequencing: bench to bedside and beyond; Nucleic Acid Res.; vol. 35; No. 18; pp. 6227-6237; Sep. 2007.
Innis et al.; PCP Protocols: A Guide to Methods and Applications; Elsevier Science & Technology; Jan. 1990.
Kaplan et al.;Rapid photolytic release of adenosine 5'-triphosphate from a protected analog: utilization by the sodium:potassium pump of human red blood ghost cells; Biochemistry; vol. 17; pp. 1929-1935; May 1978.
Kreuzer et al.; LightCycler Technology for the Quantitation of BCR/ABL Fusion Transcripts; Cancer Res.; vol. 59; No. 13; pp. 3171-3174; Jul. 1999.
Kulagina et al.; Antimicrobial peptides as new recognition molecules for screening challenging species; (Author Manuscript) Sens. Actuators B. chem.; vol. 121 (1); pp. 150-157; Jan. 2007.
Laurendeau et al.; TaqMan PCR-based gene dosage assay for predictive testing in individuals from a cancer family with INK4 locus haploinsufficiency; Clin Chem; vol. 45; No. 7; pp. 982-986; May 1999.
Levene et al.; Zero-Mode Waveguides for Single-Molecule Analysis at High Concentrations; Science; vol. 299; pp. 682-686; Jan. 31, 2003.
Lockhart et al.; Expression monitoring by hybridization to high-density oligonucleotide arrays; Nature Biotechnology; vol. 14; pp. 1675-1680; Dec. 1996.
McCray et al.; A new approach to time-resolved studies of ATP-requiring biological systems; laser flash photolysis of caged ATP; Proc. Natl. Acad. Sci. USA; vol. 77; No. 12; pp. 7237-7241; Dec. 1980.
Metzker et al.; Termination of DNA synthesis by novel 3'-modified-deoxyribonucleoside 5'-triphosphates; Nucleic Acids Res.; vol. 22; No. 20; pp. 4259-4267; Oct. 1994.
Ohtsuka et al.; An alternative approach to deoxyoligonucleotides as hybridization probes by insertion of deoxyinosine at ambiguous codon positions; J. Biol. Chem; vol. 260; pp. 2605-2608; Mar. 1985.
Pillai, Rajasekharan V.N.; V.N.; Photoremovable Protecting Groups in Organic Synthesis ; Synthesis; 1980(1); pp. 1-26; Jan. 1980.
Plowman et al.; Femtomolar Sensitivity using a channel-etched Thin Film Waveguide Fluoroimmunosensor; Biosensors & Bioelectronics; vol. 11(1-2); pp. 149-160; Jan. 1996.
Rossolini et al.; Use of deoxyinosine-containing primers vs degenerate primers for polymerase chain reaction based on ambiguous sequence imformation; Mol. Cell. Probes.; vol. 8; pp. 91-98; Jun. 1994.
Saizieu et al.; Bacterial transcript imaging by hybridization of total RNA to oligonucleotide arrays; Nat Biotechnol; vol. 16; No. 1; pp. 45-48; Jan. 1998.
Sun et al.; Synthesis of Novel Flourinated Coumarins: Excellent UV-Light Excitable Flourencent Dyes: Bioorganic & Med. Letters; vol. 8; No. 22; pp. 3107-3110; Nov. 1998.
Xu et al.; Protein and chemical microarrays—powerful tools for proteomics; J Biomed Biotechnol; vol. 2003(5); pp. 257-266; Dec. 2003.
Zehavi et al.; J. Light-sensitive glycosides. I. 6-nytroveratryl .beta.-D-glucopyranoside and 2-nitrobenzyl beta.-D-glucopyranoside; J. Organic Chem.; vol. 37(14); pp. 2281-2285; Jul. 1972.
Zourob et al.; Principles of bacterial detection: Biosensors, Recognition Receptors and microsystems; Eds., Springer Science and Business Media, NY; pp. 178-180; Jun. 2008.
Duer; U.S. Appl. No. 15/245,062 entitled "Waveguide-based detection system with scanning light source," filed Aug. 23, 2016.
Duer; U.S. Appl. No. 15/353,641 entitled "Waveguide-based optical scanning systems," filed Nov. 16, 2016.
Duer; U.S. Appl. No. 15/550,250 entitled "Waveguide-based detection system with scanning light source," filed Aug. 10, 2017.

\* cited by examiner

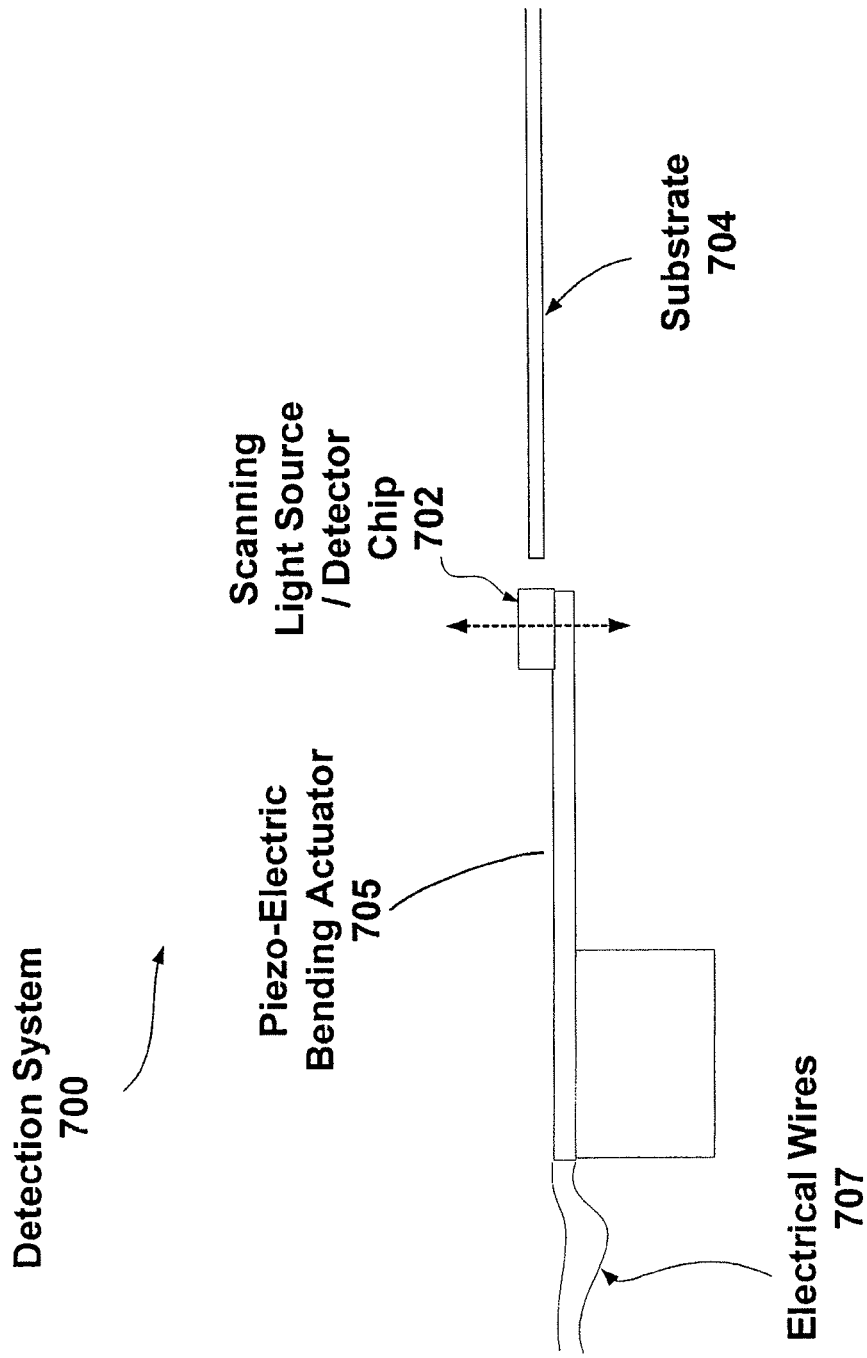

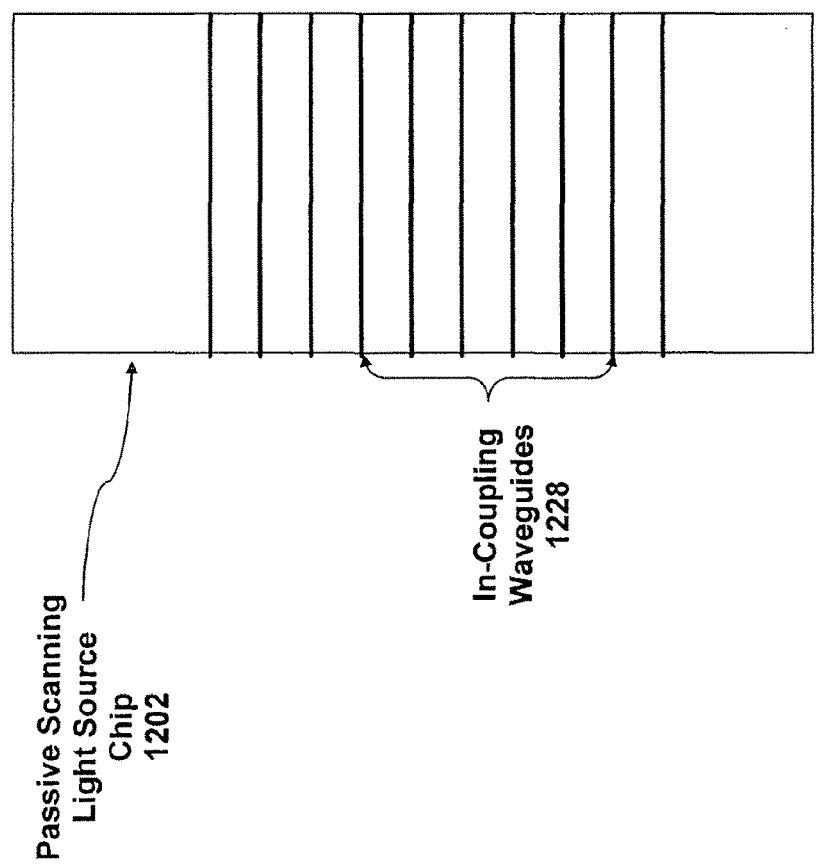

WAVEGUIDE-BASED DETECTION SYSTEM WITH SCANNING LIGHT SOURCE

CROSS REFERENCE TO RELATED APPLICATIONS

This application is a continuation-in-part of U.S. patent application Ser. No. 15/245,062, filed Aug. 23, 2016, titled "WAVEGUIDE-BASED DETECTION SYSTEM WITH SCANNING LIGHT SOURCE," which is a continuation of U.S. patent application Ser. No. 14/194,437, filed Feb. 28, 2014, titled "WAVEGUIDE-BASED DETECTION SYSTEM WITH SCANNING LIGHT SOURCE," now U.S. Pat. No. 9,423,397, which is a continuation-in-part of U.S. patent application Ser. No. 12/769,364, filed Apr. 28, 2010, titled "WAVEGUIDE-BASED DETECTION SYSTEM WITH SCANNING LIGHT SOURCE," now U.S. Pat. No. 8,675,199, which claims benefit under 35 U.S.C. § 119(e) of U.S. Patent Provisional Application No. 61/173,771, filed Apr. 29, 2009, titled "GENERATION OF OPTICAL PULSES IN A WAVEGUIDE USING A SPATIALLY SCANNING LIGHT SOURCE" and U.S. Patent Provisional Application No. 61/223,550 filed Jul. 7, 2009 and titled "WAVEGUIDE-BASED DETECTION WITH SCANNING LIGHT SOURCE," each of which is herein incorporated by reference in its entirety.

U.S. patent application Ser. No. 12/769,364 is also a continuation-in-part of U.S. patent application Ser. No. 11/683,808, filed Mar. 8, 2007, titled "OPTICAL SCANNING SYSTEM," now U.S. Pat. No. 7,951,583, which claims benefit under 35 U.S.C. § 119(e) of U.S. Patent Provisional Application No. 60/743,458, filed Mar. 10, 2006 and titled "OPTICAL SCANNING SYSTEM," each of which is herein incorporated by reference in its entirety.

U.S. patent application Ser. No. 12/769,364 is also a continuation-in-part of U.S. patent application Ser. No. 12/209,295, filed Sep. 12, 2008, titled "WAVEGUIDE-BASED OPTICAL SCANNING SYSTEMS," now U.S. Pat. No. 8,288,157, which claims benefit under 35 U.S.C. § 119(e) of U.S. Patent Provisional Application No. 60/971,878, filed Sep. 12, 2007, and titled "WAVEGUIDE-BADED OPTICAL SCANNING SYSTEMS," each of which is herein incorporated by reference in its entirety.

This application also claims priority to U.S. Provisional Application No. 62/235,977, filed Oct. 1, 2015, which is herein incorporated by reference in its entirety.

INCORPORATION BY REFERENCE

All publications and patent applications mentioned in this specification are herein incorporated by reference to the same extent as if each individual publication or patent application was specifically and individually indicated to be incorporated by reference.

FIELD

The present invention relates to methods and devices for generating optical pulses in one or more waveguides using a spatially scanning light source, and to detection systems, methods of use thereof and kits for detecting a biologically active analyte molecule.

BACKGROUND

Biological substance analysis methods based on optical means have risen in popularity in the last couple of decades. Common to all these methods is that chemical interactions between the bio-molecules produce changes that affect some measurable optical property, such as the emission spectrum, absorption spectrum or index of refraction. The changes in the optical properties can occur in the analyte itself or through a mediator such as the surface on which the interaction takes place. These changes are then monitored using a beam of incoming light (usually laser light) which in turn changes the outgoing light spectrum (e.g., fluorescence), intensity (e.g., absorption), or phase (e.g., surface plasmon resonance and any kind of interferometric method).

While most of these optical bio-analysis methods have found niche applications and markets, one method that became highly popular and influential was microarray optical fluorescence scanning Such optical scanning has enabled running tests on tens of thousands of miniature samples in a relatively short period of time. The major advantages of this method include: a) performance (sensitivity and signal to noise ratio (SNR)); b) speed; and c) miniaturization of the sampled analyte. These parameters define the efficiency and superiority of the method.

Currently microarray elements are spotted on top of a flat substrate chip usually made of glass, plastic or epoxy. Subsequently, the chip is scanned using confocal scanning systems where the exciting light and the resulting fluorescence light are both shined and collected from above and analyzed using a single photo-multiplier (PMT) detector. This arrangement suffers from several inherent limitations including a very short interaction length between the bio-sample and the light (usually a single mono-layer). This limits the signal strength and thus the SNR. Another limitation is a high background or noise due to the fact that the back-reflected light and the emitted fluorescent light travel in the same direction. A further limitation is high sensitivity to both the planarity and the position of the chip that need to be maintained in focus. Still another limitation is slow operation due to the need to have large enough number of 'pixels' (scanned spots) within every sample and long enough integration time. Yet another limitation is the need for a complicated optical and mechanical structure that entails bulky and expensive systems.

Another optical bio-analysis method is waveguide based bio-sensors. Bio-sensing based on waveguides has been around for a while. These biosensors can be divided into three main categories. The first involve slab waveguide fluorescence excitation with light collection from above or below the chip. In this arrangement the bio-analyzed spots are located on the surface of a chip that contains a single slab-waveguide. Light is coupled into the waveguide using a lens or a grating that excites the entire chip with all its bio-analyzed spots simultaneously. The fluorescence is collected using an optical imaging system and a charge-coupled device (CCD) detector from above or underneath the chip. One drawback of this kind of system is relatively poor performance due to uniformity of excitation as well as collection of the light. This leads to non-repeatable results. Another drawback is high noise levels due to crosstalk between the different spots. A further drawback is that large spots and relatively small numbers of elements are required to generate a signal large enough for efficient imaging with the CCD. Yet another drawback is the long integration time to overcome SNR issues. Examples of the above method are described in U.S. Pat. Nos. 5,814,565; 6,911,344 and 6,395,558.

A second waveguide based bio-sensor utilizes an interferometric optical device. In this case, channel waveguides are used together with interferometric devices such as Mach Zehnder interferometers (MZI) or ring-resonators. These sensitive interferometric devices sense the change in the index of refraction due to binding of the bio-molecules near a waveguide surface. The major problems associated with this type of system include non-specificity due to inability to recognize the exact reason for the index change, which may occur from deposition of other material as well as temperature changes. Another problem is a very slow speed in addressing the different elements which disqualifies this method for running large numbers of element arrays. Examples of the above method are described in U.S. Pat. Nos. 5,494,798 4,515,430, 5,623,561 and 6,618,536.

A third waveguide based bio-sensor utilizes surface plasmon resonance (SPR). Here, in one example, a thin gold layer is deposited on top of a glass substrate. The bio-analyzed sample on top of the gold induces changes in the refractive index above the gold layer, thus changing the resonant angle for generating surface plasmons along the gold layer. The plasmon generation is detected as an enhanced peak in the reflected beam. Examples of the SPR method are covered, for example, in U.S. Pat. No. 6,956,651 B2. Other types of optical bio-sensors and array scanners exist such as described in U.S. Pat. No. 6,396,995 B1.

One aspect common to all of these waveguide based sensors is the need to initially couple light into the waveguide. Since all of these optical waveguides have miniature cross-sections ranging from 100 micrometers down to a fraction of a micrometer, the coupling of light into the waveguide involves specialized optics for focusing the light, fine mechanical alignment for accurately placing the light source relative to the waveguide, and specialized glues to bond all components in place without interfering with the light. This process adds in most of these cases a considerable cost and complexity to the entire system.

In a large number of these optical waveguide applications, the light travels in the waveguide in the form of short pulses. These pulses can be as short as a pico ($10^{-12}$) second and as long as a few milli ($10^{-3}$) seconds. Moreover, these pulses can be all of the same wavelength or can be a combination of many different wavelengths. These pulses are generated by modulating one or more light sources which were initially coupled to the optical waveguide. If pulses at more than one wavelength are required, a combiner e.g., an Arrayed Waveguide Grating (AWG) must be added to the system.

In various applications, for example, biological analysis or detection systems, the optical waveguide may be part of a low-cost, consumable chip. Waveguide-based optical detection systems are disclosed, for example, in U.S. Pat. Nos. 7,951,583 B2, 8,187,866 B2 and 8,288,157 B2, each of which are hereby incorporated in their entirety by reference. In a system making use of such consumable chips, light needs to be coupled time after time to new chips. In such cases the cost and complexity of the light coupling technologies known in the art (see, for example, U.S. Pat. Nos. 4,881,789, 5,734,768, 5,600,744, 5,581,646, 5,444,805, 5,217,568, 5,121,457, 5,077,878, 4,744,623 and 4,478,485) are intolerable.

In addition, the optical signal generated on the sensing chip in all these applications is the result of one or more optical phenomena such as fluorescence, luminescence, absorption, scattering and optical phase change. Changes detected in the output light are indicative of the presence of the targets being detected. Nevertheless, the output light may also be affected by additional factors (e.g. temperature and aging) which may skew the results compromising the overall accuracy and precision of the detection system. Finding a method for normalizing the detected signal to overcome the effect of these uncontrolled factors is critical for maintaining the performance of the detection system.

SUMMARY OF THE DISCLOSURE

The present invention provides methods and devices which allow the coupling of light into one or more optical waveguides in a simple and cost-effective manner. The invention further provides methods and devices for simple coupling of multi-wavelength trains of pulses into an optical waveguide. The invention further provides methods and devices for coupling correlated trains of pulses of one or more wavelengths into multiple optical waveguides.

In one aspect, the invention provides a method for generating an optical pulse in an optical waveguide, comprising providing an optical waveguide having an internal portion configured to carry an optical signal and a first end face in contact with said internal portion; providing a light beam; and spatially translating the light beam relative to the optical waveguide effective that the light beam transiently contacts the first end face of the optical waveguide, whereby an optical pulse is generated in the waveguide.

In a further embodiment, the invention provides a method for generating an optical pulse in an optical waveguide wherein the light beam has an optical mode, wherein the optical waveguide has an optical mode, and wherein while the light beam transiently contacts the optical waveguide, the light beam optical mode transiently overlaps the optical mode of the waveguide effective that light from the light beam passes into and within the optical waveguide.

In embodiments of the invention, the method further comprises providing a light source capable of emitting a light beam. In some embodiments, the light source is a laser. In some embodiments, the light source is a light emitting diode (LED). In some embodiments, the light beam is reflected prior to contacting the optical waveguide. In some embodiments, the light beam is refracted prior to contacting the optical waveguide.

In embodiments of the invention, the light source is movable, and spatial translation of the light beam emitted from the light source is effected by movement of the light source. In various embodiments, the movement of the light source is rotational, vertical, horizontal, transverse or longitudinal. In other embodiments of the invention, the waveguide is movable, and spatial translation of the light beam emitted from the light source is effected by movement of the waveguide. In various embodiments, the movement of the waveguide is rotational, vertical, horizontal, transverse or longitudinal.

In embodiments of the invention, the light source is operably connected to an actuator. In other embodiments, the waveguide is operably connected to an actuator. The movement of the actuator may be effected by electrical power, thermal power, magnetic power or even mechanical power (i.e., manually). In various embodiments, the actuator is a piezoelectric based motor, a step motor, an electrical motor, a magnetic actuator, a "memory metal" actuator, a solenoid, or a hydraulic actuator.

In one embodiment, a light source is mounted on a piezoelectric bending actuator. Applying power to the actuator causes the actuator to move up and down, thereby scanning a line in space. The optical modes of any optical waveguide along this line will at some point overlap some of the optical modes of the light source and a pulse of light will be injected into the optical waveguide.

In a further embodiment, multiple light sources are mounted on a piezoelectric bending actuator. Every time the actuator scans its path, several optical pulses are injected into the optical waveguide. In some embodiments, the multiple light sources each emit light beams having a different wavelength. Every time the actuator scans its path, several optical pulses are injected into the optical waveguide, each at a different wavelength.

In further embodiments, multiple optical waveguides are arranged along the scanning path of the one or more light sources.

In an embodiment of the invention, a light source is mounted on the outer edge of a rotating disk, disposed effective that a light beam emitted from the light source is directed outwardly from the disk and transiently contacts an optical waveguide as the disk rotates. In further embodiments, multiple light sources are mounted on the rotating disk. In further embodiments, multiple optical waveguides are mounted around the rotating disk with their optical modes facing inward (toward the center of the disk). With every rotation of the disk, the optical mode of each and every light source will overlap once with the optical mode of each and every optical waveguide. Therefore the total number of pulses generated in each optical waveguide will be equal to the total number of light sources mounted on the disk.

In further embodiments of the invention, the light beams emitted from the light source are spatially translated. In various embodiments, the emitted light beams are spatially translated by a lens, a prism, a mirror, or a combination thereof. In some embodiments, the mirror is a stirring mirror.

In one embodiment, a lens placed in front of the light source is translated in space, causing the light beam emitted by the light source to scan through space until its optical mode overlaps the optical mode of an optical waveguide.

In another embodiment, a stirring mirror placed in front of the light source stirs the emitted light beam through space until its optical mode overlaps the optical mode of the optical waveguide.

In a further aspect, the invention provides an apparatus for optical pulse generation in an optical waveguide, comprising a light source for emitting a light beam; an optical waveguide having a first end; and means for spatially translating a light beam from said light source such that the optical mode of the light source transiently contacts said the first end of the optical waveguide effective to provide an optical pulse in the waveguide.

In embodiments of the invention the apparatus further comprises one or more additional light sources, and/or one or more additional optical waveguides. In some embodiments, the apparatus comprises multiple light sources each of which emits light beams having a different wavelength.

In various embodiments, the means for spatially translating the light beam from the light source relative to the optical waveguide comprises a mechanism selected from a rotating disk, a motor, a solenoid, a hydraulic mechanism, a piezo-electric mechanism, and a "memory-metal" mechanism.

In an embodiment, the light source is mounted on an outer edge of a rotatable disk, wherein said light source is disposed effective that a light beam emitted by said light source is directed outwardly of said rotatable disk, and that said light beam emitted by said light source is directed effective to transiently contact a first end of an optical waveguide as said disk rotates.

In a further embodiment, the light source is mounted on an actuator effective that a light beam emitted by said light source is directed effective to transiently contact a first end of an optical waveguide as said actuator moves.

In a further embodiment, the apparatus further comprises a scanning lens mounted on an actuator, wherein said scanning lens is disposed between the light source and the optical waveguide effective that movement of the actuator causes a light beam emitted by said light source to be directed by the lens effective to transiently contact a first end of an optical waveguide.

In a further embodiment, the apparatus further comprises a stirring mirror wherein said stirring mirror is disposed between the light source and the optical waveguide effective that movement of the stirring mirror causes a light beam emitted by said light source to be directed by the stirring mirror effective to transiently contact a first end of an optical waveguide.

In a further aspect, the invention provides optical detection systems which utilize any of the above described methods or devices for coupling light into an optical waveguide. The invention further provides the use of such detection systems for applications including but not limited to detection of a biological marker, detection of a chemical or biological warfare agent, detection or diagnosis of a viral or bacterial infectious disease, diagnosis of a genetic disorder or a cancer, detection of a protein-protein, protein-ligand, or protein-small molecule interaction, nucleic acid sequencing, and environmental monitoring of air, water, soil and food samples.

The present invention further provides detection systems and methods of use thereof including a scanning light source, a detector and a substrate comprising a plurality of waveguides and a plurality of optical sensing sites. The light source is spatially translated relative to the substrate such that light emitted from the light source is coupled to and in optical communication with the waveguides of the substrate at some point along its scanning path. The use of a scanning light source allows the coupling of light into the waveguides of the substrate in a simple and cost-effective manner.

In general, the invention features a detection system and methods of use thereof including a scanning light source, a substrate comprising a plurality of waveguides and a plurality of optical sensing sites in optical communication with one or more waveguide of the substrate, a detector that is coupled to and in optical communication with the substrate, and means for spatially translating a light beam emitted from said scanning light source such that the light beam is coupled to and in optical communication with one or more waveguides of the substrate at some point along its scanning path.

In some embodiments of the invention, the scanning light source is a chip comprising light generating elements. In further embodiments, the scanning light source chip further comprises waveguides. In alternative embodiments, the scanning light source is a chip that is further coupled to and in optical communication with an external light source. In some embodiments, the external light source is coupled to the scanning light source chip by optical fibers. In some embodiments, the scanning light source chip further includes waveguides.

In some embodiments, the substrate comprises a plurality of substantially parallel excitation waveguides, and a plurality of substantially parallel collection waveguides, the excitation waveguides and collection waveguides crossing to form a two-dimensional array of intersection regions where an excitation waveguide and a collection waveguide cross and provide optical communication with the intersection region at each crossing; and a plurality of optical sensing sites each in optical communication with an intersection region. The system further comprises a scanning light source that is at some point along its scanning path coupled to and in optical communication with one or more of the excitation waveguides at a first edge of the substrate, and a detector that is coupled to and in optical communication with one or more of the collection waveguides at a second edge of the substrate. In some embodiments, two or more detectors are coupled to and in optical communication with one or more collection waveguides at various edges of the substrate.

In other embodiments, the substrate comprises a plurality of substantially parallel waveguides, and a plurality of optical sensing sites each in optical communication with a waveguide. The system further comprises a scanning light source that is at some point along its scanning path coupled to and in optical communication with one or more of the waveguides at a first edge of the substrate, and a detector that is coupled to and in optical communication with said waveguides at the same or an opposite edge of the substrate. In some embodiments, the substrate comprises a plurality of in-coupling waveguides and a plurality of out-coupling waveguides, and a plurality of optical sensing sites each in optical communication with an in-coupling and an out-coupling waveguide. The system further comprises a scanning light source that is at some point along its scanning path coupled to and in optical communication with one or more of the in-coupling waveguides at a first edge of the substrate, and a detector that is coupled to and in optical communication with one or more of the outcoupling waveguides of the substrate.

In some embodiments, the scanning light source further comprises a detector, wherein at the point at which the light source is coupled to and in optical communication with one or more of the plurality of waveguides in optical communication with the optical sensing site, the detector is also coupled to and in optical communication with said one or more waveguides. In some embodiments, the substrate comprises a plurality of in-coupling waveguides and a plurality of out-coupling waveguides, wherein at the point at which the light source is coupled to and in optical communication with one or more of the in-coupling waveguides, the detector is coupled to and in optical communication with one or more of the out-coupling waveguides.

In some embodiments of the invention, the scanning light source is a chip comprising light generating elements and detector elements. In further embodiments, the scanning light source chip further comprises in-coupling and out-coupling waveguides. In further embodiments, the scanning light source chip further comprises at least one combiner. In alternative embodiments, the scanning light source is a chip that is further coupled to and in optical communication with an external light source and an external detector source. In some embodiments, the external light source is coupled to the scanning light source chip by optical fibers. In some embodiments, the scanning light source chip further includes incoupling and outcoupling waveguides. In further embodiments, the scanning light source chip further comprises at least one combiner.

In some embodiments of the invention, the optical sensing site further comprises a sensor configured to transduce a first light wave generated by the light source in a waveguide, resulting in a second light wave in a different waveguide, the second light wave being detectable by the detector. In other embodiments, the optical sensing site further comprises a sensor configured to transduce a first light wave generated by the light source in a waveguide, resulting in a second light wave in the same waveguide, the second light wave being detectable by the detector.

In some embodiments, the light source elements can provide variable wavelengths of light. In some embodiments, the light source is a broad-band source. In other embodiments, the light source is a tunable source. In various embodiments, the light source elements may be light emitting diodes (LEDs) or laser diodes (LDs). In various embodiments, the detector elements of the detector or of the scanning light source chip may be PIN diodes, avalanche photo-diodes, or a group of pixels which are part of a charge coupled device (CCD) array. In some embodiments, the detector is a silicon photodiode array.

In embodiments of the invention, the scanning light source is movable, and spatial translation of the light beam emitted from the light source is effected by movement of the scanning light source. In further embodiments, spatial translation of the light beam emitted from the light source is effected by movement of a component of the scanning light source, such as one or more mirrors, lenses, or prisms. In alternative embodiments, the substrate is movable, and, and spatial translation of the light beam emitted from the light source is effected by movement of the substrate. In various embodiments, the means for spatially translating the light beam from the light source relative to optical waveguides of the substrate comprises a mechanism selected from a rotating disk, a motor, a solenoid, a hydraulic mechanism, a piezoelectric mechanism, and a memory-metal mechanism. In embodiments of the invention, the scanning light source is operably connected to an actuator. The movement of the actuator may be effected by electrical power, thermal power, magnetic power or even mechanical power (i.e., manually). In various embodiments, the actuator is a piezoelectric based motor, a step motor, an electrical motor, a magnetic actuator, a memory metal actuator, a solenoid, or a hydraulic actuator. In some embodiments, the actuator is a piezoelectric bending actuator.

In general, in yet another aspect, the invention provides a detection method comprising delivering a sample suspected of containing a biologically active analyte molecule to be detected to an optical sensing site on the substrate of a detection system, and spatially translating a scanning light source to a point at which the light source is coupled to and in optical communication with one or more of a plurality of waveguides in optical communication with the optical sensing site, thereby generating a first light wave within said waveguide, wherein the first light wave is transducable by a sensor associated with the optical sensing site to a second light wave. Furthermore, the method comprises detecting a measurable change in the second light wave using a detector in optical communication with the substrate, wherein a measurable change in the second light wave occurs when the sensor interacts with the biologically active analyte molecule.

In some embodiments, the substrate comprises a plurality of substantially parallel excitation waveguides in optical communication with optical sensing site, wherin first light wave is transducable by a sensor associated with the optical sensing site to a second light wave carried in one or more of a plurality of substantially parallel collection waveguides in optical communication with the optical sensing site and crossing the excitation waveguides; and wherein a measurable change in the second light wave is detected using a detector in optical communication with the collection waveguides, wherein a measurable change in the second light wave occurs when the sensor interacts with the biologically active analyte molecule.

In other embodiments the substrate comprises a plurality of in-coupling and out-coupling waveguides in optical communication with the optical sensing site, and at the point at which the light source is coupled to and in optical communication with one or more of a plurality of in-coupling waveguides in optical communication with the optical sensing site, the detector is coupled to and in optical communication with one or more out-coupling waveguides.

In other embodiments, the scanning light source further comprises a detector, and at the point at which the light source is coupled to and in optical communication with one or more waveguides in optical communication with the optical sensing site, the detector is also coupled to and in optical communication with said one or more waveguides. In further embodiments the substrate comprises a plurality of in-coupling and out-coupling waveguides in optical communication with the optical sensing site, and the scanning light source further comprises a detector; and at the point at which the light source is coupled to and in optical communication with one or more of a plurality of in-coupling waveguides in optical communication with the optical sensing site, the detector is coupled to and in optical communication with one or more out-coupling waveguides.

In various embodiments of the methods of the invention, the biologically active analyte is selected from the group consisting of a nucleic acid, a protein, an antigen, an antibody, a microorganism, a gas, a chemical agent and a pollutant. In some embodiments, detecting a measurable change in the second light wave provides a diagnostic result.

In some embodiments of the invention, a SNP is detected in the biologically active analyte. In other embodiments of the invention, expression of a gene is detected upon detection of the biologically active analyte. In some embodiments, the method further comprises conducting a real-time PCR reaction at the optical sensing site.

In some embodiments of the invention, the sensor is adapted to support an immunoassay wherein the sensor interacting with the biologically active analyte comprises an outcome of an immunoassay. In further embodiments, the immunoassay supported is an enzyme-linked immunosorbent assay (ELISA). In further embodiments, the immunoassay supported is a fluorescent immunoassay.

The invention further provides the use of the detection systems for applications including but not limited to detection of biomarkers, detection of a chemical or biological warfare agent, detection or diagnosis of viral and bacterial infectious diseases, diagnosis of a genetic disorder or a cancer, detection of a protein-protein, protein-ligand, or protein-small molecule interaction, nucleic acid sequencing, and environmental monitoring of air, water, soil and food samples.

In some embodiments, a detection system for detecting a biologically active analyte molecule is provided. The system includes a substrate comprising one or more excitation waveguides, a plurality of collection waveguides, the one or more excitation waveguides and the plurality of collection waveguides crossing to form an array of intersection regions where an excitation waveguide and a collection waveguide cross and provide optical communication with the intersection region at each crossing, and a plurality of optical sensing sites each in optical communication with an intersection region; a scanning light source, wherein the scanning light source is at some point along its scanning path in optical communication with at least one of the one or more excitation waveguides; a detector that is in optical communication with one or more of the collection waveguides; and an actuator for spatially translating a light beam emitted from the scanning light source relative to the substrate such that the light beam is coupled to and in optical communication with at least one of the one or more excitation waveguides of the substrate at some point along its scanning path.

In some embodiments, the one or more excitation waveguides is a single excitation waveguide.

In some embodiments, both the one or more excitation waveguides and the plurality of collection waveguides exit the substrate at a first edge of the substrate.

In some embodiments, the scanning light source is at some point along its scanning path in optical communication with one or more of the excitation waveguides at the first edge of the substrate; and the detector is in optical communication with one or more of the collection waveguides at the first edge of the substrate.

In some embodiments, the one or more excitation waveguides are curved about 90 degrees.

In some embodiments, a detection method is provided. The method includes delivering a sample suspected of containing a biologically active analyte molecule to be detected to an optical sensing site on a substrate of a detection system, the substrate comprising one or more excitation waveguides and a plurality of collection waveguides; spatially translating a scanning light source to a point at which the light source is in optical communication with at least one of the one or more excitation waveguides, wherein at least one of the one or more excitation waveguides is in optical communication with the optical sensing site, thereby generating a first light wave within said at least one of the one or more excitation waveguides, wherein the first light wave is transducable by a sensor associated with the optical sensing site to a second light wave carried in one or more of the plurality of collection waveguides in optical communication with the optical sensing site and crossing the one or more excitation waveguides; and detecting a measurable change in the second light wave using a detector in optical communication with one or more of the plurality collection waveguides, wherein a measurable change in the second light wave occurs when the sensor interacts with the biologically active analyte molecule.

In some embodiments, the scanning light source further comprises a detector, and wherein at the point at which the light source is coupled to and in optical communication with one or more waveguides in optical communication with the optical sensing site, the detector is also coupled to and in optical communication with said one or more waveguides.

In some embodiments, the biologically active analyte is selected from the group consisting of a nucleic acid, a protein, an antigen, an antibody, a microorganism, a gas, a chemical agent and a pollutant.

In some embodiments, the sensor is adapted to support an immunoassay and wherein the sensor interacting with the biologically active analyte comprises an outcome of an immunoassay.

In some embodiments, the one or more excitation waveguides is a single excitation waveguide.

In some embodiments, both the one or more excitation waveguides and the plurality of collection waveguides exit the substrate at a first edge of the substrate.

In some embodiments, the scanning light source is at some point along its scanning path in optical communication with one or more of the excitation waveguides at the first edge of the substrate; and the detector is in optical communication with one or more of the collection waveguides at the first edge of the substrate.

In some embodiments, the one or more excitation waveguides are curved about 90 degrees.

The present invention relates to methods and systems of signal normalization, and more particularly to methods and systems of normalizing a signal generated in a waveguide based sensing chip used in bio-sensing applications.

In some embodiments, a method of measuring a concentration of an analyte using a waveguide chip is provided. The method can include adding a known amount of one or more normalizing moieties to a sample; adding a first detection molecule labelled with a first fluorescent tag to the sample, the first detection molecule specific to the analyte; adding one or more secondary detection molecules, each secondary detection molecule labelled with a distinct secondary fluorescent tag, to the sample, the one or more secondary detection molecules specific to the one or more normalizing moieties, wherein the first fluorescent tag and the one or more secondary fluorescent tags emit at different fluorescence wavelengths; introducing the sample to an array of sensing sites on the waveguide chip, each sensing site of the array having a first capture molecule specific to the analyte and one or more secondary capture molecules specific to the one or more normalizing moieties, wherein the first capture molecule and the one or more secondary capture molecules are both immobilized in each sensing site of the array at a predetermined ratio; introducing a first light pulse into one or more excitation waveguides on the waveguide chip at a first predetermined interval, the one or more excitation waveguides in optical communication with the array of sensing sites, the first light pulse configured to excite the first fluorescent tag; introducing one or more secondary light pulses into the one or more excitation waveguides on the waveguide chip at one or more secondary predetermined intervals, wherein the first light pulse and the one or more secondary light pulses have different wavelengths, the one or more secondary light pulses configured to excite the one or more secondary fluorescent tags; measuring the fluorescence emitted by the first detection molecule and the one or more secondary detection molecules through a plurality of collection waveguides in optical communication with the array of sensing sites; and normalizing the measured fluorescence emitted by the first detection molecule using the measured fluorescence emitted by the one or more secondary detection molecules.

In some embodiments, the step of normalizing the measured fluorescence emitted by the first detection molecule includes dividing the measured fluorescence emitted by the first detection molecule by the measured fluorescence emitted by the one or more secondary detection molecules.

In some embodiments, the first detection molecule, the one or more secondary detection molecules, the first capture molecule, and the one or more secondary capture molecules are antibodies.

In some embodiments, the step of normalizing the measured fluorescence emitted by the first detection molecule further includes generating one or more calibration curves from the measured fluorescence emitted by the one or more secondary detection molecules.

In some embodiments, the one or more normalizing moieties includes at least a first normalizing moiety and a second normalizing moiety, wherein the amount of the first normalizing moiety added to the sample is greater than the amount of the second normalizing moiety added to the sample.

In some embodiments, the step of normalizing the measured fluorescence emitted by the first detection molecule includes dividing the measured fluorescence emitted by the first detection molecule by a slope of the measured fluorescence emitted by the one or more secondary detection molecules.

In some embodiments, the step of normalizing the measured fluorescence emitted by the first detection molecule includes dividing a slope of the measured fluorescence emitted by the first detection molecule by a slope of the measured fluorescence emitted by the one or more secondary detection molecules.

In some embodiments, a method of measuring a concentration of an analyte using a waveguide chip is provided. The method can include adding a known amount of a first detection molecule labelled with a first fluorescent tag to the sample, the first detection molecule specific to the analyte; introducing the sample to an array of sensing sites on the waveguide chip, each sensing site of the array having a first capture molecule specific to the analyte and a second capture molecule specific to the normalizing moiety, wherein the first capture molecule and the second capture molecule are both immobilized in each sensing site of the array at a predetermined ratio; introducing a first light pulse into one or more excitation waveguides on the waveguide chip at a first predetermined interval, the one or more excitation waveguides in optical communication with the array of sensing sites; measuring the fluorescence emitted by the first detection molecule through a plurality of collection waveguides in optical communication with the array of sensing sites; introducing a known amount of a normalizing moiety with a known amount of a second detection molecule labelled with a second fluorescent tag to the array of sensing sites, the second detection molecule specific to the normalizing moiety; introducing a second light pulse into the one or more excitation waveguides on the waveguide chip at a second predetermined interval, the one or more excitation waveguides in optical communication with the array of sensing sites; measuring the fluorescence emitted by the second detection molecule through the plurality of collection waveguides; and normalizing the measured fluorescence emitted by the first detection molecule using the measured fluorescence emitted by the second detection molecule.

In some embodiments, the step of normalizing the measured fluorescence emitted by the first detection molecule includes dividing the measured fluorescence emitted by the first detection molecule by the measured fluorescence emitted by the second detection molecule.

In some embodiments, the step of normalizing the measured fluorescence emitted by the first detection molecule includes dividing the measured fluorescence emitted by the first detection molecule by an average of the measured fluorescence emitted by the second detection molecule.

In some embodiments, the first predetermined interval is the same as the second predetermined interval.

In some embodiments, the first predetermined interval is different than the second predetermined interval.

In some embodiments, the first light pulse and the second light pulse have the same wavelength.

In some embodiments, a method of measuring a concentration of an analyte using a waveguide chip is provided. The method can include adding a known amount of a first detection molecule labelled with a first fluorescent tag to the sample, the first detection molecule specific to the analyte; introducing the sample to an array of sensing sites on the waveguide chip, each sensing site of the array having an immobilized capture molecule specific to the analyte; introducing a first light pulse into one or more excitation waveguides on the waveguide chip at a first predetermined interval, the one or more excitation waveguides in optical communication with the array of sensing sites; measuring the fluorescence emitted by the first detection molecule through a plurality of collection waveguides in optical communication with the array of sensing sites; introducing a known amount of the analyte with a known amount of a second detection molecule labelled with a second fluorescent tag to the array of sensing sites, the second detection molecule specific to the analyte; introducing a second light pulse into the one or more excitation waveguides on the waveguide chip at a second predetermined interval, the one or more excitation waveguides in optical communication with the array of sensing sites; measuring the fluorescence emitted by the second detection molecule through the plurality of collection waveguides; and normalizing the measured fluorescence emitted by the first detection molecule using the measured fluorescence emitted by the second detection molecule.

In some embodiments, the step of normalizing the measured fluorescence emitted by the first detection molecule includes dividing the measured fluorescence emitted by the first detection molecule by the measured fluorescence emitted by the second detection molecule.

In some embodiments, the step of normalizing the measured fluorescence emitted by the first detection molecule includes dividing the measured fluorescence emitted by the first detection molecule by a slope of the measured fluorescence emitted by the second detection molecule.

In some embodiments, the step of normalizing the measured fluorescence emitted by the first detection molecule includes dividing a slope of the measured fluorescence emitted by the first detection molecule by a slope of the measured fluorescence emitted by the second detection molecule.

In some embodiments, the first light pulse and the second light pulse have the same wavelength.

BRIEF DESCRIPTION OF THE DRAWINGS

The novel features of the invention are set forth with particularity in the appended claims. A better understanding of the features and advantages of the present methods and compositions may be obtained by reference to the following detailed description that sets forth illustrative embodiments, in which the principles of our methods, compositions, devices and apparatuses are utilized, and the accompanying drawings of which:

FIG. 7E is a schematic side view of a detection system according to an embodiment of the invention including a scanning light source/detector chip, a piezoelectric bending actuator and a substrate.

FIG. 12C is a schematic of a passive scanning light source/detector chip of the invention according to another embodiment including optical in-coupling and out-coupling waveguides.

DETAILED DESCRIPTION

Figure 1:
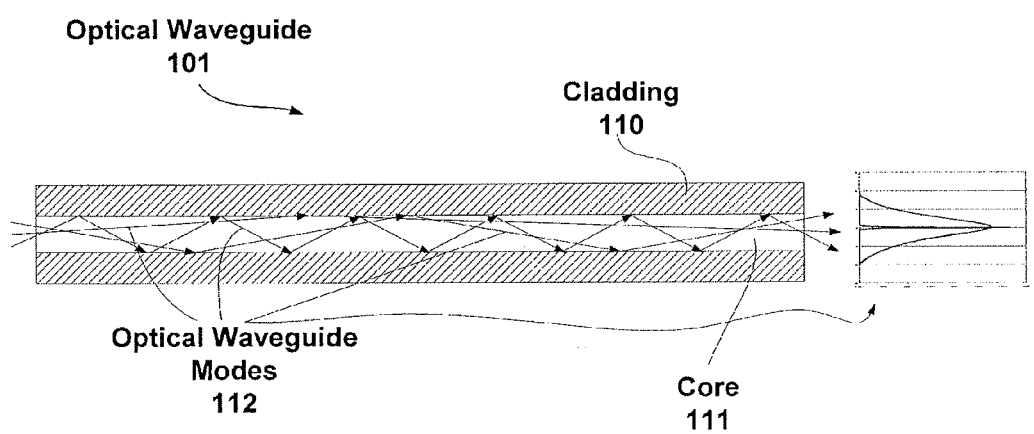
FIG. 1 is a schematic drawing of an optical waveguide.

The present invention provides methods and devices for coupling light of one or more wavelengths into one or more optical waveguides in a simple and cost-effective manner. Apparatus, methods, and kits for optical detection, using a detection system including a scanning light source, a detector, a substrate, and a plurality of waveguides and optical sensing sites are also provided. One substrate of the present system includes a plurality of substantially parallel excitation waveguides and a plurality of substantially parallel collection waveguides. The excitation waveguides and collection waveguides cross to form an intersection region and a two-dimensional array. Other substrates of the present system include a plurality of substantially parallel waveguides and a plurality of sensing sites. The optical sensing sites include a sensor and are in optical communication with one or more waveguides. Detection of a variety of environmental and biological samples can be achieved using the apparatus, methods and kits described herein. The general theoretical principles of lightwave guiding and evanescent field fluorescence excitation apply to the embodiments disclosed herein.

As used herein and in the appended claims, the singular forms "a," "an," and "the" include plural reference unless the context clearly indicates otherwise.

Unless defined otherwise, all technical and scientific terms used herein have the same meaning as commonly understood to one of ordinary skill in the art to which the inventions described herein belong. Although any methods, devices, and materials similar or equivalent to those described herein can be used in the practice or testing of the inventions described herein, the preferred methods, devices and materials are now described.

Definitions

The term "biologically active analyte" when used herein means any substance which can affect any physical or biochemical properties of a biological organism, including but not limited to viruses, bacteria, fungi, plants, animals, and humans. In particular as used herein, biologically active analyte according to the present invention includes without limitation drugs, prodrugs, pharmaceutical agents, drug metabolites, biomarkers such as expressed proteins and cell markers, antibodies, serum proteins, cholesterol, polysaccharides, nucleic acids, biological analytes, genes, proteins, or hormones, or any combination thereof. A biologically active analyte can further include a natural or man-made substance including but not limited to a gas, a chemical agent or a pollutant, or a combination thereof (e.g., from an environmental source). At a molecular level, the biologically active analytes can be polypeptide, glycoprotein, polysaccharide, lipid, nucleic acid, or a combination thereof.

Of particular interest are biomarkers associated with a particular disease or with a specific disease stage.

Such biologically active analytes include but are not limited to those associated with autoimmune diseases, obesity, hypertension, diabetes, neuronal and/or muscular degenerative diseases, cardiac diseases, endocrine disorders, and any combinations thereof.

Also of interest are biomarkers that are present in varying abundance in one or more of the body tissues including heart, liver, prostate, lung, kidney, bone marrow, blood, skin, bladder, brain, muscles, nerves, and selected tissues that are affected by various disease, such as different types of cancer (malignant or non-metastatic), autoimmune diseases, inflammatory or degenerative diseases.

Also of interest are biologically active analytes that are indicative of a microorganism. Exemplary microorganisms include but are not limited to bacterium, virus, fungus and protozoa. Biologically active analytes that can be detected by the subject method also include blood-born pathogens selected from a non-limiting group that consists of *Staphylococcus epidermidis, Escherichia coli*, methicillin-resistant *Staphylococcus aureus* (MSRA), *Staphylococcus aureus, Staphylococcus hominis, Enterococcus faecalis, Pseudomonas aeruginosa, Staphylococcus capitis, Staphylococcus warneri, Klebsiella pneumoniae, Haemophilus influnzae, Staphylococcus simulans, Streptococcus pneumoniae* and *Candida albicans*.

Biologically active analytes that can be detected by the subject device and methods also encompass a variety of sexually transmitted diseases selected from the following: gonorrhea (*Neisseria gorrhoeae*), syphilis (*Treponema pallidum*), chlamydia (*Chlamydia tracomitis*), nongonococcal urethritis (*Ureaplasma urealyticum*), yeast infection (*Candida albicans*), chancroid (*Haemophilus ducreyi*), trichomoniasis (*Trichomonas vaginalis*), genital herpes (HSV type I and II), HIV I, HIV II and hepatitis A, B, C, G, as well as hepatitis caused by TTV.

Additional biologically active analytes that can be detected by the subject apparatus and methods encompass a diversity of respiratory pathogens including but not limited to *Pseudomonas aeruginosa*, methicillin-resistant *Staphylococcus aureus* (MSRA), *Klebsiella pneumoniae, Haemophilis influenzae, Staphylococcus aureus, Stenotrophomonas maltophilia, Haemophilis parainfluenzae, Escherichia coli, Enterococcus faecalis, Serratia marcescens, Haemophilis parahaemolyticus, Enterococcus cloacae, Candida albicans, Moraxiella catarrhalis, Streptococcus pneumoniae, Citrobacter freundii, Enterococcus faecium, Klebsiella oxytoca, Pseudomonas fluorsecens, Neisseria meningitidis, Streptococcus pyogenes, Pneumocystis carinii, Klebsiella pneumoniae, Legionella pneumophila, Mycoplasma pneumoniae*, and *Mycobacterium tuberculosis*.

Listed below are additional exemplary markers according to the present invention: Theophylline, CRP, CKMB, PSA, Myoglobin, CA125, Progesterone, TxB2, 6-keto-PGF-1-alpha, and Theophylline, Estradiol, Lutenizing hormone, High sensitivity CRP, Triglycerides, Tryptase, Low density lipoprotein Cholesterol, High density lipoprotein Cholesterol, Cholesterol, IGFR.

Exemplary liver markers include without limitation LDH, (LD5), (ALT), Arginase 1 (liver type), Alphafetoprotein (AFP), Alkaline phosphatase, Alanine aminotransferase, Lactate dehydrogenase, and Bilirubin.

Exemplary kidney markers include without limitation TNFa Receptor, Cystatin C, Lipocalin-type urinary prostaglandin D, synthatase (LPGDS), Hepatocyte growth factor receptor, Polycystin 2, Polycystin 1, Fibrocystin, Uromodulin, Alanine, aminopeptidase, N-acetyl-B-D-glucosaminidase, Albumin, and Retinol-binding protein (RBP).

Exemplary heart markers include without limitation Troponin I (TnI), Troponin T (TnT), CK, CKMB, Myoglobin, Fatty acid binding protein (FABP), CRP, D-dimer, S-100 protein, BNP, NT-proBNP, PAPP-A, Myeloperoxidase (MPO), Glycogen phosphorylase isoenzyme BB (GPBB), Thrombin Activatable Fibrinolysis Inhibitor (TAFI), Fibrinogen, Ischemia modified albumin (IMA), Cardiotrophin-1, and MLC-I (Myosin Light Chain-I).

Exemplary pancreas markers include without limitation Amylase, Pancreatitis-Associated protein (PAP-1), and Regeneratein proteins (REG).

Exemplary muscle tissue markers include without limitation Myostatin.

Exemplary blood markers include without limitation Erythopoeitin (EPO).

Exemplary bone markers include without limitation, Cross-linked N-telopeptides of bone type I collagen (NTx), Carboxyterminal cross-linking telopeptide of bone collagen, Lysyl-pyridinoline (deoxypyridinoline), Pyridinoline, Tartrate-resistant acid phosphatase, Procollagen type I C propeptide, Procollagen type I N propeptide, Osteocalcin (bone gla-protein), Alkaline phosphatase, Cathepsin K, COMP (Cartilage Oligomeric Matrix Protein), Osteocrin, Osteoprotegerin (OPG), RANKL, sRANK, TRAP 5 (TRACP 5), Osteoblast Specific Factor 1 (OSF-1, Pleiotrophin), Soluble cell adhesion molecules, sTfR, sCD4, sCD8, sCD44, and Osteoblast Specific Factor 2 (OSF-2, Periostin).

In some embodiments markers according to the present invention are disease specific. Exemplary cancer markers include without limitation PSA (total prostate specific antigen), Creatinine, Prostatic acid phosphatase, PSA complexes, Prostrate-specific gene-1, CA 12-5, Carcinoembryonic Antigen (CEA), Alpha feto protein (AFP), hCG (Human chorionic gonadotropin), Inhibin, CAA Ovarian C1824, CA 27.29, CA 15-3, CAA Breast C1924, Her-2, Pancreatic, CA 19-9, Carcinoembryonic Antigen, CAA pancreatic, Neuron-specific enolase, Angiostatin. DcR3 (Soluble decoy receptor 3), Endostatin, Ep-CAM (MK-1), Free Immunoglobulin Light Chain Kappa, Free Immunoglobulin Light Chain Lambda, Herstatin, Chromogranin A, Adrenomedullin, Integrin, Epidermal growth factor receptor, Epidermal growth factor receptor-Tyrosine kinase, Pro-adrenomedullin N-terminal 20 peptide, Vascular endothelial growth factor, Vascular endothelial growth factor receptor, Stem cell factor receptor, c-kit/KDR, KDR, and Midkine.

Exemplary infectious disease markers include without limitation Viremia, Bacteremia, Sepsis, PMN Elastase, PMN elastase/α1-PI complex, Surfactant Protein D (SP-D), HBVc antigen, HBVs antigen, Anti-HBVc, Anti-HIV, T-suppressor cell antigen, T-cell antigen ratio, T-helper cell antigen, Anti-HCV, Pyrogens, p24 antigen and Muramyldipeptide.

Exemplary diabetes markers include without limitation C-Peptide, Hemoglobin A1c, Glycated albumin, Advanced glycosylation end products (AGEs), 1,5-anhydroglucitol, Gastric Inhibitory Polypeptide, Glucose, Hemoglobin, ANGPTL3 and ANGPTL 4.

Exemplary inflammation markers include without limitation Rheumatoid factor (RF), Antinuclear Antibody (ANA), C-reactive protein (CRP) and Clara Cell Protein (Uteroglobin).

Exemplary allergy markers include without limitation Total IgE and Specific IgE.

Exemplary autism markers include without limitation Ceruloplasmin, Metalothioneine, Zinc, Copper, B6, B12, Glutathione, Alkaline phosphatase, and Activation of apo-alkaline phosphatase.

Exemplary coagulation disorders markers include without limitation b-Thromboglobulin, Platelet factor 4 and Von Willebrand factor.

In some embodiments a marker may be therapy specific. COX inhibitors include without limitation TxB2 (Cox-1), 6-keto-PGF-1-alpha (Cox 2) and 11-Dehydro-TxB-1a (Cox-1).

Other markers of the present include without limitation Leptin, Leptin receptor, Procalcitonin, Brain S100 protein, Substance P and 8-Iso-PGF-2a.

Exemplary geriatric markers include without limitation, Neuron-specific enolase, GFAP and S100B.

Exemplary markers of nutritional status include without limitation Prealbumin, Albumin, Retinol-binding protein (RBP), Transferrin, Acylation-Stimulating Protein (ASP), Adiponectin, Agouti-Related Protein (AgRP), Angiopoietin-like Protein 4 (ANGPTL4, FIAF), C-peptide, AFABP (Adipocyte Fatty Acid Binding Protein, FABP4), Acylation-Stimulating Protein (ASP), EFABP (Epidermal Fatty Acid Binding Protein, FABP5), Glicentin, Glucagon, Glucagon-Like Peptide-1, Glucagon-Like Peptide-2, Ghrelin, Insulin, Leptin, Leptin Receptor, PYY, RELMs, Resistin, and sTfR (soluble Transferrin Receptor).

Exemplary markers of lipid metabolism include without limitation Apo-lipoproteins (several), Apo-A1, Apo-B, Apo-C-CII, Apo-D and Apo-E.

Exemplary coagulation status markers include without limitation Factor I: Fibrinogen, Factor II: Prothrombin, Factor III: Tissue factor, Factor IV: Calcium, Factor V: Proaccelerin, Factor VI, Factor VII: Proconvertin, Factor VIII: Anti-hemolytic factor, Factor IX: Christmas factor, Factor X: Stuart-Prower factor, Factor XI: Plasma thromboplastin antecedent, Factor XII: Hageman factor, Factor XIII: Fibrin-stabilizing factor, Prekallikrein, High-molecular-weight kininogen, Protein C, Protein S, D-dimer, Tissue plasminogen activator, Plasminogen, a2-Antiplasmin and Plasminogen activator inhibitor 1 (PAI1).

Exemplary monoclonal antibody markers include those for EGFR, ErbB2, and IGF1R.

Exemplary tyrosine kinase inhibitor markers include without limitation Abl, Kit, PDGFR, Src, ErbB2, ErbB 4, EGFR, EphB, VEGFR1-4, PDGFRb, FLt3, FGFR, PKC, Met, Tie2, RAF, and TrkA.

Exemplary serine/threonine kinase inhibitor markers include without limitation AKT, Aurora A/B/B, CDK, CDK (pan), CDK1-2, VEGFR2, PDGFRb, CDK4/6, MEK1-2, mTOR, and PKC-beta.

GPCR target markers include without limitation Histamine Receptors, Serotonin Receptors, Angiotensin Receptors, Adrenoreceptors, Muscarinic Acetylcholine Receptors, GnRH Receptors, Dopamine Receptors, Prostaglandin Receptors, and ADP Receptors.

For the purposes of this invention, a "therapeutic agent" is intended to include any substances that have therapeutic utility and/or potential. Such substances include but are not limited to biological or chemical compounds such as simple or complex organic or inorganic molecules, peptides, proteins (e.g. antibodies) or polynucleotides (e.g. anti-sense). A vast array of compounds can be synthesized, for example, polymers, such as polypeptides and polynucleotides, and synthetic organic compounds based on various core structures, and these are also included in the term "therapeutic agent". In addition, various natural sources can provide compounds for screening, such as plant or animal extracts, and the like. It should be understood, although not always explicitly stated, that the agent is used alone or in combination with another agent, having the same or different biological activity as the agents identified by the inventive screen. The agents and methods also are intended to be combined with other therapies.

Pharmacodynamic (PD) parameters according to the present invention include without limitation physical parameters such as temperature, heart rate/pulse, blood pressure, and respiratory rate, and biomarkers such as proteins, cells, and cell markers. Biomarkers could be indicative of disease or could be a result of the action of a drug. Pharmacokinetic (PK) parameters according to the present invention include without limitation drug and drug metabolite concentration. Identifying and quantifying the PK parameters rapidly from a sample volume is extremely desirable for proper safety and efficacy of drugs. If the drug and metabolite concentrations are outside a desired range and/or unexpected metabolites are generated due to an unexpected reaction to the drug, immediate action may be necessary to ensure the safety of the patient. Similarly, if any of the PD parameters fall outside the desired range during a treatment regime, immediate action may have to be taken as well.

In preferred embodiments physical parameter data is stored in or compared to stored profiles of physical parameter data in a bioinformatics system which may be on an external device incorporating pharmacogenomic and pharmacokinetic data into its models for the determination of toxicity and dosing. Not only does this generate data for clinical trials years prior to current processes but also enables the elimination of current disparities between apparent efficacy and actual toxicity of drugs through real-time continuous monitoring. During the go/no go decision process in clinical studies, large scale comparative population studies can be conducted with the data stored on the database. This compilation of data and real-time monitoring allows more patients to enter clinical trials in a safe fashion earlier than currently allowed. In another embodiment biomarkers discovered in human tissue studies can be targeted by the detection system for improved accuracy in determining drug pathways and efficacy in cancer studies.

The term "nucleic acid" when used herein refers to deoxyribonucleotides, deoxyribonucleosides, ribonucleosides or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless specifically limited otherwise, the term also refers oligonucleotide analogs including PNA (peptidonucleic acid), analogs of DNA used in antisense technology (phosphorothioates, phosphoroamidates, and the like). Unless otherwise indicated, a particular nucleic acid sequence also implicitly encompasses conservatively modified variants thereof (including but not limited to, degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Rossolini et al., *Mol. Cell. Probes* 8:91-98 (1994)).

The term "microorganism" when used herein refers to bacteria, actinomycetales, cyanobacteria (unicellular algae), fungi, protozoa, animal cells or plant cells or viruses. Examples of microorganisms include but are not limited to pathogens.

The terms "polypeptide," "peptide" and "protein" are used interchangeably herein to refer to a polymer of amino acid residues. That is, a description directed to a polypeptide applies equally to a description of a peptide and a description of a protein, and vice versa. The terms apply to naturally occurring amino acid polymers as well as amino acid polymers in which one or more amino acid residues is a non-natural amino acid. As used herein, the terms encompass amino acid chains of any length, including full length proteins (i.e., antigens), wherein the amino acid residues are linked by covalent peptide bonds. In addition, proteins that contain multiple polypeptide chains that associate through covalent and/or non-covalent interactions are also encompassed by "protein," as used herein.

The term "polymorphism" as used herein refers to the occurrence of two or more genetically determined alternative sequences or alleles in a population. A polymorphic marker or site is the locus at which divergence occurs. Preferred markers have at least two alleles, each occurring at a frequency of greater than 1%, and more preferably greater than 10% or 20% of a selected population. A polymorphism may comprise one or more base changes, an insertion, a repeat, or a deletion. A polymorphic locus may be as small as one base pair. Polymorphic markers include restriction fragment length polymorphisms, variable number of tandem repeats (VNTR's), hypervariable regions, minisatellites, dinucleotide repeats, trinucleotide repeats, tetranucleotide repeats, simple sequence repeats, and insertion elements such as Alu. The first identified allelic form is arbitrarily designated as the reference form and other allelic forms are designated as alternative or variant alleles. The allelic form occurring most frequently in a selected population is sometimes referred to as the wildtype form. Diploid organisms may be homozygous or heterozygous for allelic forms. A diallelic polymorphism has two forms. A triallelic polymorphism has three forms.

A single nucleotide polymorphism (SNP) occurs at a polymorphic site occupied by a single nucleotide, which is the site of variation between allelic sequences. The site is usually preceded by and followed by highly conserved sequences of the allele (e.g., sequences that vary in less than 1/100 or 1/1000 members of the populations).

A single nucleotide polymorphism usually arises due to substitution of one nucleotide for another at the polymorphic site. A transition is the replacement of one purine by another purine or one pyrimidine by another pyrimidine. A transversion is the replacement of a purine by a pyrimidine or vice versa. Single nucleotide polymorphisms can also arise from a deletion of a nucleotide or an insertion of a nucleotide relative to a reference allele.

The term "individual" when used herein is not limited to a human being, but may also include other organisms including but not limited to mammals, plants, bacteria or cells derived from any of the above.

The term "about" or "approximately" as used herein can mean within 10, 20, or 30 percent.

Aspects of the invention may include one or more of the following advantageous features. Dense and accurate integration of optical manipulating elements can be achieved using planar lightwave circuit technology. Applications for planar lightwave circuits as described herein include new drug discovery and development, disease research, biomarkers discovery, detection of a chemical or biological warfare agent, environmental monitoring, SNP association studies including toxicology and disease susceptibility, and diagnostics including identifying patients predisposed to diseases and identifying patients with particular drug sensitivity.

"Optical coupling" from one element to another (e.g. a light emitter to an optical waveguide) occurs whenever there is some overlap between the "optical modes" of the two elements. The "optical mode" of an element, as defined herein, represents the spatial and temporal behavior of the light emitted from or accepted by that element.

In the current invention one or more light sources or alternatively, their emitted light beams, are spatially translated relative to one or more optical waveguides with the optical modes of the light sources scanning through space to overlap at some arbitrary time and arbitrary place with some of the optical modes of one or more optical waveguides. During that overlap, light is coupled from the overlapping optical mode of a light source to the overlapping optical mode of an optical waveguide, thereby generating a light pulse within the optical waveguide, which pulse has a duration equal to the overlapping time and a wavelength equal to that of the overlapping light source.

By "spatially translated relative to the optical waveguide" is meant that either the light sources are physically translated through space, or their emitted light beams are translated using optical means (e.g. lenses, prisms, mirrors, etc.) or the optical waveguides are physically translated through space, until the overlap of the optical modes occurs.

An apparatus which utilizes this method of generating an optical pulse using a spatially scanning light beam is referred to herein as the "scanning-coupling system" of the invention.

A general optical waveguide 101 is depicted in FIG. 1. It consists of two main regions, the core region 111 and the cladding region 110. Light is confined and propagates along a waveguide in the core region. This confinement is most commonly achieved by designing the core region to have an index of refraction higher than that of the cladding region. Thus light 'trying to escape' the core region experiences 'total internal reflection' and remains trapped in the core region. Only light having certain properties (e.g., propagation angle) is trapped within the core region. Every optical waveguide has a discrete set of "modes" having those properties and thus able to propagate along the waveguide. These are referred to as the "optical modes" of the waveguide 112.

Figure 2A:
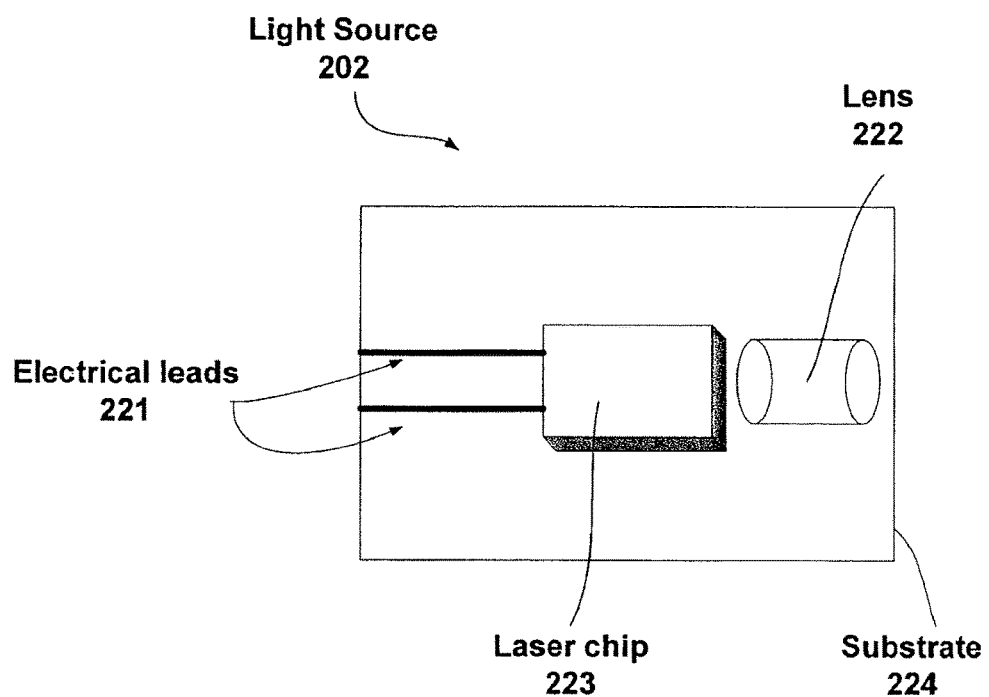
FIG. 2A is a schematic drawing illustrating one possible configuration of a light source for use in the invention.

A representative light source 202 is schematically shown in FIG. 2A. The light source consists of a laser chip 223 and the electrical leads 221 for driving it. Although lasers are the most common source for coupling light into a waveguide, in some cases a Light Emitting Diode (LED) may be used. A lens 222 in the drawing represents a variety of optical components that can be used to manipulate (i.e. collimate, focus, filter, deflect, etc.) the emitted light. All these components can be assembled in a compact way on a single or on multiple substrates 224.

Figure 2B:
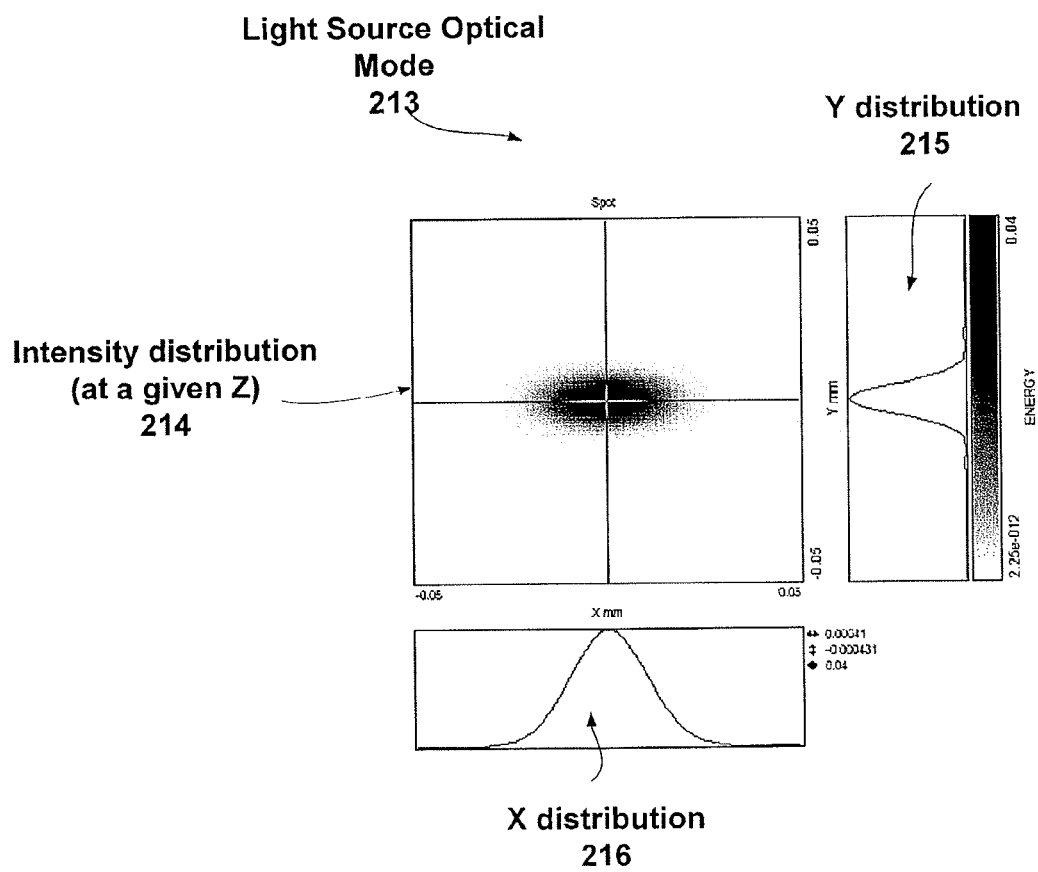
FIG. 2B is a graph illustrating a typical light source optical mode.

Such a light source is connected to its driving electronics which control the way it operates to generate a continuous wave (CW) of light or pulses. The light source generates light in one or in several different wavelengths. In some cases, the wavelength of the light emitted by the light source can be tuned by changing its temperature or by placing a filter in front of the light source to pick one wavelength out of the emitted spectrum. The light emitted by the light source and passing through the lens (and/or other optical components) has a certain intensity distribution and propagation angles, referred to herein as the light source "optical mode". FIG. 2B shows an example of a light source optical mode 213, its intensity distribution 214 at a given distance (Z), its Y distribution 215 and its X distribution 216.

In embodiments of the present invention, a pulse of light from the light source is coupled to the optical waveguide by moving the one relative to the other through a point where there is some overlap between the optical modes of the two, resulting in the generation of an optical pulse within the optical waveguide. Repeating the same process with the same light source and optical waveguide generates a train of identical light pulses. Repeating the same process with different light sources generates a train of pulses differing in wavelength, and/or duration and/or any other property of the light emitted by the light sources (e.g., intensity, temporal coherence, spatial coherence, or amplitude modulation). Repeating the scanning process with multiple light sources and multiple optical waveguides generates correlated trains of pulses in all or some of the optical waveguides.

The generated pulse will be a convolution in space of the two optical modes of the light source and the optical waveguide. This convolution is affected by both of the optical modes and their spatial and temporal overlap. The resulting pulse is also affected by the size of the two beams. The scanning speed also affects the generated pulse through the temporal dependence of the moving optical mode. If the waveguide has more than one mode the resulting pulse will be a sum of all overlaps.

The pulse duration may be more simply calculated by taking the effective beam diameter of the light source and that of the waveguide. The approximate pulse duration is the sum of these two beam diameters divided by the scanning amplitude, multiplied by the scanning period.

There are many possible means for achieving the relative movement of the one or more light sources or their emitted light beams with respect to the one or more optical waveguides. These means may include mechanisms such as, for example, a rotating disk, a motor, a solenoid, a hydraulic mechanism, a piezo-electric mechanism, and a "memory-metal" mechanism. In addition, the relative motion may be generated through simple manually driven actuators. Either the light sources or the optical waveguides may be physically translated through space. Alternatively, the light sources may be stationary while the light beams emitted from the light sources are translated using optical means (e.g. lenses, prisms, mirrors, etc.). Spatial translation of the optical means may be achieved using any of the above described means.

Various non-limiting embodiments of the optical coupling methods and devices of the invention are described below.

Figure 3A:
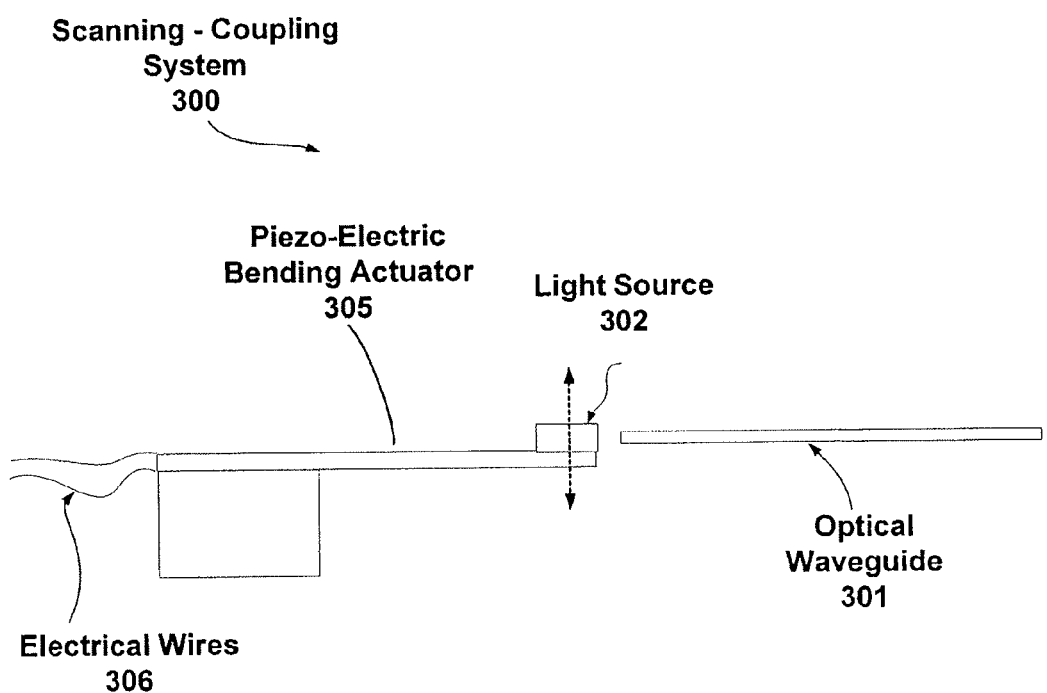
FIG. 3A is a schematic drawing of an embodiment of a scanning-coupling system according to the invention.

In one embodiment of the invention, the light source 302 is mounted on a piezoelectric bending actuator 305 as shown in FIG. 3A. The scanning-coupling system 300 comprises an optical waveguide 301. The piezoelectric bending actuator driver (not shown) interfaces to the actuator through electrical wires 306. The driver generates the required voltage to run the actuator. This voltage may be in the form of a 'Saw-Tooth' wave, or a 'Sine' wave or a 'Square' wave or any other form of electrical wave that would cause the piezoelectric bending actuator to bend up and/or down, thus moving the light source relative to the optical waveguide. Somewhere along the path of the light source, an overlap occurs between the optical mode of the light source and the optical mode of the optical waveguide, thereby generating a pulse of light traveling in the optical waveguide.

The duration of the pulse is equal to the overlap time of the two optical modes. The duration of the pulse may be controlled either by changing one of the optical modes or by adjusting the scanning speed. The optical mode of the light source can be controlled by, for example, moving the lens in front of the emitter (see FIG. 2A) away or closer, thus expanding or converging the emitted light beam (i.e. the optical mode).

For example, in a system comprising a light source with a Gaussian shaped optical mode of 10 microns in width, and an optical waveguide with a Gaussian shaped optical mode of 1 micron in width, the width of the overlap of the two optical modes will be a convolution of the two, resulting in a Gaussian shaped optical mode of ~10-microns in width. If the piezoelectric bending actuator is driven with a periodic 'Saw-Tooth' wave having a frequency of 100 Hz with a scanning amplitude of 300 microns, the result is a 167 micro second pulse generated in the optical waveguide once every 5 milliseconds.

As with any other mechanical system, the piezoelectric bending actuator has limitations on its scanning speed. The components of the scanning-coupling system of the invention are therefore selected or designed to be able to meet the required scanning speed for a specific application. The current invention may be particularly advantageous in applications where the duration of the light pulses involved is of the order of a micro ($10^{-6}$) second or longer.

Figure 3B:
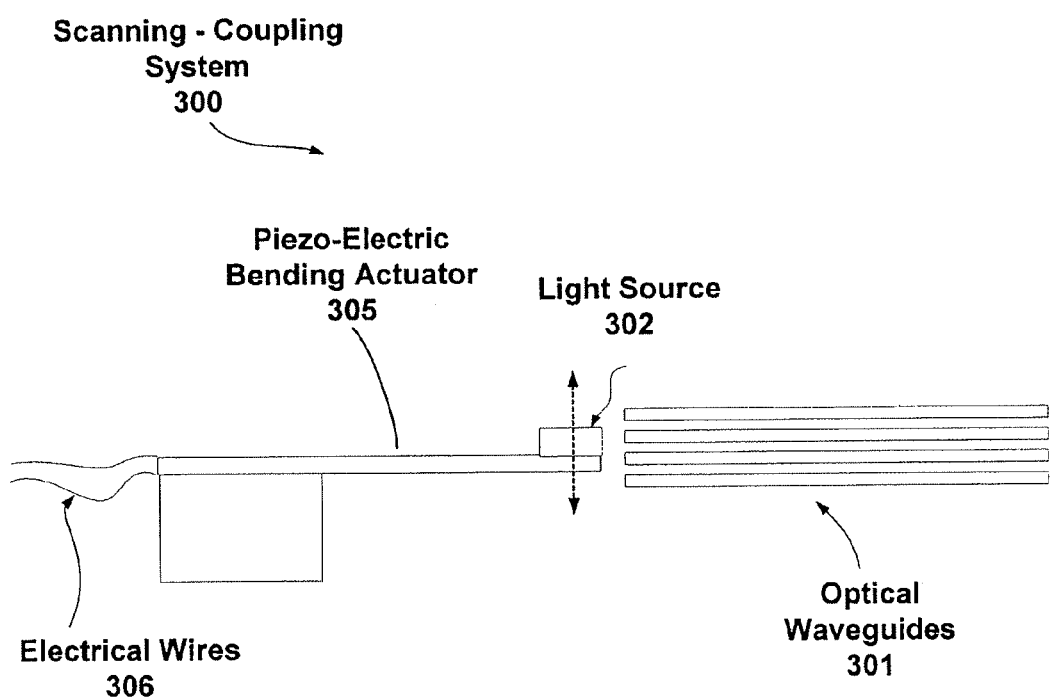
FIG. 3B is a schematic drawing of a second embodiment of a scanning-coupling system according to the invention including multiple optical waveguides.

A further embodiment of the invention is shown in FIG. 3B, where the scanning-coupling system 300 consists of the piezoelectric bending actuator 305 and its electrical wires 306, the light source 302 and multiple optical waveguides 301. The scanning light source will now generate trains of pulses in some or all of the optical waveguides based upon the chosen scanning path.

Figure 3C:
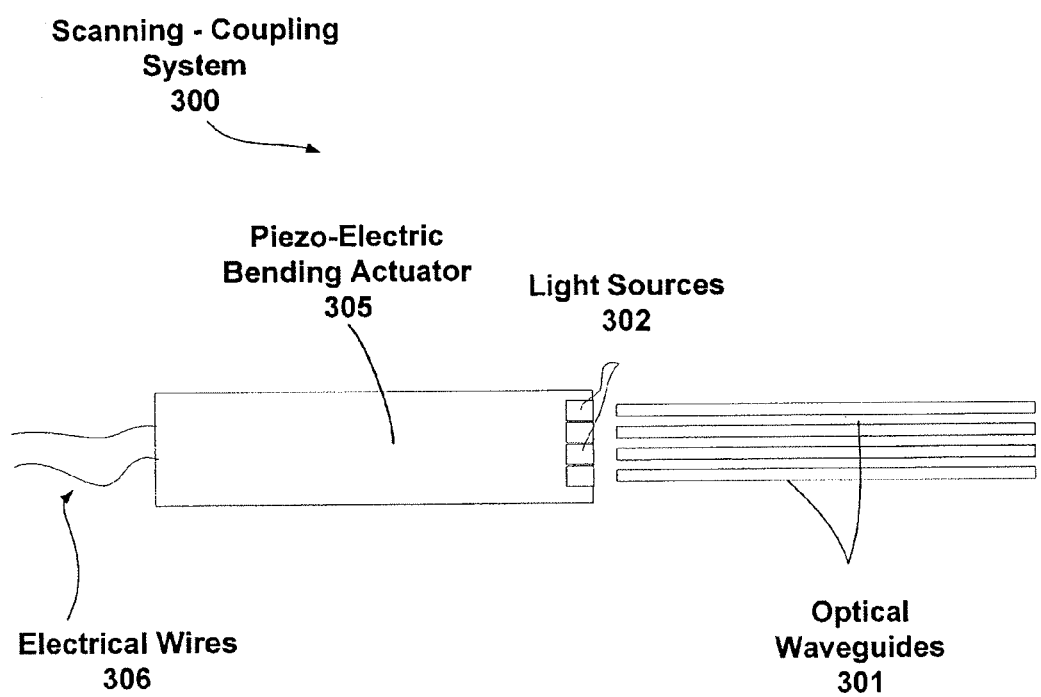
FIG. 3C is a schematic drawing of a third embodiment of a scanning-coupling system according to the invention including multiple light sources and multiple optical waveguides.

A further embodiment of the invention is shown in FIG. 3C. The scanning-coupling system 300 comprises multiple light sources 302, multiple optical waveguides 301, a piezoelectric bending actuator 305 and its electrical wires 306. By selecting the properties of the different light sources (for example, their wavelength or optical mode.), it is possible to generate in each of the optical waveguides a train of pulses at many different wavelengths and with varying duration.

Figure 4A:
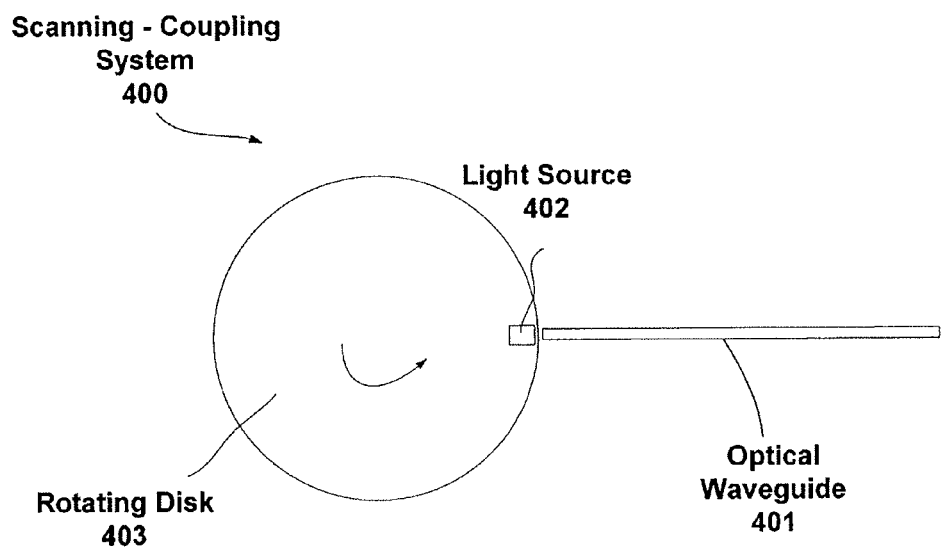
FIG. 4A is a schematic drawing of a fourth embodiment of a scanning-coupling system according to the invention including a rotating disk.

In a further embodiment depicted in FIG. 4A, the light source 402 is mounted on a rotating disk 403 to create a scanning-coupling system 400. The system further comprises an optical waveguide 401. The rotating disk is driven by an electronic driver (not shown) causing the light source optical mode to scan the periphery of the disk through a point where it overlaps the optical mode of an optical waveguide. During this overlap, a light pulse is generated in the optical waveguide, the duration of which is equal to the duration of the overlap. In this case, the pulse duration is controlled by the shape of the two optical modes and the rotating speed of the disk.

Figure 4B:
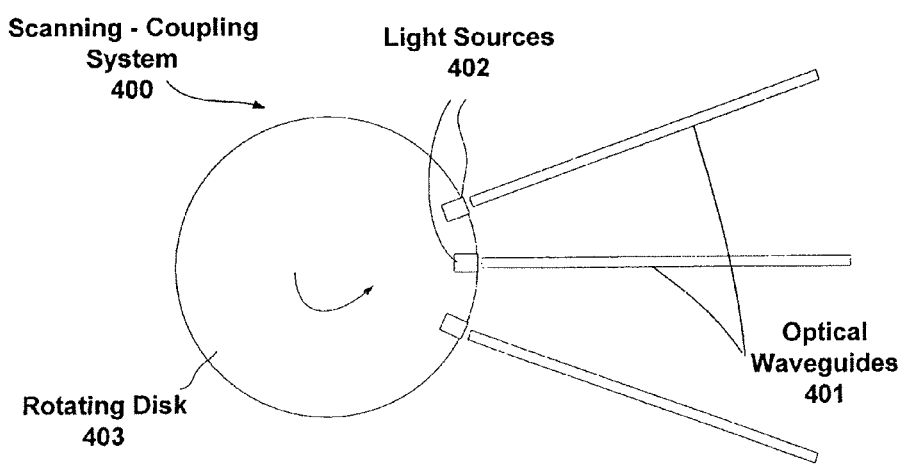
FIG. 4B is a schematic drawing of a fifth embodiment of a scanning-coupling system according to the invention including a rotating disk, multiple light sources and multiple optical waveguides.

A further embodiment of the scanning-coupling system 400 is shown in FIG. 4B. Multiple light sources 402 are mounted on a disk 403 facing outwards, with multiple optical waveguides 401 placed around the disk facing inwards. The time between two adjacent pulses in the same optical waveguide is controlled by the spacing between the light sources, as well as the rotation speed of the disk. There is also a well defined time correlation between the trains of pulses in all the optical waveguides.

Figure 5:
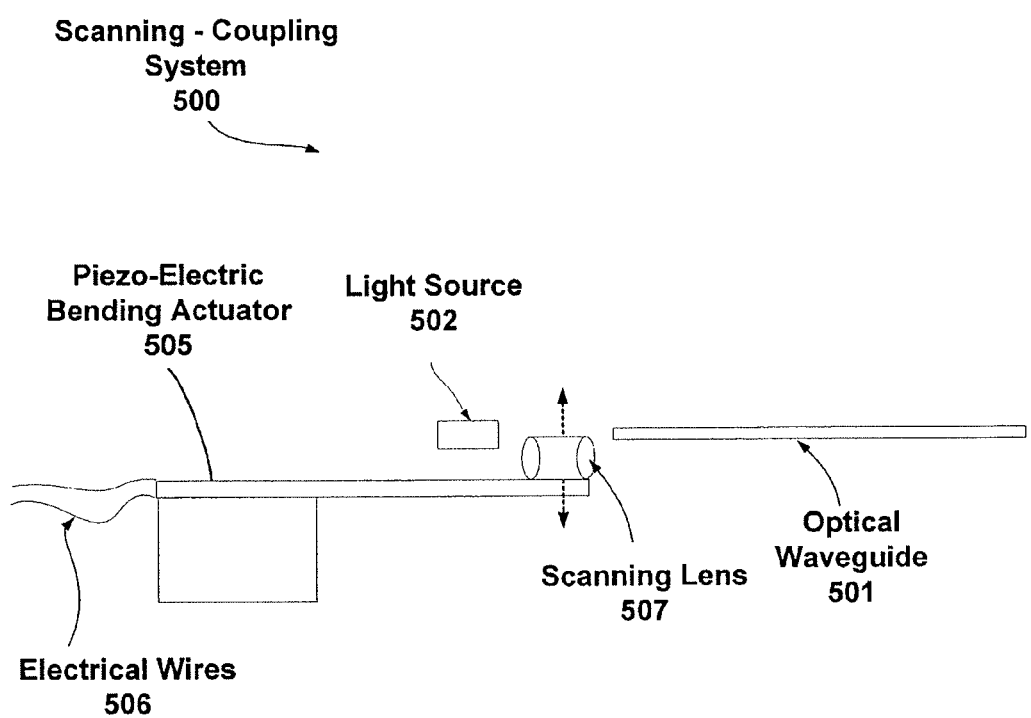
FIG. 5 is a schematic drawing of a sixth embodiment of a scanning-coupling system according to the invention including a scanning lens.

In yet a further embodiment schematically shown in FIG. 5, the scanning-coupling system 500 consists of a piezo-electric bending actuator 505 and its electrical wires 506, mounted with a scanning lens 507. In this embodiment of the invention, the light source 502 and the optical waveguide 501 are fixed. The scanning of the light beam emitted by the light source is achieved by moving the lens in front of the light source. The lens is disposed between the light source and the optical waveguide effective that movement of the actuator causes a light beam emitted by the light source to be directed by the lens effective to cause an overlap between the optical modes of the light beam and the optical waveguide.

Figure 6:
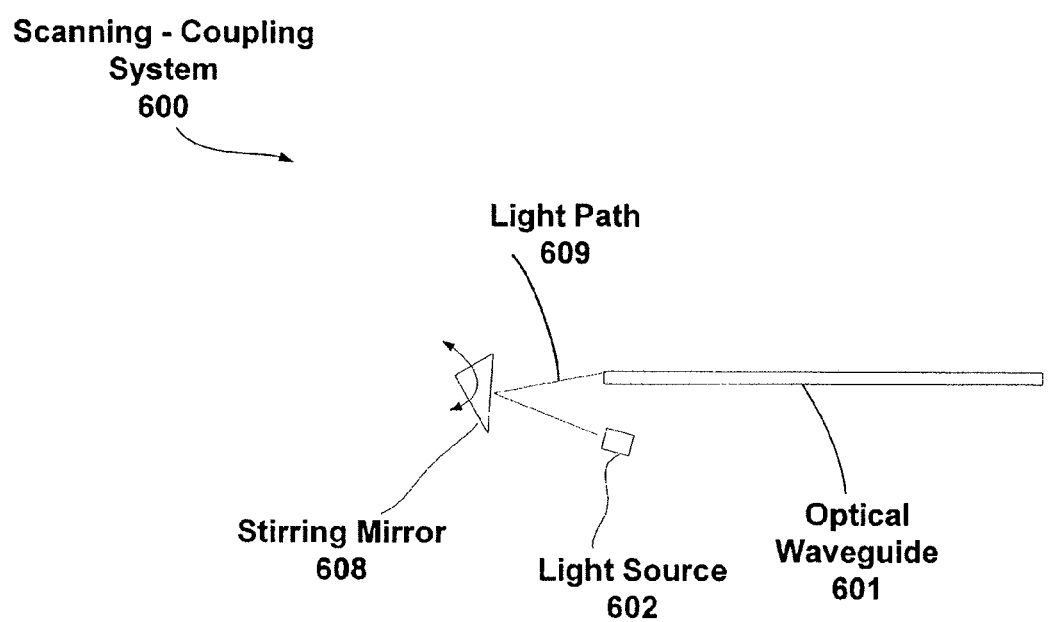
FIG. 6 is a schematic drawing of a seventh embodiment of a scanning-coupling system according to the invention including a stirring mirror.

FIG. 6 shows yet another non-limiting example of the scanning-coupling system 600 where a stirring mirror 608 serves to deflect the light beam from light source 602 to scan space until it overlaps the 'optical mode' of optical waveguide 601. The light path 609 at one specific instant is also shown. The movement of the stirring mirror may be effected by any of the means disclosed herein, including, for example, a rotating disk, a motor, a solenoid, a hydraulic mechanism, a piezo-electric mechanism, a "memory-metal" mechanism, or a manually driven actuator.

In all of the above embodiments, the light source can be controlled by turning it 'on' and 'off' at chosen time periods, thus controlling which of the potential pulses is actually generated while the light sources are scanning through the optical waveguides. Furthermore, it should be understood that the scanning of the light source or its emitted light beam can be periodic, by constantly running the scanner in a periodic fashion, or it can be operated 'on demand,' generating anything from a single pulse to a large number of pulses.

Figure 8:
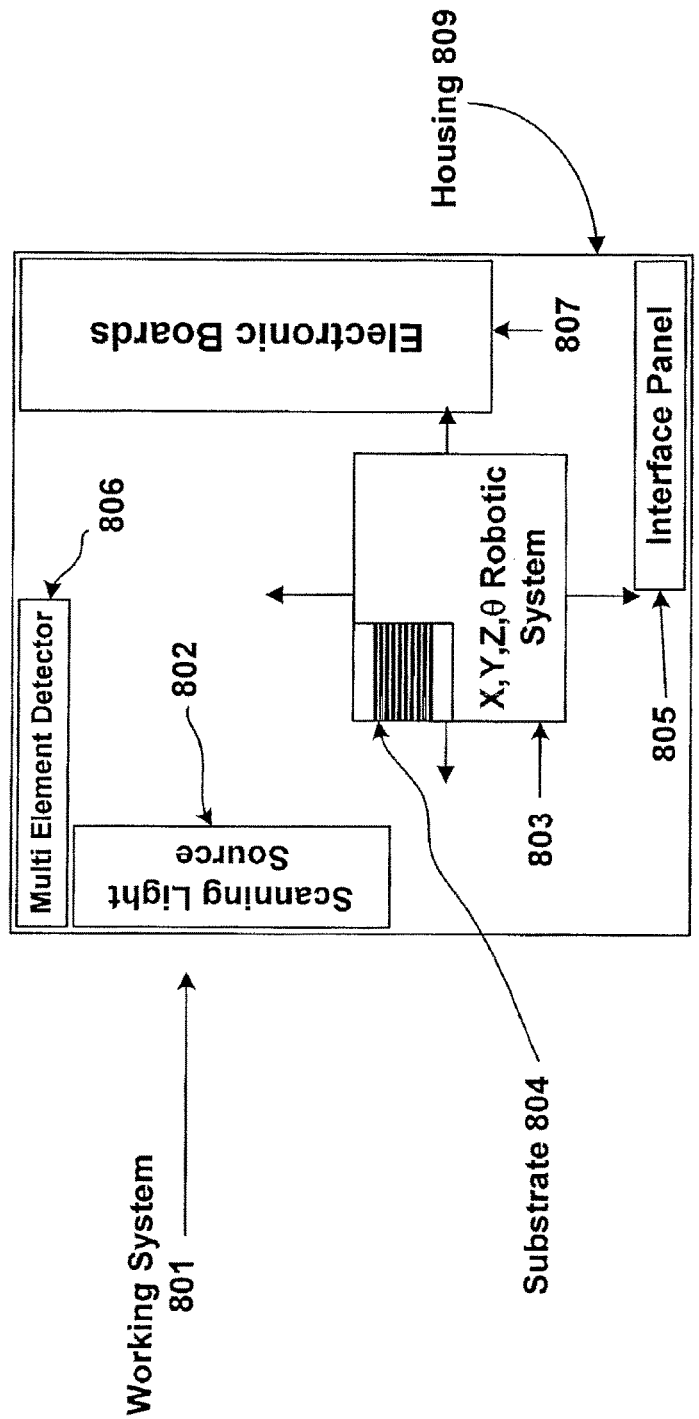
FIG. 8 is a block diagram showing a representative example of a detection system of the invention in a housing as part of a working system.

The invention further comprises optical detection systems which utilize any of the scanning-coupling devices and methods described above. Additional components of such optical detection systems may include, for example, substrates for sample binding and/or processing, thermal transfer elements, thermistors, microchannels, reservoirs, electronic control boards, sample handling systems, an interface panel, and an enclosure or housing. FIG. 8 is a block diagram of a detection system representing one possible system where the scanning-coupling systems of the current invention may be used. Particular optical scanning systems where the scanning-coupling systems of the current invention are especially useful are described in U.S. Patent Publication Nos. 20070211985, published Sep. 13, 2007, and 20090068668, published Mar. 12, 2009.

In various embodiments, the detection systems of the invention include a scanning light source and a substrate comprising a plurality of waveguides. The scanning light source emits one or more light beams that are spatially translated relative to the waveguides of the substrate such that the light beam is coupled to and in optical communication with the waveguides of the substrate at some point along its scanning path. By "spatially translated relative to the waveguides of the substrate" is meant that either the scanning light source is physically translated through space, or that the substrate comprising the waveguides is physically translated through space.

In various embodiments, the scanning light source is a chip referred to herein as a "scanning light source chip." In embodiments where the scanning light source further includes detector elements, it may be referred to herein as a "scanning light source/detector," or a "scanning light source/detector chip." The scanning light source chips and scanning light source/detector chips of the invention are further referred to herein as "active scanning" chips in embodiments where the light generating elements (and detector elements when present) are integral to the chip, and as "passive scanning" chips in embodiments where the light generating elements (and detector elements when present) are external to the chip. The general term "scanning light source" may be used herein to encompass any or all of these embodiments of scanning light source chips and scanning light source/detector chips. Exemplary embodiments of systems of the invention including each of these types of scanning light source are described below.

Figure 7A:
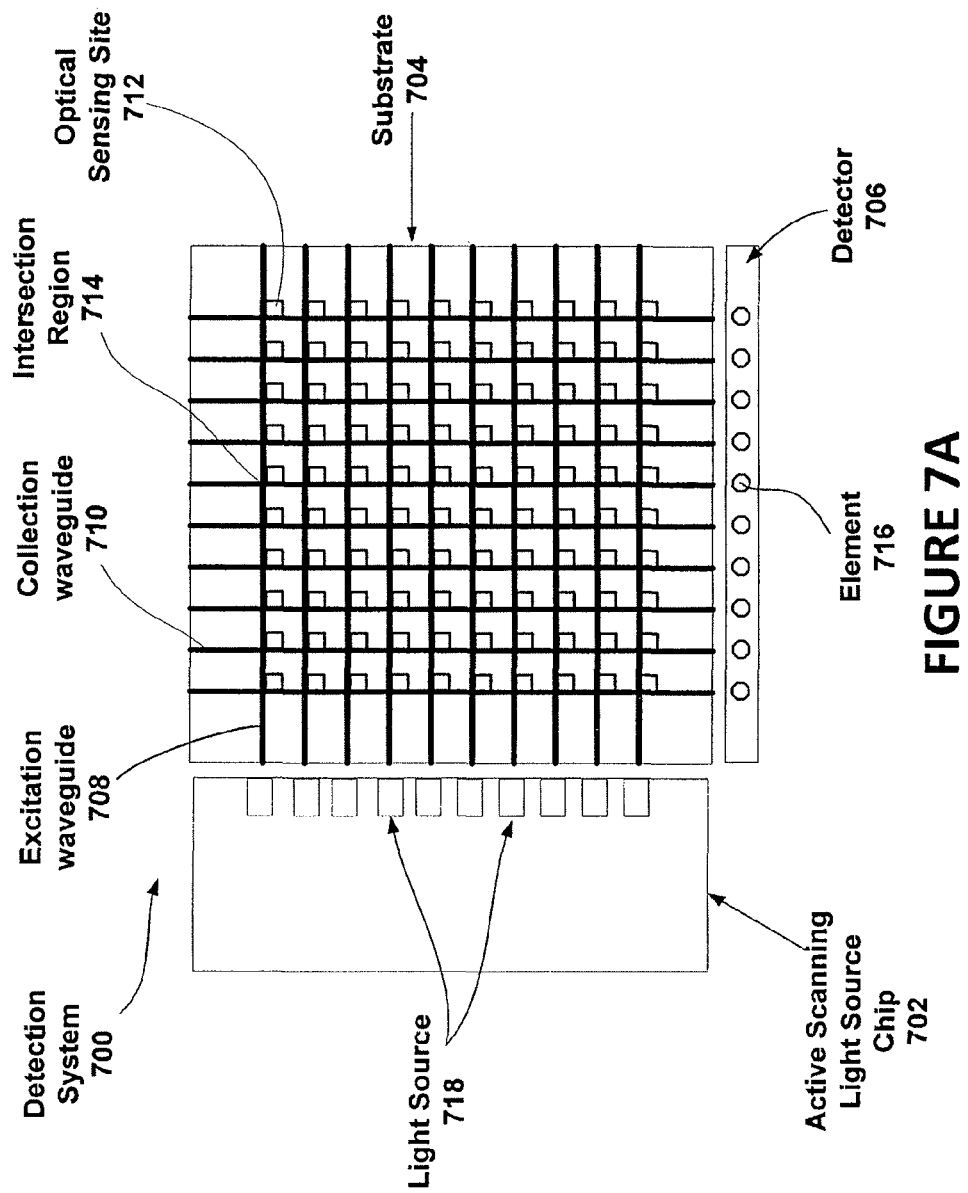
FIG. 7A is a schematic of a detection system according to one embodiment of the invention including an active scanning light source chip, a substrate, a detector, and optical sensing sites.

FIG. 7A illustrates an exemplary detection system 700 of the invention including an active scanning light source chip 702, a substrate 704, optical sensing sites 712 and a detector 706. The substrate includes excitation waveguides 708 and collection waveguides 710 that cross or intersect at an intersection region 714.

In one embodiment, as shown in FIG. 7A, the active scanning light source chip 702 is at some point along its scanning path coupled to and in optical communication with one or more of the excitation waveguides 708 at a first edge of the substrate 704. Additionally, the detector 706 is coupled to and in optical communication with one or more of the collection waveguides 710 at a second edge of the substrate 704. Although a single detector at one edge of the substrate is shown, it is envisioned that two or more detectors could be coupled to and in optical communication with one or more collection waveguides or excitation waveguides at various edges of the substrate (not shown). For example, in one embodiment, where the active scanning light source chip is coupled to a first edge of the substrate, a first detector could be coupled to an adjacent edge and be in optical communication with a first end of a collection waveguide, while a second detector could be coupled to another adjacent edge and be in optical communication with a second end of a collection waveguide. A third detector can be coupled to the edge opposite to the one coupled to the active scanning light source chip and be in optical communication with the second end of the excitation waveguides (not shown).

As shown in FIG. 7A, in one embodiment the system 700 can be substantially planar. For example, the active scanning light source chip 702 can be a planar chip. This can be coupled to a planar substrate 704 that is a second chip that is further coupled to a planar detector 706 that is a third chip. In a particular embodiment, as shown in FIG. 7A, the system 700 is a planar lightwave circuit including three coupled chips. In one embodiment two chips are integrated into a single chip (e.g., the substrate chip and the detector chip). Such a configuration would be useful in a case where the substrate chip is reusable and can be effectively used for long periods of time. One application of such a configuration would be in a system for detecting biological warfare-associated agents. In such an application it would be advantageous for the system to operate for long periods of time without a need for replacing the chip. In addition, having two chips integrated on a single substrate solves the problem of maintaining the relative alignment of two chips Where the system is used in biological applications, including but not limited to detection of biologically active analytes including nucleic acids, proteins or microorganisms, the substrate can be a multi-element bio-analysis chip.

Figure 7B:
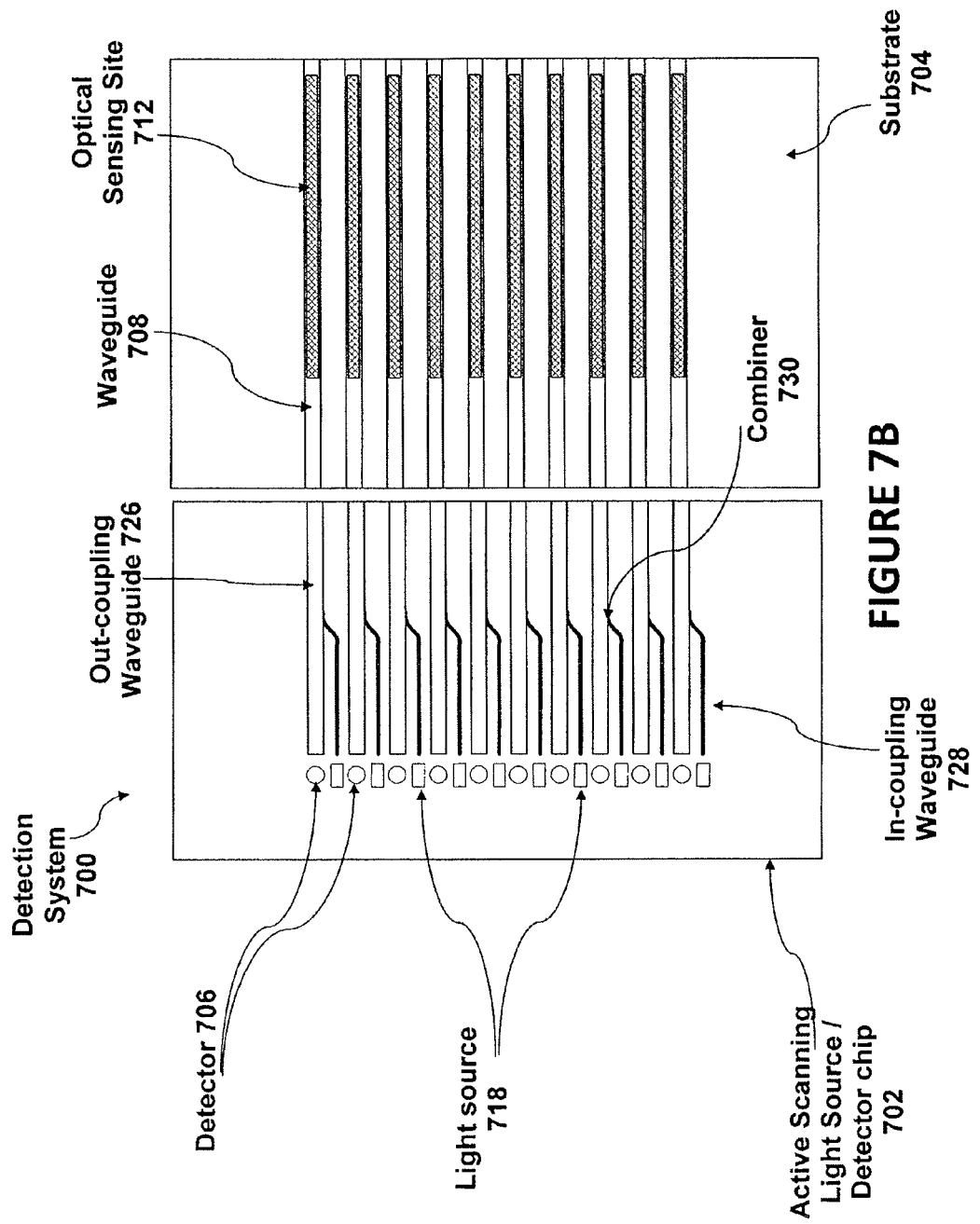
FIG. 7B is a schematic of a detection system according to another embodiment of the invention including an active scanning light source/detector chip, a substrate and optical sensing sites.
Figure 7C:
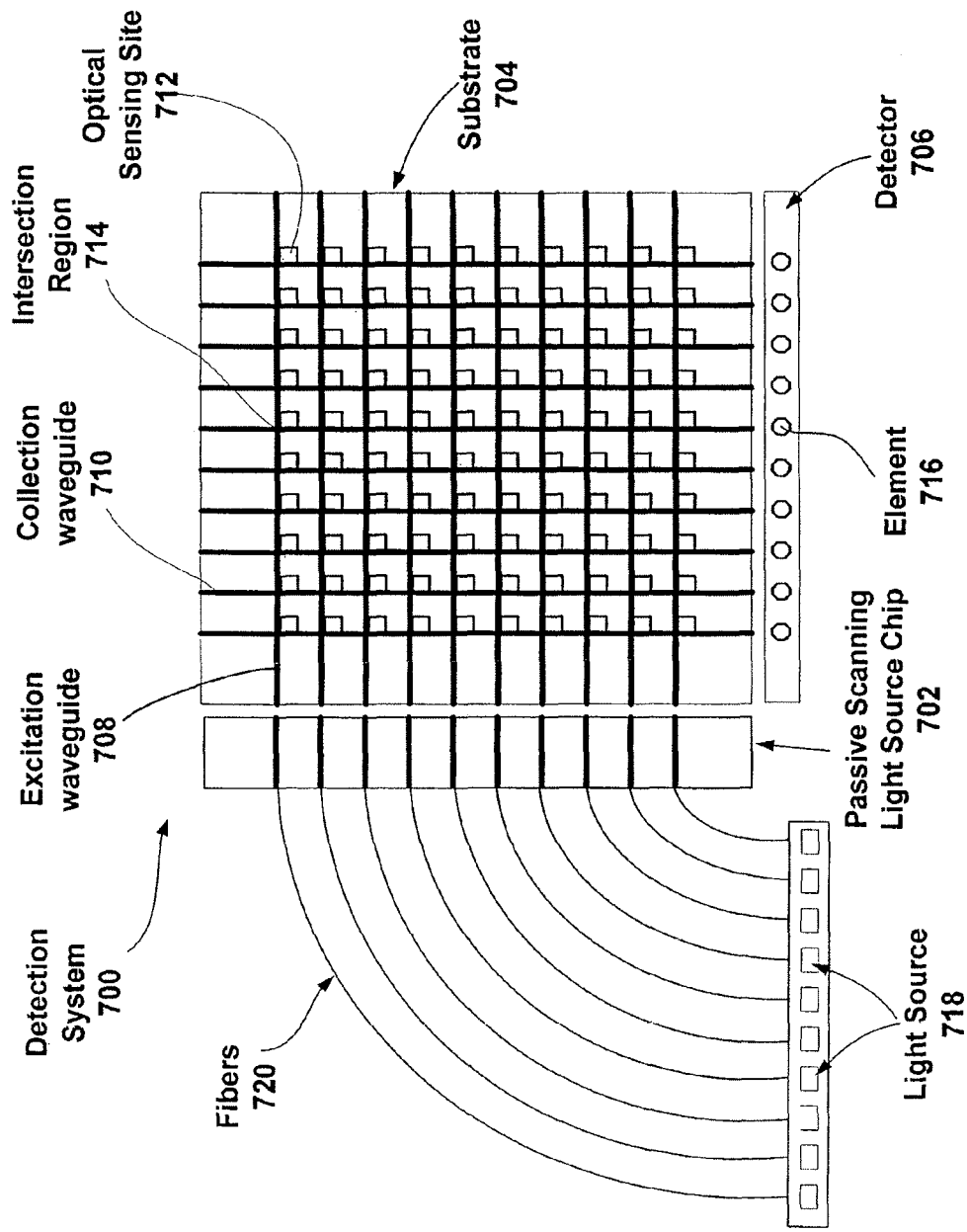
FIG. 7C is a schematic of a detection system according to another embodiment of the invention including a light source, fibers, a passive scanning light source chip, a substrate, optical sensing sites and a detector.

In the embodiments of FIGS. 7A and 7C, it is envisioned that the crossing or intersecting of the excitation waveguides and the collection waveguides can be a direct physical crossing or intersecting, for example, where the excitation waveguides and the collection waveguides are embedded within the substrate in a single or in multiple layers. Alternatively, it is envisioned that the crossing or intersecting involves a physical space or distance between the excitation waveguides and the collection waveguides, for example, where the excitation waveguides and the collection waveguides are embedded within the substrate in separate layers. The optical sensing sites 712 of the system 700 typically are associated with the intersection regions 714.

Typically one optical sensing site 712 is associated with each intersection region 714. As illustrated, in one embodiment the number of intersection regions 714 and optical sensing sites 712 is an arrangement of 100 intersection regions 714 and 100 optical sensing sites 712. It is envisioned that the number of intersection regions and optical sensing regions on a substrate chip can be greater than 10, greater than 100, greater than 1,000 or greater than 10,000. It is further envisioned that the density of intersection regions can be greater than 10 per $cm^2$, greater than 100 per $cm^2$, greater than 1,000 per $cm^2$ or greater than 10,000 per $cm^2$. In one embodiment the density of intersection regions is greater than 2,000 per $cm^2$.

As further shown in FIGS. 7A and 7C, the crossing or intersecting of the excitation waveguides 708 and the collection waveguides 710 can be substantially perpendicular, for example, at an angle of 90°. Alternatively, in certain embodiments the crossing or intersecting can be angled less than or great than 90°.

It is also envisioned that in the embodiments of FIGS. 7A and 7C, a first light wave generated by the active scanning light source chip in an excitation waveguide induces the sensor to transduce an optical signal resulting in a second light wave in a collection waveguide, the second light wave being detectable by the detector.

As illustrated in FIG. 7A, in one advantageous embodiment, the system 700 is a planar two-dimensional detection system. The system 700 in this embodiment includes a planar active scanning light source chip 702 comprising a plurality of light source elements 718, for example an array of switchable lasers, which is scanned perpendicular to the plane of the substrate to couple at some point along its scanning path one or more pulses of light to the plane of the substrate 704, for example, a bio-analysis chip plane. Furthermore, the active scanning light source chip 702 can provide a dynamic source of light for selective and programmed excitation in respect to individual excitation waveguides 708, providing excitation to all of the optical sensing sites 712 along that excitation waveguide 708. A dynamic light source includes but is not limited to a tunable wavelength and/or tunable bandwidth light source. Additionally, the system 700 of this embodiment provides for planar collection of the emitted light from all the excited sensing sites 712 in the collection waveguides 710, specifically in the plane of the substrate 704, such that the light collection is substantially perpendicular to the direction of the light produced in the excitation waveguides 708.

Figure 7D:
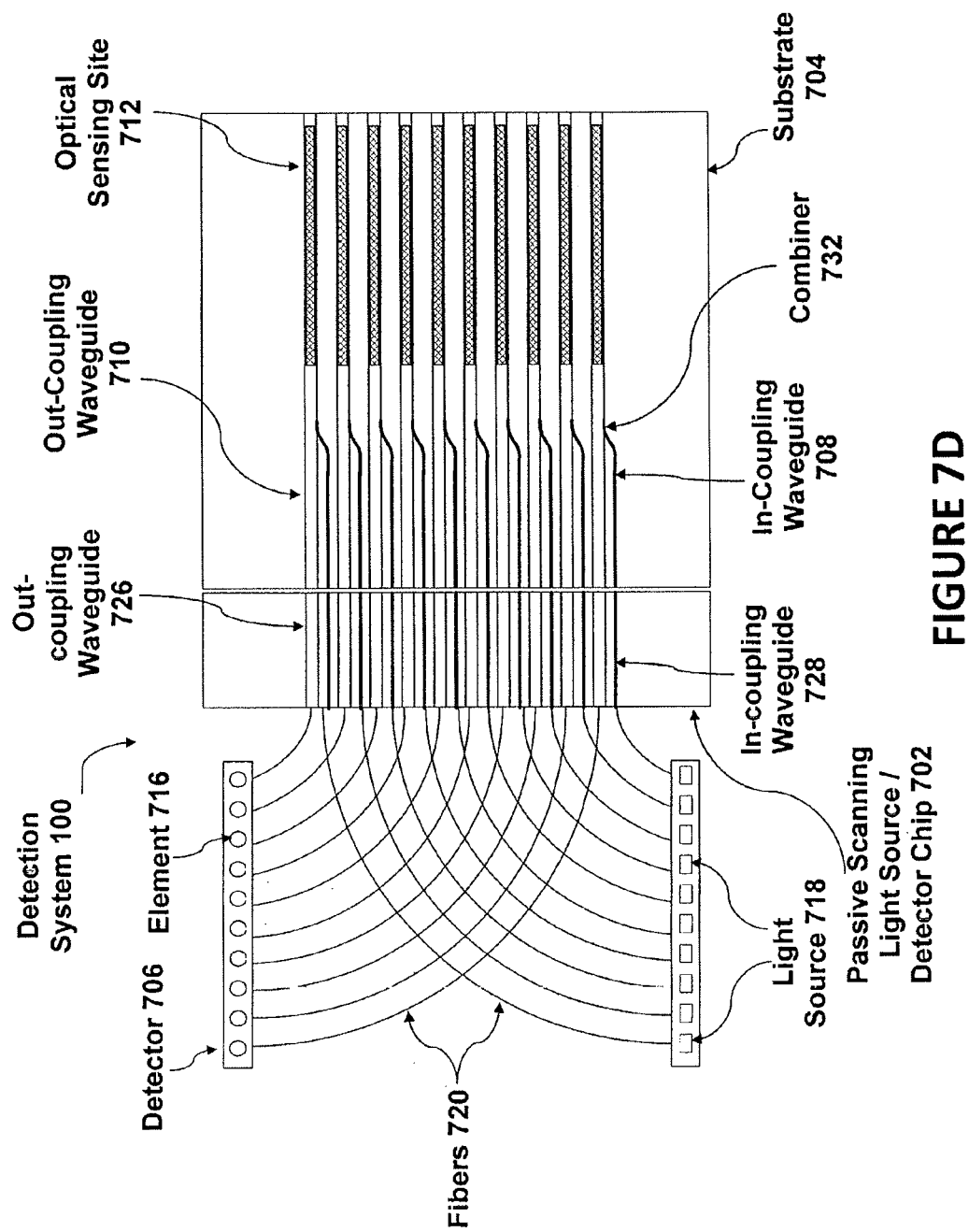
FIG. 7D is a schematic of a detection system according to another embodiment of the invention including a light source, a detector, fibers, a passive light source/detector chip, a substrate and optical sensing sites.

In the embodiments of FIGS. 7B and 7D, it is envisioned that an optical sensing site 712 can be associated with each waveguide 708. It is envisioned that the number of optical sensing sites on a substrate chip can be greater than 10, greater than 100, greater than 200, greater than 1,000, greater than 5,000 or greater than 10,000. It is further envisioned that the density of optical sensing sites can be greater than 10 per $cm^2$, greater than 100 per $cm^2$, greater than 1,000 per $cm^2$ or greater than 10,000 per $cm^2$. In one embodiment the density of optical sensing sites is greater than 2,000 per $cm^2$.

In the embodiments of FIGS. 7B and 7D, it is envisioned that a first light pulse generated by the scanning light source/detector chip in an in-coupling waveguide induces the sensor to transduce an optical signal resulting in a second light pulse in an out-coupling waveguide, the second light pulse being detectable by the detector.

FIG. 7B illustrates an exemplary detection system 700 of the invention including an active scanning light source/detector chip 702, a substrate 704 and optical sensing sites 712. It is envisioned that the light source elements (718) can be any of a number of types of light sources including but not limited to switchable light sources or passive light sources. The active scanning light source/detector chip can include in-coupling waveguides 728, out-coupling waveguides 726 and combiners 730 which combine the in-coupling and the out-coupling waveguides. Such combiners 730 are well known in the art. Substrate 704 can include waveguides 708 and sensing sites 712 in relation to waveguides 708. For example sensing sites 712 can be on top of and in optical communication with waveguides 708. The active scanning light source/detector chip can include one or more detector elements 706.

In a second embodiment, as shown in FIG. 7B, light source elements 718 are coupled to and in optical communication with in-coupling waveguides 728 on the active scanning light source/detector chip. Light generated by the light source travels along in-coupling waveguide 728 and is combined by combiner 730 into the out-coupling waveguide 726. The active scanning light source/detector chip spatially scans perpendicular to the plane of the substrate through a point where each of waveguides 726 is coupled to and in optical communication with its counterpart waveguide 708 on the substrate 704. At this point a light pulse is generated in waveguide 708 travelling from left to right. The light pulse interacts with the sensing area 712 which acts as a transducer to create a second light pulse travelling in waveguide 708 from right to left. This second pulse couples to the out-coupling waveguides 726 on the active scanning light source/detector chip. The second light pulse travels in waveguide 726 to the detector elements on the active scanning light source/detector chip.

FIG. 7C illustrates an exemplary detection system 700 of the invention including a passive scanning light source 702, connected through optical fibers 720 to an external light source comprising light source elements 718, a substrate 704, optical sensing sites 712 and a detector 706. The passive light source chip 702 can include in-coupling waveguides or simply hold the end of the fibers. Substrate 704 includes excitation waveguides 708, collection waveguides 710 and sensing sites 712 on top of and in optical communication with excitation waveguides 708 and collection waveguides 710. Detector 706 can include one or more elements 716 as described herein.

In a third embodiment, as shown in FIG. 7C, light source elements 718 are coupled to and is in optical communication with the in-coupling waveguides of the passive scanning light source chip 702 through a set of optical fibers 720. Passive scanning light source chip 702 is at some point along its scanning path further coupled to and in optical communication with each of the excitation waveguides 708 at an edge of substrate 704. Additionally, detector 706 is coupled to and in optical communication with collection waveguides 710 at a second edge of substrate 704.

FIG. 7D illustrates an exemplary detection system 700 of the invention including a passive scanning light source/detector chip 702, two sets of optical fibers 720, a light source comprising light source elements 718, a detector 706, a substrate 704, in-coupling waveguides 708 and 728, out-coupling waveguides 710 and 726 and optical sensing sites 712.

In a fourth embodiment, as shown in FIG. 7D, light source elements 718 are connected to and in optical communication with the in-coupling waveguides 728 on the passive scanning light source/detector chip 702 through a set of optical fibers 720. In addition, detector 106 is connected to and in optical communication with the out-coupling waveguides 726 on the passive scanning light source/detector chip through a second set of optical fibers 720. The passive scanning light source/detector chip, at some point along its scanning path, is coupled to and in optical communication with in-coupling waveguides 708 on the substrate 704. At that same point along the scanning path, the out-coupling waveguides 710 on substrate 704 are in optical communication with the out-coupling waveguides 726 on the passive scanning light source/detector chip.

FIG. 7E illustrates a side view of an exemplary detection system 700 of the invention including a scanning light source/detector chip 702, a substrate 704 and a piezoelectric bending actuator 705.

In the side view shown in FIG. 7E, the piezoelectric bending actuator is used to move the scanning light source/detector chip up and down thus scanning through a point along the scanning path where the scanning light source/detector chip is coupled to and in optical communication with the waveguides on substrate 704. At that point a first light pulse is generated in the in-coupling waveguides of substrate 704. At the same point a second light pulse is coupled back from the out-coupling waveguides of substrate 704 to the out-coupling waveguides on the scanning light source/detector chip. While FIG. 7E illustrates the particular embodiment of the detection system shown in FIG. 7D, this particular embodiment is representative of any of the other embodiments of the detection system of the invention. Similarly, the piezoelectric bending actuator is a representative of a variety of possible means for spatially translating the light emitted from the light source relative to the substrate. In various embodiments, the means for generating the relative motion of the light emitted from the light source relative to the substrate may include a piezoelectric based motor, a step motor, an electrical motor, a magnetic actuator, a memory metal actuator, a solenoid, or a hydraulic actuator. The movement of the actuator may be effected by electrical power, thermal power, magnetic power or even mechanical power (i.e., manually).

Figure 7F:
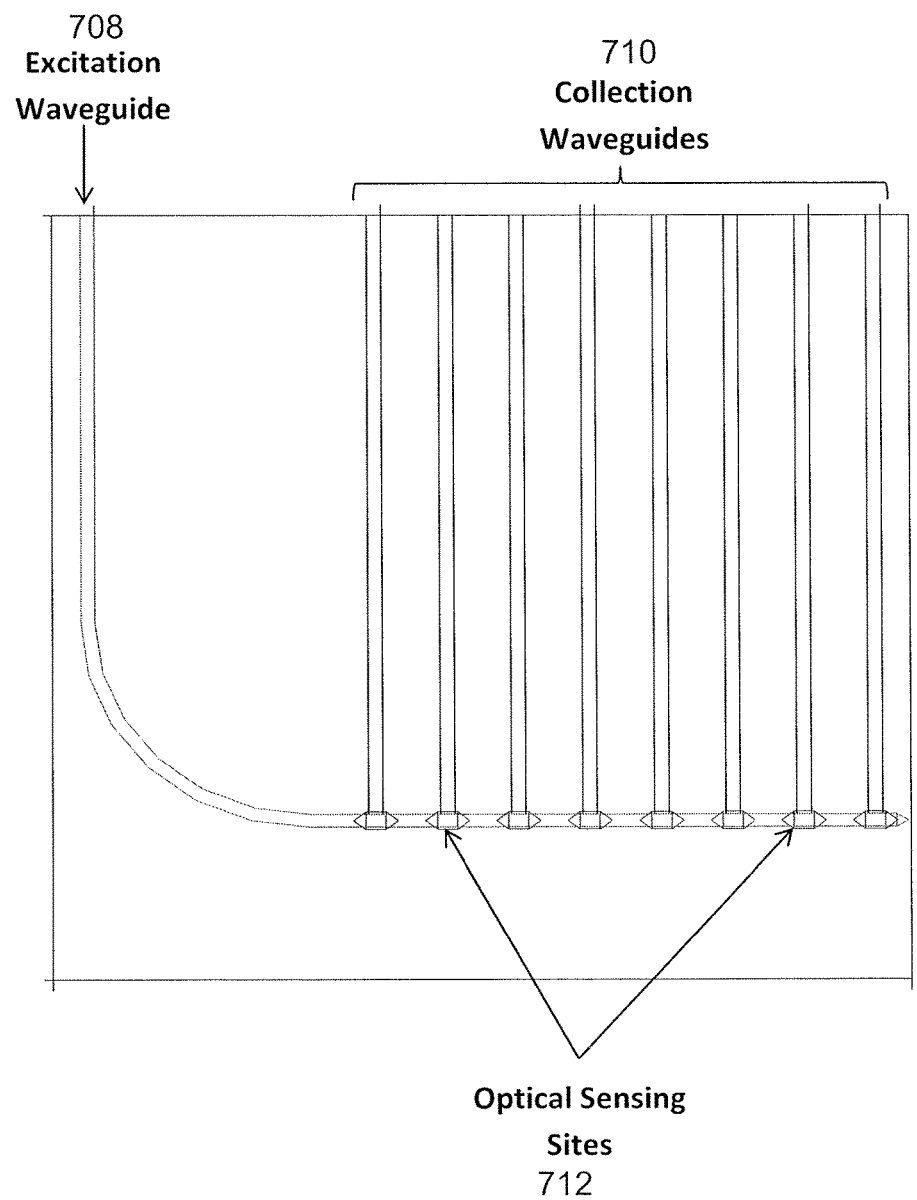
FIG. 7F is a schematic of another embodiment of a substrate having a single excitation waveguide and a plurality of collection waveguides that exit the same side of the substrate.
Figure 7G:
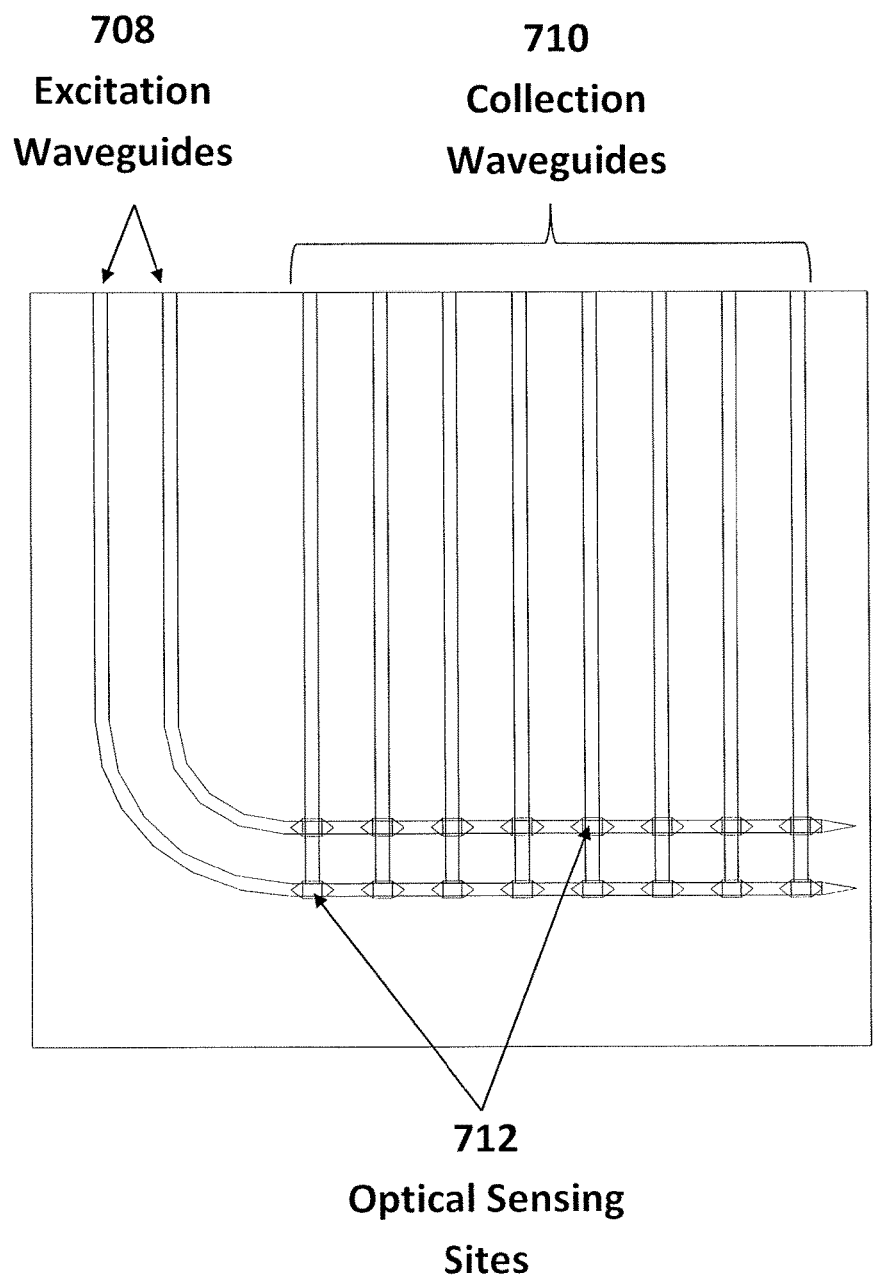
FIG. 7G is a schematic of another embodiment of a substrate having a plurality of excitation waveguides and a plurality of collection waveguides that exit the same side of the substrate.

FIGS. 7F and 7G illustrate another exemplary chip configuration where the one or more excitation waveguides 708 exit or extend to the same edge of the chip substrate as the one or more collection waveguides 710. As illustrated in FIG. 7F, the substrate has one excitation waveguide 708. In other embodiments, as illustrated in FIG. 7G, the substrate can have a plurality of excitation waveguides. The excitation waveguides 708 can cross the collection waveguides 710 as described herein. For example, the excitation waveguides 708 can cross the collection waveguides 710 perpendicularly or approximately perpendicularly to form a plurality of optical sensing sites 712 at the intersections, where each optical sensing site 712 is in optical communication with both the excitation waveguide 708 and the collection waveguide 710. The excitation waveguides 708 can bend or curve approximately 90 degrees to exit the same edge of the substrate as the collection waveguides 710. In some embodiments, the excitation waveguides 708 can be on one portion or side of the substrate while the collection waveguides 710 can be on another portion or side of the substrate. By having the excitation waveguides 708 exit the substrate at the same side as the collection waveguides 710, only one side or edge of the substrate or chip needs to be aligned with another chip or substrate having the light sources and detectors. By reducing the number of alignments needed between the components, the manufacturing process may be simplified, thereby reducing manufacturing costs.

Figure 7H:
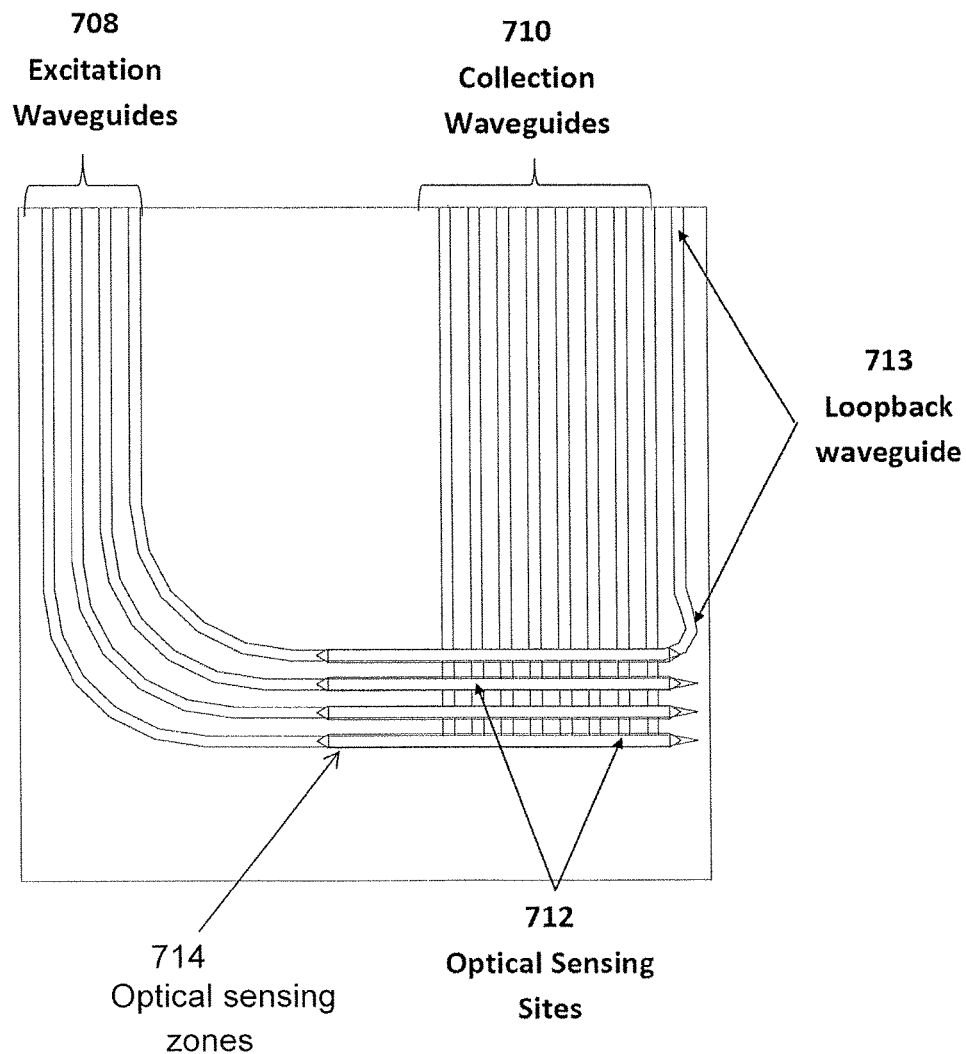
FIG. 7H is a schematic of an embodiment of a substrate having excitation waveguides and collection waveguides and a loopback waveguide that exits the same side of the substrate.

FIG. 7H illustrates another embodiment of a chip configuration that is similar to the configuration shown in FIG. 7G, but with an added loopback waveguide 713 that also exits or extends to the same edge of the chip substrate as both the excitation waveguides 708 and collection waveguides 710. The loopback waveguide 713 can be an extension of one of the excitation waveguides 708 that loops back and extends to the edge of the chip substrate in which the other waveguides extend or exit. The loopback waveguide 713 can be used to efficiently align the chip with the light source, detectors, optical fibers, and/or other waveguides by detecting the injected light with a detector at the loopback waveguide output. The position of the chip can be adjusted until light is detected by the loopback waveguide detector. Without the loopback waveguide, very little light may enter the collection waveguides during alignment when no sample is present, making alignment using the detectors more difficult.

In addition, FIG. 7H also illustrates an optical sensing zone 714 where the cladding has been removed to allow the light to interact with the optical sensing sites 712. In some embodiments as described elsewhere in this application, the cladding is only removed at the intersections between the collection and excitation waveguides where the optical sensing sites are located. However, in other embodiments, as shown in FIG. 7H, a larger segment of cladding can be removed from the excitation waveguides, starting from a point before the excitation waveguides intersect the first collection waveguides, extending across the collection waveguides, and ending at a point after the excitation waveguides pass the last collection waveguides. Light scattering can occur at the transition between a cladded and non-cladded portion of the excitation waveguide. This scattered light can enter the collection waveguide and interfere with detection and measurements of light emission from the collection waveguide. By moving and eliminating the cladding transitions near the optical sensing sight, light scattering can be reduced, thereby improving the sensitivity and/or accuracy of the system. As shown, the cladding transitions for the optical sensing zones 714 are located away from the optical sensing sites and are limited to a single transition before the collection waveguides and a single transition after the collection waveguides. The cladding transitions of the optical sensing zones 714 can be located far enough away from the collection waveguides to prevent, minimize or reduce light scattering interference.

Although four exemplary embodiments of the detection system of the invention are specifically disclosed herein, it is envisioned that any of a number of other combinations of coupling the different components/chips disclosed herein at different edges of the components/chips are possible. For example, in one embodiment, a first scanning light source/detector chip is coupled to a first edge of the substrate and a second scanning light source/detector chip is coupled at a second edge of the substrate (not shown). It can be understood accordingly that the passage of light pulses within the devices and systems described herein, though described in terms of "left" and "right" can be practiced in a variety of directions and orientations based on the flexible arrangements of components provided herein. Furthermore, additional combinations of the different scanning chips with the different substrates are envisioned. For example, the scanning light source chips shown in FIGS. 7A and 7C may be used in combination with the substrates shown in FIGS. 7B and 7D, together with a detector in optical communication with an opposite end of the substrate. In addition, in the embodiments illustrated in FIGS. 7B and 7D, either the scanning chip or the substrate may comprise at least one combiner.

Although in all of the above embodiments the scanning light source is spatially translated relative to the substrate, it is further envisioned that the scanning of the emitted light relative to the waveguides of the substrate may also be effected by spatially translating the substrate relative to the light source, or by spatially translating any part or component of the scanning light source, such as one or more mirrors, lenses, or prisms, using any of the means disclosed herein.

It is envisioned that an optical sensing site 712 can be associated with each waveguide 708. It is envisioned that the number of optical sensing sites on a substrate chip can be greater than 10, greater than 100, greater than 200, greater than 1,000, great than 5,000 or greater than 10,000. It is further envisioned that the density of optical sensing sites can be greater than 10 per $cm^2$, greater than 100 per $cm^2$, greater than 1,000 per $cm^2$ or greater than 10,000 per $cm^2$. In one embodiment the density of optical sensing sites is greater than 2,000 per $cm^2$.

It is envisioned that in any of the embodiments described herein, that a first light pulse generated by the scanning light source chip in an in-coupling or excitation waveguide induces the sensor to transduce an optical signal resulting in a second light wave in an out-coupling or collection waveguide, the second light wave being detectable by the detector.

FIG. 8 is an exemplary illustration of the detection system of the invention as part of a working system 801 in a housing 809. While the detection system illustrated in FIG. 7A-7E is the core of the present invention, in order to facilitate the operation of this system, one or more other modules can be included in a working system that includes the detection system components of the invention.

FIG. 8 illustrates one possible configuration for a working system 801 that can include housing 809 for enclosing various modules of working system 801 including but not limited to substrate 804, robotic system 803, scanning light source chip 802, multi-element detector 806, electronic boards 807 and interface panel 805. Substrate 804, scanning light source chip 802, and multi-element detector 806, are discussed in detail below.

In regard to housing 809, as shown in FIG. 8, in one embodiment an enclosure or housing 809 holds in place two fixed chips (e.g., of a 3-chip architecture), namely, scanning light source chip 802 and multi-element detector 806. Accordingly, in this embodiment substrate chip 804 is movable in relation to scanning light source chip 802 and multi-element detector 806. Housing 809 can include any number of accurately machined parts and or components as described herein, allowing, for example, the relative alignment of the 3 optical chips, and the movement of the scanning light source chip perpendicular to the plane of the substrate. The working system housing can optionally include temperature control and vibration isolation for the working system (not shown).

As shown in FIG. 8, working system 801 can further include an X, Y, Z, θ robotic system 803 for positioning substrate 804 as required within working system 801. X, Y, Z, θ robotic system 803 can be a translation stage with several degrees of freedom for receiving or accepting substrate 804, holding it in place, and aligning it in relation to the rest of working system 801. As desired, at the end of a run X, Y, Z, θ robotic system 803 can eject substrate 804 from working system 801.

It is envisioned that the working system can further include an aligning system (not shown). An aligning system can include one or more light sources, one or more detectors and one or more cameras for active detection of the position of the substrate of the invention. Based on the detected position, the aligning system can align the substrate to the rest of the working system modules, for example, to provide aligned optical communication between the substrate and the scanning light source/detector chip.

As shown in FIG. 8 working system 801 can further include one or more electronic boards 807, for example, an electronic driving board and a control board. It is envisioned that one or more electronic boards can control all the different parts of the working system. Electronic boards 807 can control scanning light source 802 and any other light source present in the system. Electronic boards 807 can be adapted to read any or all of the detectors and cameras in working system 801. Electronic boards 807 can further be adapted to drive robotic system 803 and control its motion, to control the motion of the scanning light source chip, and optionally to monitor and control temperature in different areas of the system. Electronic boards can include logic elements and processors (not shown). It is envisioned that electronic boards can further include embedded software both for controlling the working system and for interfacing the outside world, for example by way of interface panel 805 which can include a key-pad or any other input/output port.

As shown in FIG. 8 working system 801 can additionally include one or more interface panel 805. It is anticipated that the system will have one or more interface panel 805 to allow a user to interface with the system and operate it. Interface panels can include any number of input and output ports well known in the art for connecting the system to other systems or to an external control console (not shown).

Figure 9A:
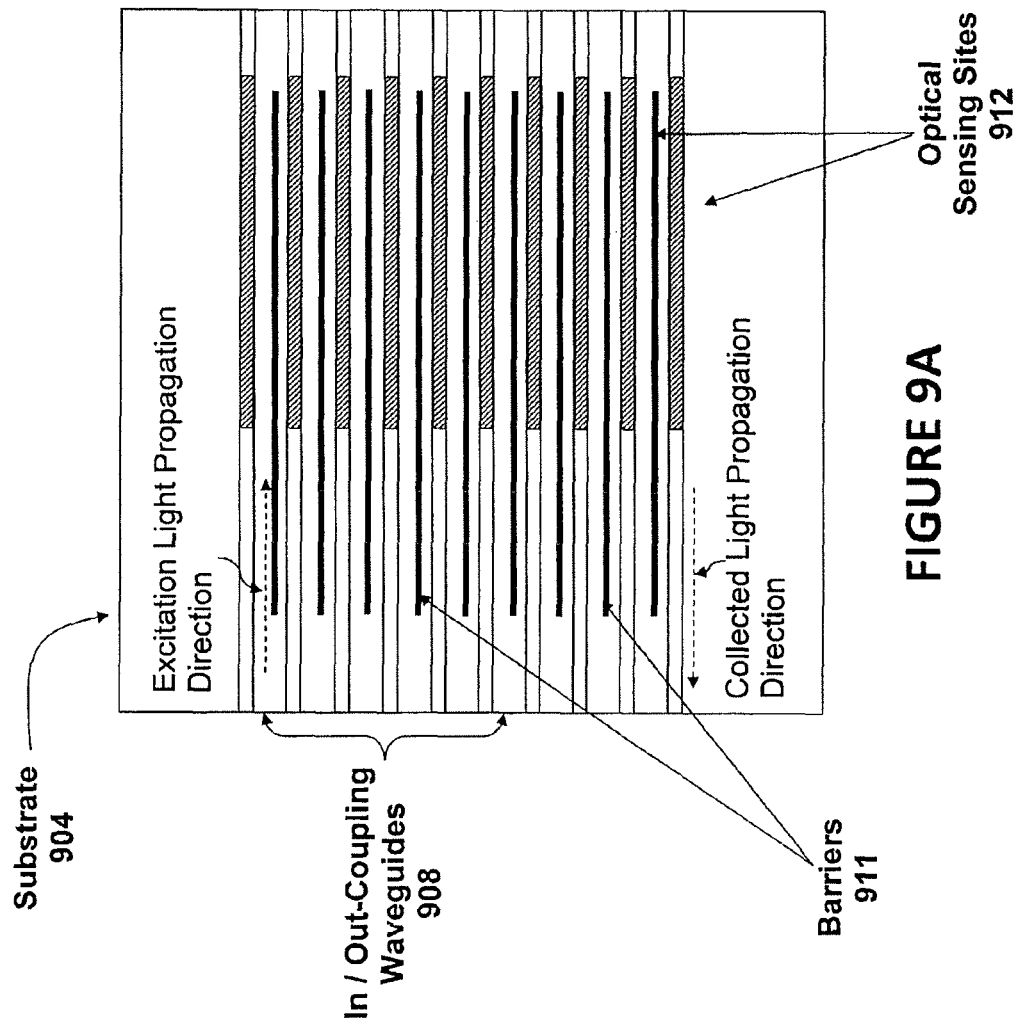
FIG. 9A is a schematic of the substrate of the invention according to one embodiment including optical waveguides in conjunction with optical sensing sites and barriers.

FIG. 9A illustrates an exemplary substrate 904 of the second embodiment of the detection system of the current invention (as show in FIG. 7B) further including barriers 911 intended to block stray light within the substrate and reduce crosstalk between the different elements of the substrate. Barriers 911 can be light absorbing or light reflecting. Barriers 911 can be variously sized, shaped and positioned between waveguides 908 in any of a number of orientations to achieve a desired optical effect. As shown in FIG. 9A, barriers 911 can be arranged between two adjacent waveguides and proximal to optical sensing sites 912. Waveguides 908 are used to guide a primary light wave (excitation light; see dashed arrow) from the left edge of substrate 904 to optical sensing sites 912. Waveguides 908 then guide a secondary light wave (collected at optical sensing sites 912; see dashed arrow) from optical sensing sites 912 back to the left edge of substrate 904.

Figure 9B:
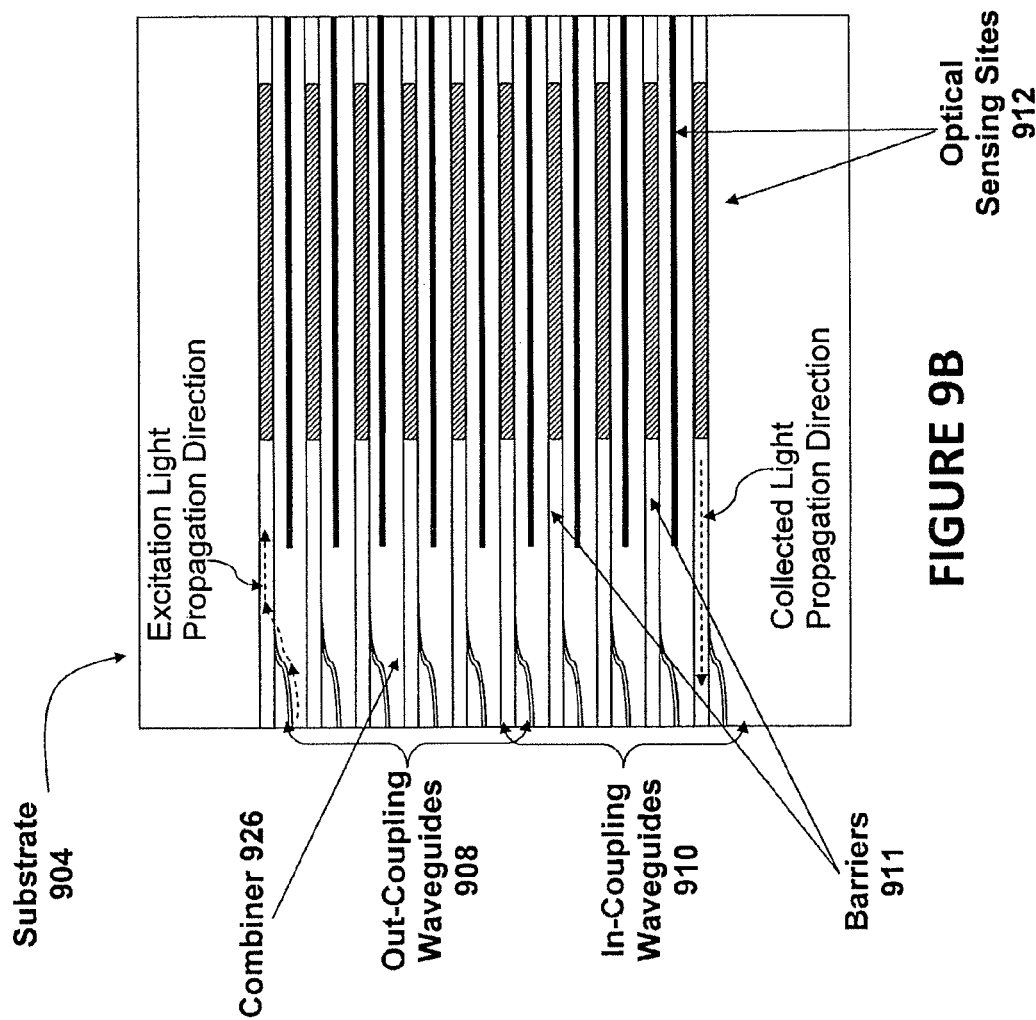
FIG. 9B is a schematic of the substrate of the invention according to another embodiment including optical waveguides and combiners in conjunction with optical sensing sites and barriers.

FIG. 9B illustrates an exemplary substrate 904 of the fourth embodiment of the detection system of the current invention (as shown in FIG. 7D) further including in-coupling waveguides 908 and combiners 926. The primary light wave (excitation light; see dashed arrow) is coupled to substrate 904 through in-coupling waveguides 908 at the left edge of substrate 904. The excitation light traveling from left to right is combined by combiners 926 into out-coupling waveguides 910 which further guide it to optical sensing sites 912. Out-coupling waveguides 910 are then used to guide the secondary light wave (collected at sensing sites 912; see dashed arrow) from optical sensing sites 912 back to the left edge of substrate 904. Barriers 911 have the same purpose as described above in FIG. 9A.

Figure 9C:
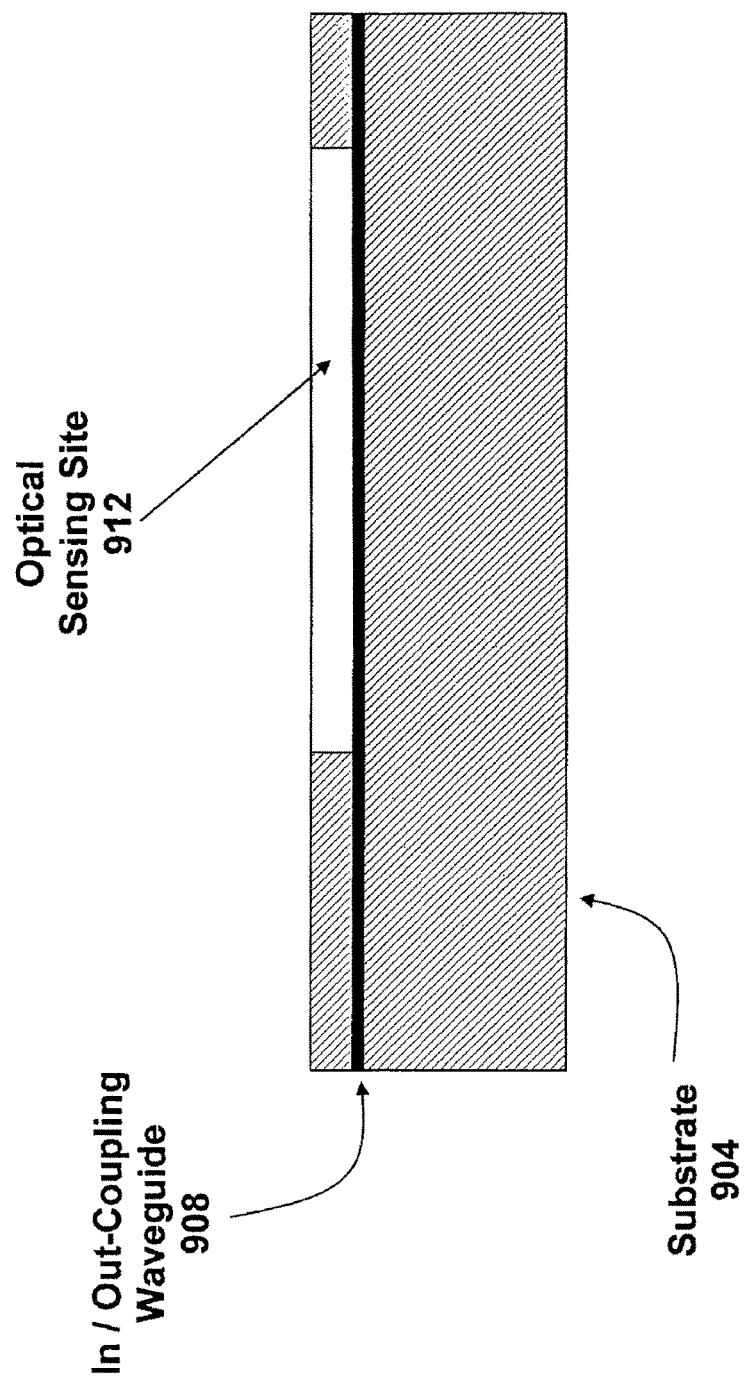
FIG. 9C is a schematic cross section of the substrate of the invention according to one embodiment including an optical waveguide in conjunction with an optical sensing site.

FIG. 9C schematically illustrates a cross section of the substrate 904 of one embodiment of the current invention. In the example illustrated, in/out coupling waveguides 908 are embedded underneath a surface of substrate 904. Optical sensing sites 912 can be etched into a surface, for example, the upper cladding of substrate 904 and located, for example, adjacent to and on top of waveguide 908 facilitating optical communication between them. It is envisioned that in a different embodiment, the optical sensing sites can also be located on the surface of substrate 904 or etched only part of the way into the upper cladding, or all the way through the waveguides (not shown). It is also envisioned that the waveguides can be single-mode waveguides, multi-mode waveguides or any combination of the two, namely, single mode in the vertical dimension and multi-mode in the lateral dimension.

Figure 9D:
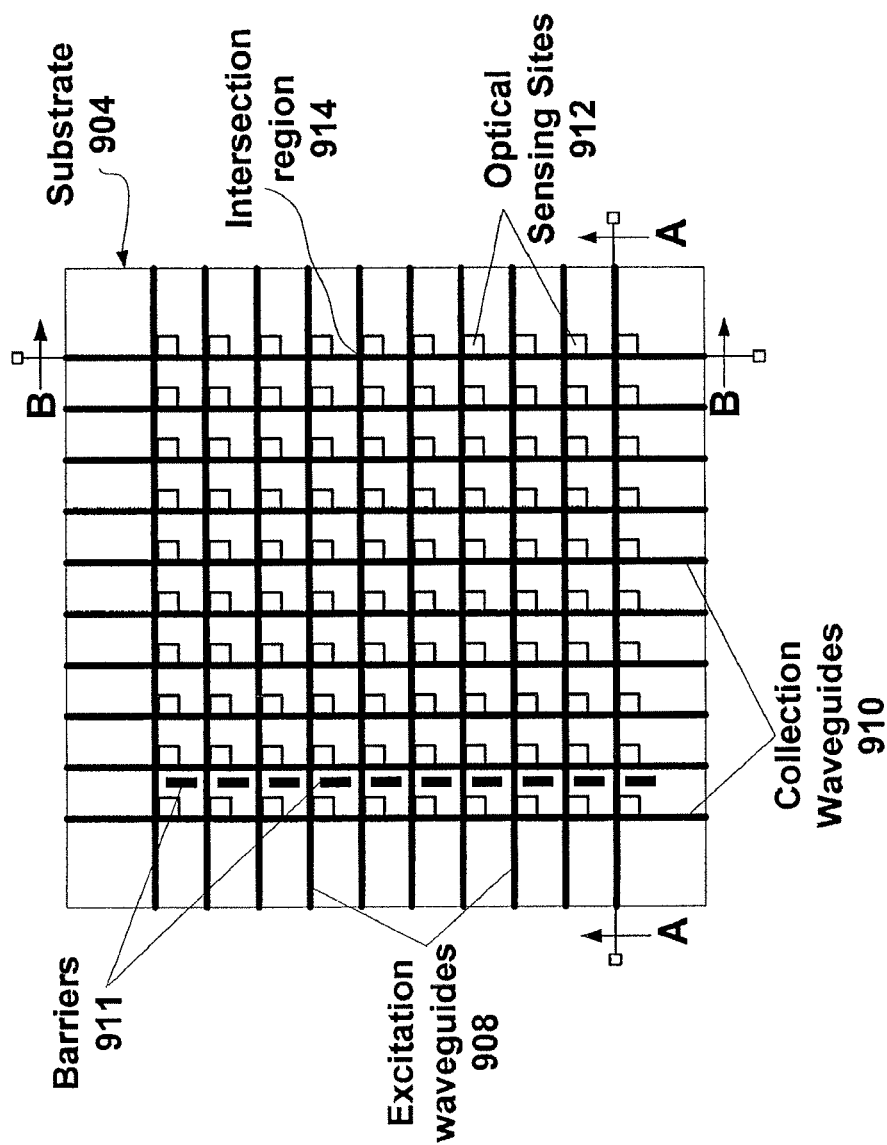
FIG. 9D is a schematic of the substrate of the invention according to another embodiment including excitation and collection optical waveguides in conjunction with optical sensing sites and barriers.

FIG. 9D illustrates an exemplary substrate 904 of the first and third embodiments of the detection systems of the current invention (as shown in FIGS. 7A and 7C), further including barriers 911 intended to block stray light within the substrate and reduce crosstalk between the different elements of the substrate. The barriers 911 can be light absorbing or light reflecting. The barriers 911 can be variously sized, shaped and positioned between the collection waveguides 910 and/or the excitation waveguides 908 in any of a number of orientations to achieve a desired optical effect. As shown in FIG. 9D, the barriers 911 can be arranged in a row between two adjacent collection waveguides and proximal to the optical sensing sites 912 and intersection region 914.

Figure 9E:
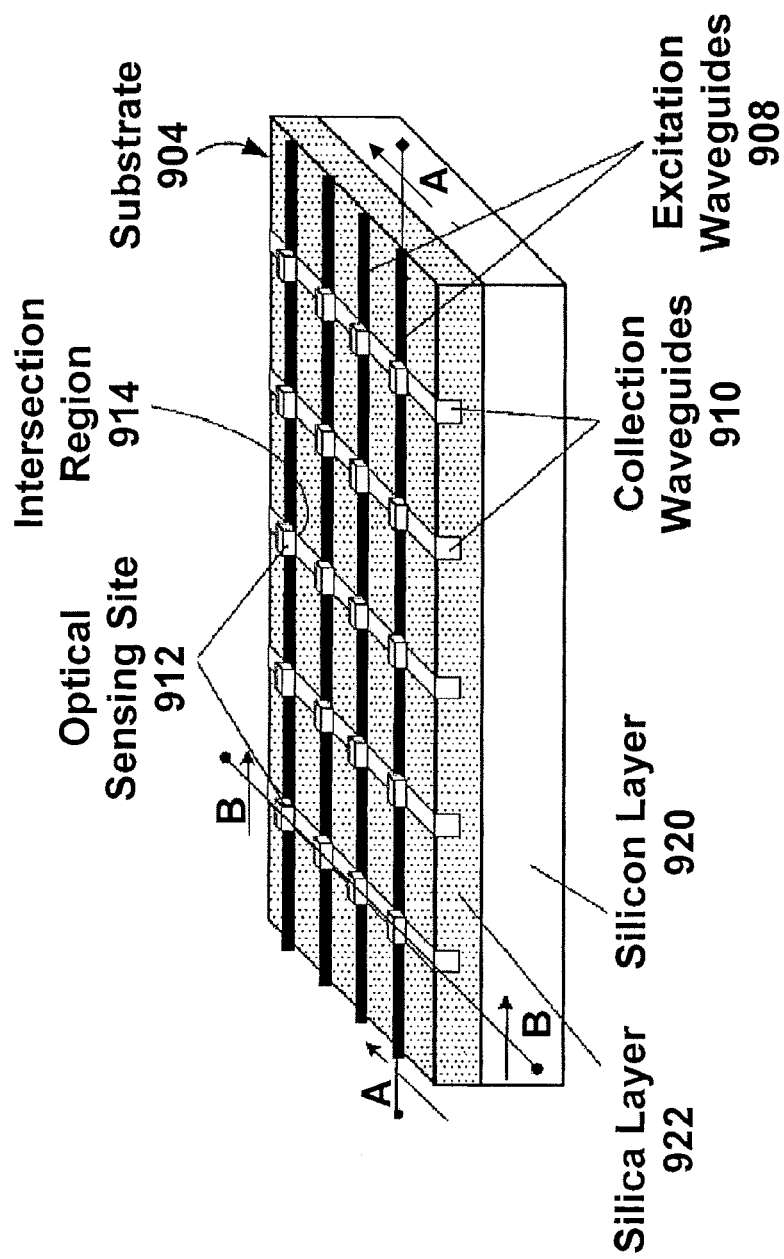
FIG. 9E is a perspective view of the substrate of the embodiment of the invention shown in FIG. 9D including excitation and collection optical waveguides in conjunction with optical sensing sites.

As shown in FIG. 9E, (in this view a top cladding layer is not shown) in one embodiment the substrate 904 can include excitation waveguides 908 and collection waveguides 910 embedded beneath a surface of the substrate 904 in multiple layers. As shown, the excitation waveguides 908 cross, physically intersect, and are in optical communication with the collection waveguides 910 at the intersection regions 914. In the embodiment shown in FIG. 9E, the optical sensing site 912 is positioned at the intersection region 914 above and in optical communication with the excitation waveguides 908. As further shown in FIG. 9E, the substrate 904 includes multiple layers including a silicon layer 920 and a silica (SiO2) layer 922, wherein the excitation waveguides 908 and the collection waveguides 910 are embedded within the silica (SiO2) layer 922.

Figure 9F:
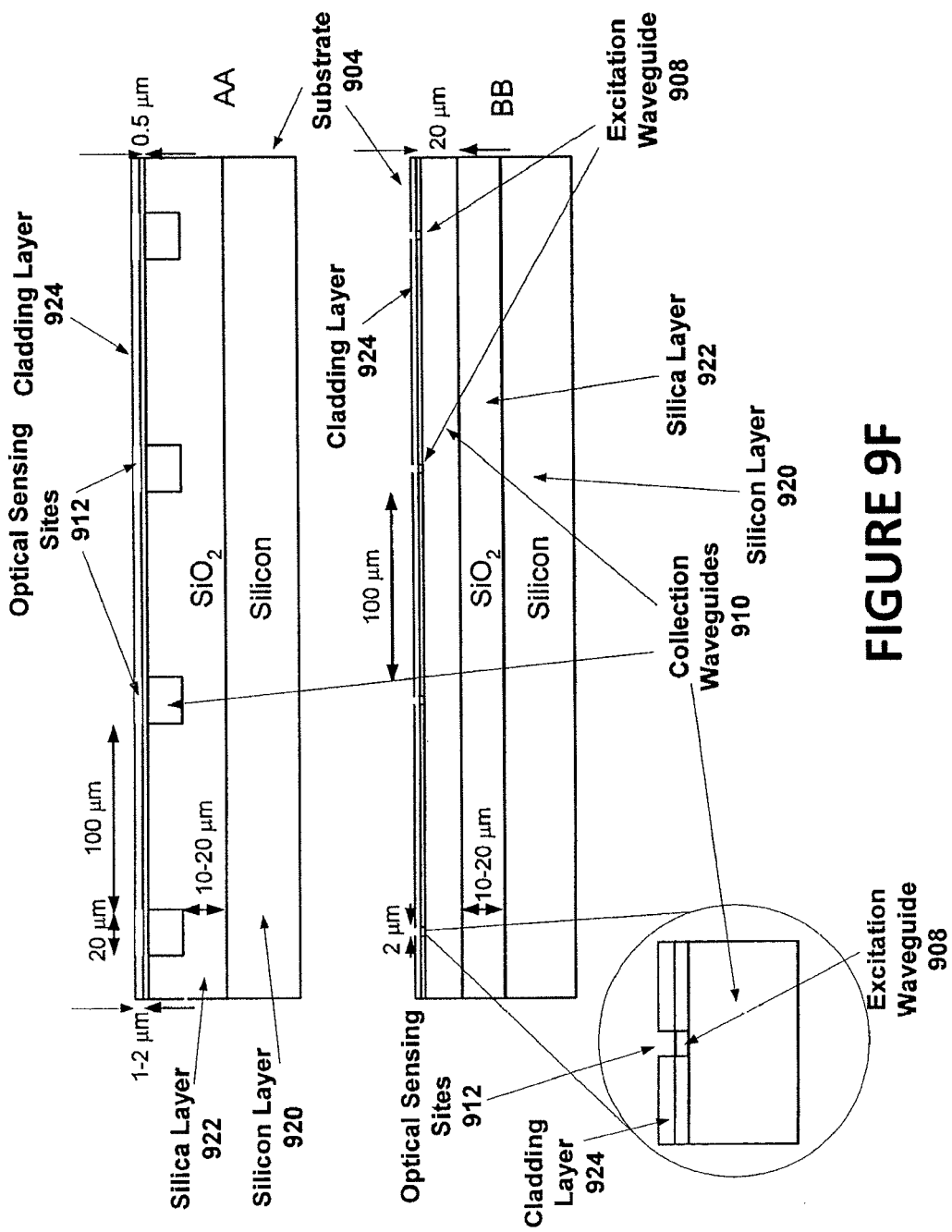
FIG. 9F is a schematic of two cross sectional views (AA and BB) of the substrate shown in FIGS. 9D and 9E.

As shown in FIG. 9F, in another embodiment the substrate can include excitation waveguides 908 and collection waveguides 910 embedded underneath a surface of the substrate 904 in a single layer. As shown, the excitation waveguides 908 cross, physically intersect and are in optical communication with the collection waveguides 910. In contrast to the embodiment shown in FIG. 9E, here the intersection between excitation waveguides 908 and collection waveguides 910 occurs internal to the collection waveguides 910. As further shown in FIG. 9F, the substrate 904 includes multiple layers including a silicon layer 920, a silica (SiO2) layer 922, and a cladding layer 924. As shown, the excitation waveguides 908 and collection waveguides 910 can be embedded within the silica (SiO2) layer 922. Additionally, the optical sensing site 912 can be embedded within both the cladding layer 924 and the silica (SiO2) layer 922. Optionally, the optical sensing site can be embedded solely within the cladding layer (not shown).

It is envisioned that the excitation waveguides and collection wave guides can be single-mode or multi-mode waveguides. In one embodiment, the excitation waveguides are single-mode and the collection waveguides are multi-mode. It is envisioned that waveguide configurations can include single- or multi-mode configurations in either vertical or lateral orientations within a waveguide. For example, in one specific and non-limiting embodiment, the excitation waveguides 908 can support a single mode in the vertical dimension and multi modes in the lateral dimension. Optionally, as shown in FIG. 9D, the excitation waveguides 908 and the collection waveguides 910 can span the entire substrate from one edge to another edge.

As shown in FIG. 9F, the substrate 904 components and optical sensing sites 912 can include dimensions. FIG. 9F shows two cross-section views of the substrate 904. View AA is a cross-section view in plane A as indicated in FIG. 9D and FIG. 9E. View BB is a cross-section view in plane B as indicated in FIG. 9D and FIG. 9E. As shown in FIG. 9F, the thickness of the cladding layer 924 above the excitation waveguides can be about 0.1 µm to about 20 µm. In one embodiment the cladding layer 924 thickness is about 1 µm to about 2 µm. By way of a non-limiting example, as shown in FIG. 9F, an opening of the optical sensing site 912 can include the following dimensions: about 20 µm by about 2 µm. The distance between collection waveguides 910 can range from about 1 µm to about 1000 µm. For example, as shown in FIG. 9F, the distance between collection waveguides 910 can be about 100 µm. The distance between collection waveguides 910 and the silicon layer 920 can be about 1 µm to about 100 µm. For example, as shown in FIG. 9F, the distance between collection waveguides 910 and the silicon layer 920 can be about 10 µm to about 20 µm.

As shown in FIGS. 9E and 9F, the excitation waveguides 908 and collection waveguides 910 can be channel waveguides. Exemplary ranges for waveguide dimensions in the embodiment shown in FIGS. 9E and 9F include about 0.1 to about 10 µm thick and about 1 to about 100 µm wide. By way of non-limiting example only, the excitation waveguides 908 can include cross-section dimensions of about 0.1 µm by about 100 µm and the collection waveguides 910 can include cross-section dimensions of about 0.2 µm by about 100 µm.

Figure 9G:
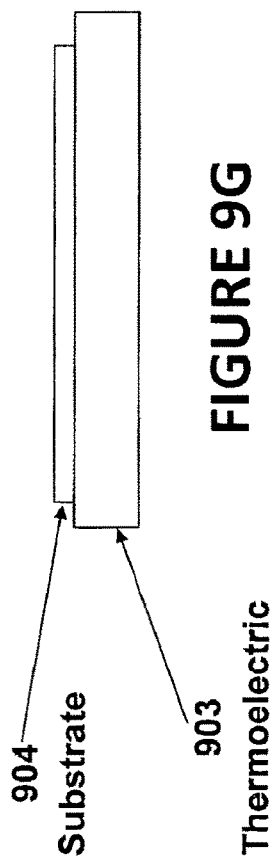
FIG. 9G is a schematic of a side view of the substrate of one embodiment of the invention in relation to a thermo-electric cooler.

FIG. 9G in a side view illustrates another embodiment of substrate 904 of the invention in relation to a thermal transfer element 903, for example, a thermoelectric cooler (TEC). Thermal transfer element 903 is a temperature control system useful for heating or cooling a chip, for example, substrate 904. Although the thermal transfer element may be referred to herein as a cooling element, it is to be understood that where the thermal transfer element is configured to increase and decrease the temperature of a chip, the component functions essentially as a heating and as a cooling element depending on the induced direction of the electrical current. The thermal transfer element can provide a range of useful temperatures. For example, the thermal transfer element can be configured to provide a temperature in the range between about −40° C. to about 120° C. as desired. The thermal transfer 903 element can be adapted to receive substrate 904 of the invention. The thermal transfer element 903 can be adapted to contact part or all of a surface of the substrate 904 of the invention.

Providing thermal transfer element 903 in conjunction with substrate 904 of the invention is useful, for example, for the amplification of tested sample molecules through processes such as the polymerase chain reaction (PCR) as described herein. In use, the embodiment as described for FIG. 9G provides the capability of controlling the temperature of the entire substrate such that as the temperature of the entire substrate is cycled, samples at any optical sensing site can be amplified by PCR simultaneously.

Figure 9H:
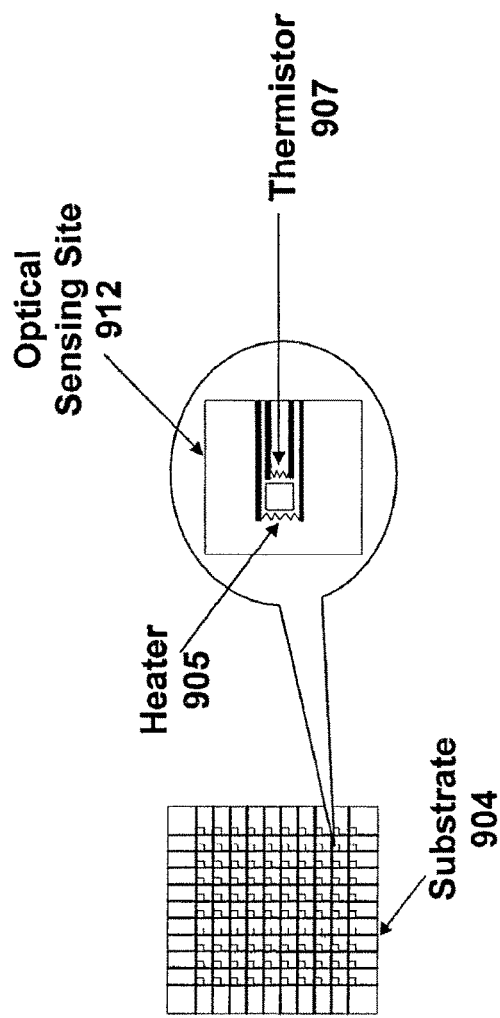
FIG. 9H is a schematic of one embodiment of the substrate of the invention illustrating details of an optical sensing site including a heater and a thermistor.

FIG. 9H illustrates another embodiment of substrate 904 of the invention wherein optical sensing site 912 includes heater 905 and thermistor 907. In this embodiment, optical sensing site 912 of substrate 904 can include heater 905, for example, a thin-film heater, in the vicinity of each sensing sites 912. Heater 905 can be adapted to enable individual temperature control for each sensing site 912. In addition to heater 905, thermistor 907 can be located at or near each sensing site 912 thereby providing for measuring the local temperature. In use, this embodiment provides the capability of running the same or any desired different number of cycles and the same or any desired different temperature profiles for each and every sensing site.

Figure 9I:
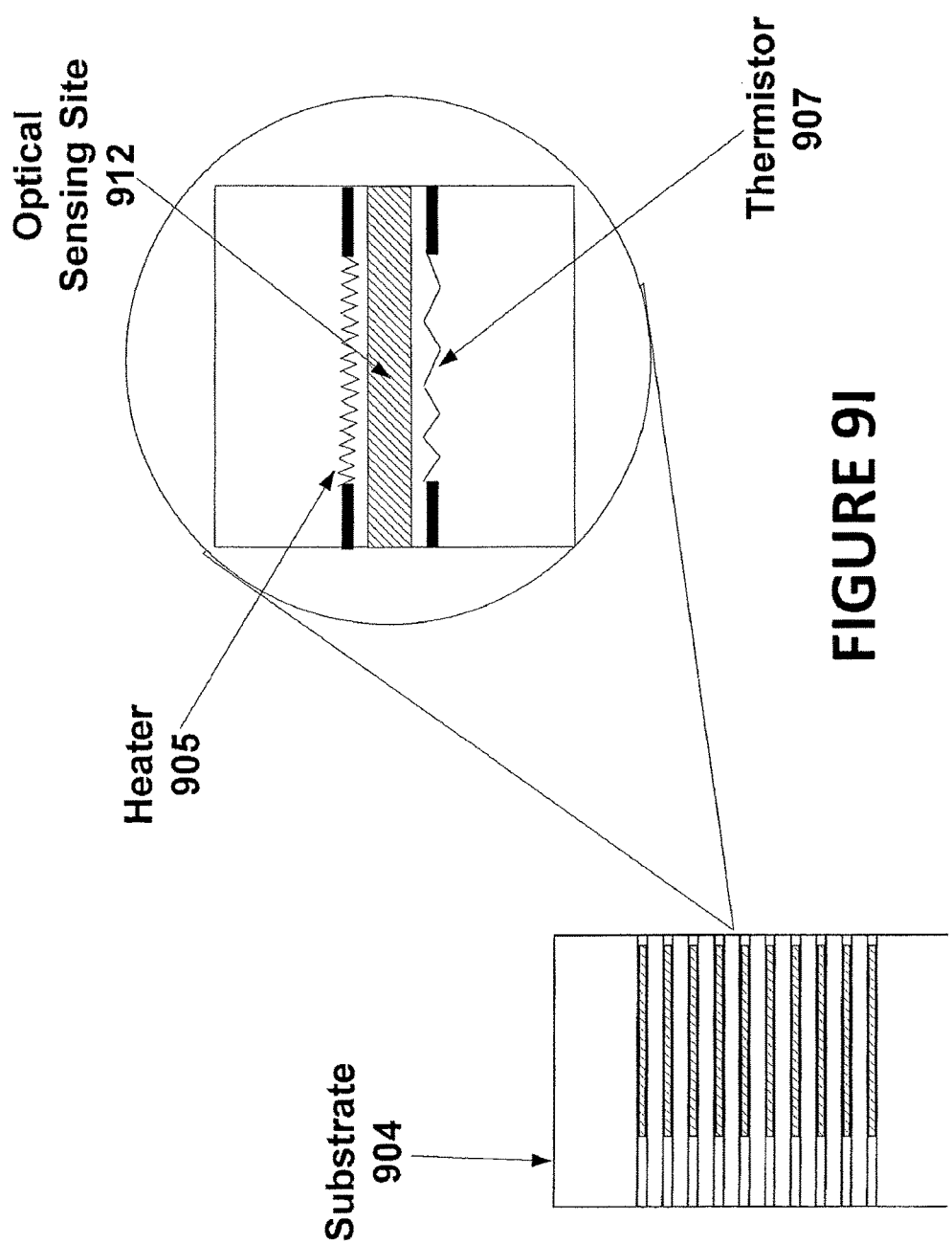
FIG. 9I is a schematic of another embodiment of the substrate of the invention illustrating details of an optical sensing site including a heater and a thermistor.

FIG. 9I illustrates yet another embodiment of substrate 904 of the invention wherein optical sensing site 912 includes heater 905 and thermistor 907. In this embodiment, optical sensing site 912 of substrate 904 can include heater 905, for example, a thin-film heater, in the vicinity of one or more sensing site 912. Heater 905 can be adapted to enable individual temperature control for each sensing site 912. In addition to heater 905, thermistor 907 can be located at or near one or more sensing site 912 thereby providing for measuring the local temperature. In use, this embodiment provides the capability of running the same or any desired different number of cycles and the same or any desired different temperature profiles for each and every sensing site.

Advantageously, the embodiments described for FIGS. 9G, 9H, and 9I can support real-time PCR. As described herein, since optical detection is done from within the substrate, signal detection these both embodiments (see FIGS. 9G, 9H, and 9I) can be done while the samples are in the process of the amplification cycles, thereby enabling real time analysis of the PCR process.

Figure 9J:
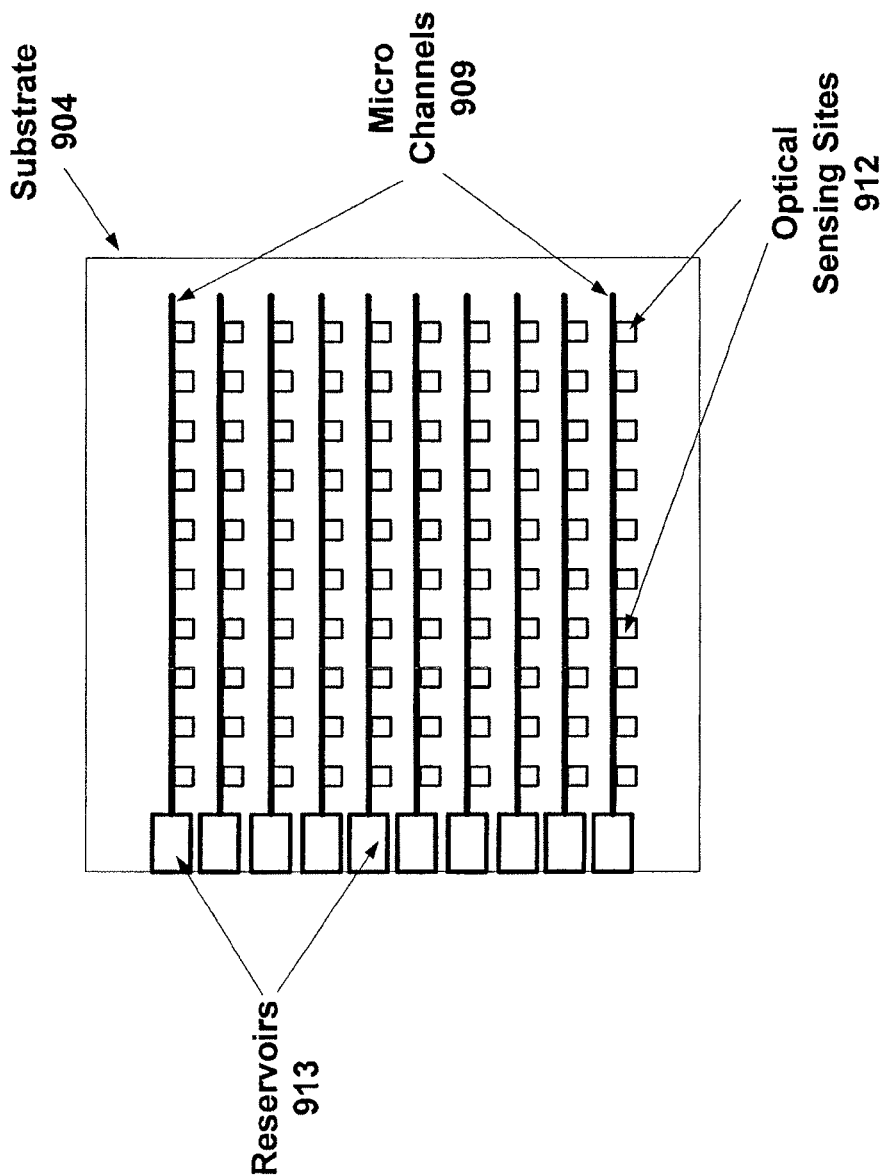
FIG. 9J is a schematic of one embodiment of the substrate of the invention including reservoirs and micro channels in relation to optical sensing sites.

FIG. 9J illustrates yet another embodiment of substrate 904 of the invention wherein substrate 904 additionally includes reservoirs 913 and microchannels 909 in relation to optical sensing sites 912. As such, in this embodiment microfluidics are incorporated into the substrate. Microfluidics can be adapted to drive liquid (in this case the tested sample) using the capillary effect across the substrate. As illustrated in FIG. 9J, this can be achieved by an arrangement of microchannels 909, optionally of varying width, which force the sample from one or more reservoirs 913 to optical sensing sites 912 which can include etched wells to receive the sample. The microchannels can be either etched on the face of the chip itself or can be added as an external structure on a surface of the substrate.

Figure 9K:
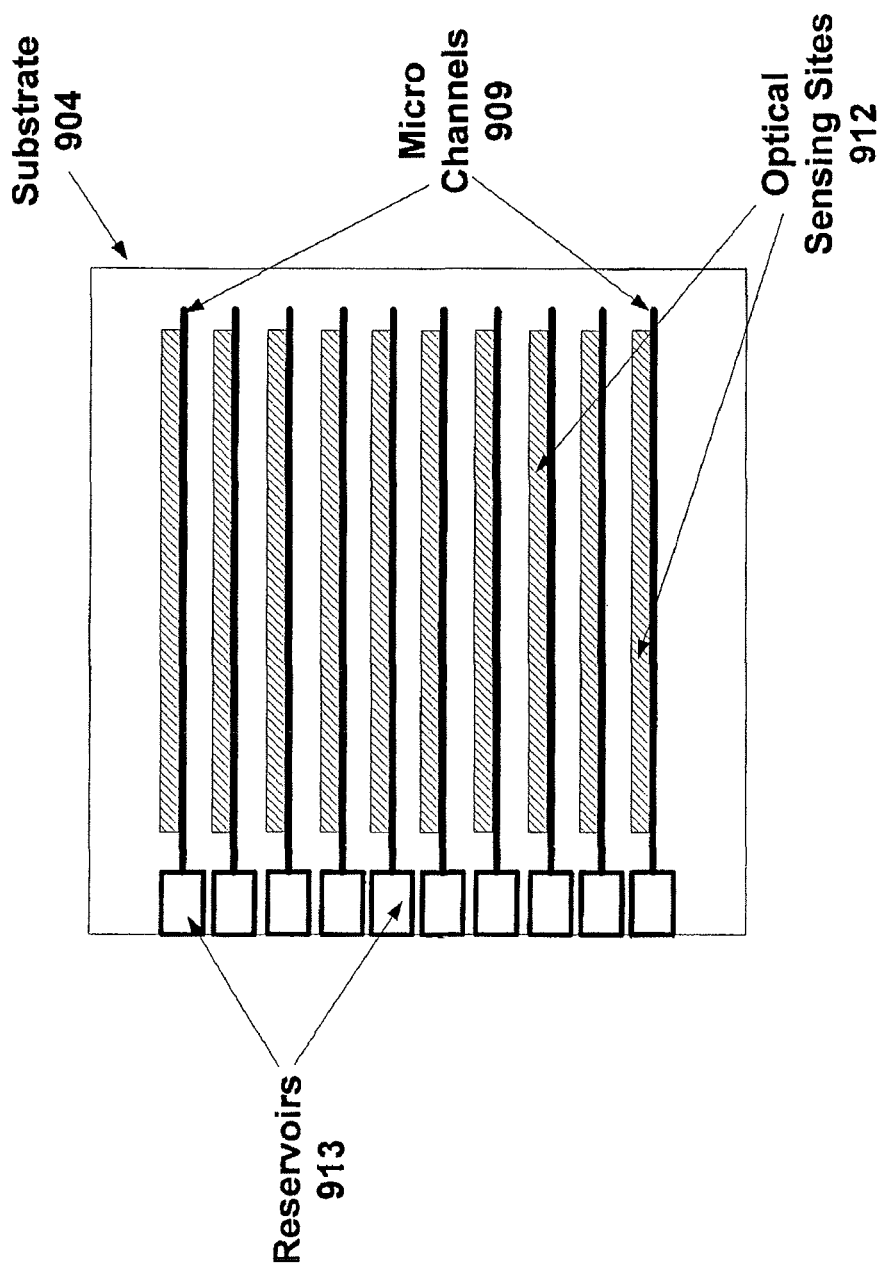
FIG. 9K is a schematic of another embodiment of the substrate of the invention including reservoirs and micro channels in relation to optical sensing sites.

FIG. 9K illustrates yet another embodiment of substrate 904 of the invention wherein substrate 904 additionally includes reservoirs 913 and microchannels 909 in relation to optical sensing sites 912. As such, in this embodiment microfluidics are incorporated into the substrate. Microfluidics can be adapted to drive liquid (in this case the tested sample) using the capillary effect across the substrate. As illustrated in FIG. 9K, this can be achieved by an arrangement of microchannels 909, optionally of varying width, which force the sample from one or more reservoirs 913 to optical sensing sites 912 which can include etched wells to receive the sample. The microchannels can be either etched on the face of the chip itself or can be added as an external structure on a surface of the substrate 904.

In use, it is envisioned that a sample to be tested can be pipetted into a reservoir at one end of the substrate. The sample can then be distributed using the microfluidic system to the optical sensing sites and sensing wells where it is allowed to bind to pre-spotted probes and can subsequently be optically detected and analyzed. Several reservoirs may be used to separate different samples/patients or for running several parallel tests.

The substrate of the system may be dip-coated with one or more probes configured to interact biochemically with a desired biologically active analyte molecule. Example 1 describes chip coating protocols for antibody or oligonucleotide attachment.

Additionally, it is envisioned that one or more probes may be applied to a sensor of the optical sensing sites using a print head. Furthermore, it is envisioned that delivery of sample to the optical sensing sites of the system comprises delivering the sample using an assay head. One possible print head technology is described in U.S. patent application Ser. No. 11/241,060, filed on Sep. 30, 2005, and U.S. patent application Ser. No. 11/632,086, filed on Jul. 6, 2005.

Figure 10A:
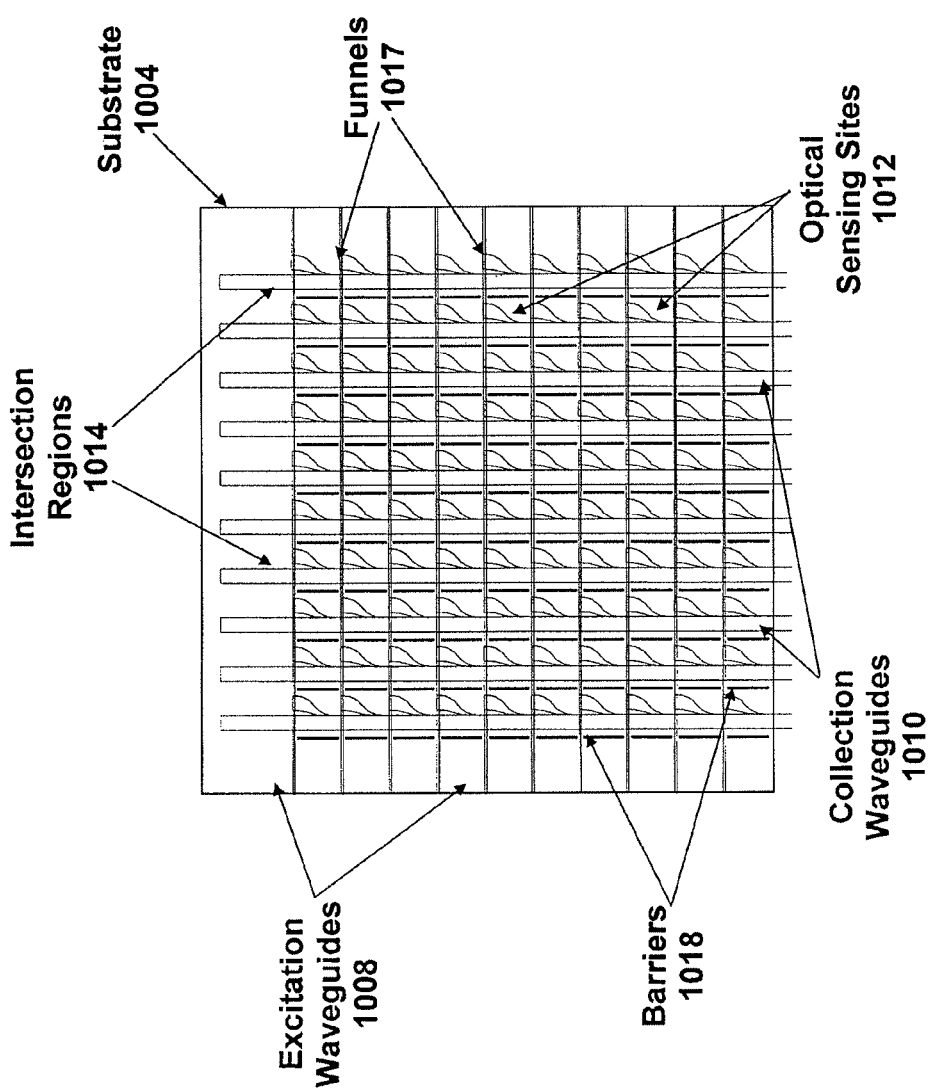
FIG. 10A is a schematic of the substrate of the invention including excitation and collection optical waveguides in conjunction with optical sensing sites, barriers and funnels.

FIG. 10A in a top view illustrates an exemplary substrate 1004 of the system of the invention wherein the collection waveguides 1010 include funnels 1017 (shown in detail in FIG. 10B) for collecting light.

As shown in the example in FIG. 10A, the substrate 1004 can include a 10×10 array consisting of 10 excitation waveguides 1008 (e.g., about 5 µm wide by about 2 µm deep), 10 collection waveguides 1010 (e.g., about 30 µm wide by about 10 µm deep), 100 optical sensing sites 1012 (e.g., wells about 30 µm long by about 5 µm wide by about 10 µm deep), 100 funnels 1017 for collecting light from the optical sensing sites 1012 and barriers 1011 (e.g., light absorbing channels) to reduce crosstalk between the optical sensing sites 1012. Although the example shown in FIG. 10A includes a 10×10 array of excitation waveguides 1008 and collection waveguides 1010, it is envisioned that the substrate can include greater than 10, greater than 100 or greater than 1,000 excitation waveguides 1008 and collection waveguides 1010.

In the embodiment shown in FIG. 10A, excitation light can be coupled into one or more excitation waveguides 1008 on the left hand side of the substrate 1004 from, for example, a scanning light source chip. Excitation light can travel along the excitation waveguides 1008 and couple into the optical sensing sites (e.g., wells) through an evanescent field tail. Excited fluorescence generated in the optical sensing site 1012 can be collected along the long facet of the optical sensing site 1012 into the funnels 1017. The funnels 1017 can channel the light into the collection waveguides 1010. The light in the collection waveguides 1010 can be coupled out at the "bottom" of the substrate 1004 into a detector array (not shown). Light scattered outside the optical sensing sites 1012 can be blocked by a series of barriers 1011 (e.g., light absorbers) to avoid crosstalk between parallel collection waveguides 1010.

In one embodiment, the substrate shown in FIG. 10A includes two waveguide layers. As illustrated in cross-sectional view in FIG. 10C, a bottom layer, about 2 µm thick, can include the excitation waveguide 1008. The bottom layer can have a higher refractive index in order to increase the evanescent field tail presence in the optical sensing sites. An upper layer, about 10 µm thick, can contain the optical sensing site and the light collection structures (funnels and waveguides). The upper layer can have a lower refractive index than the bottom layer in order to minimize light loss when coupling the light out of the substrate to the detector.

In a particular embodiment of the above, both the excitation and collection waveguides are multimode.

Figure 10B:
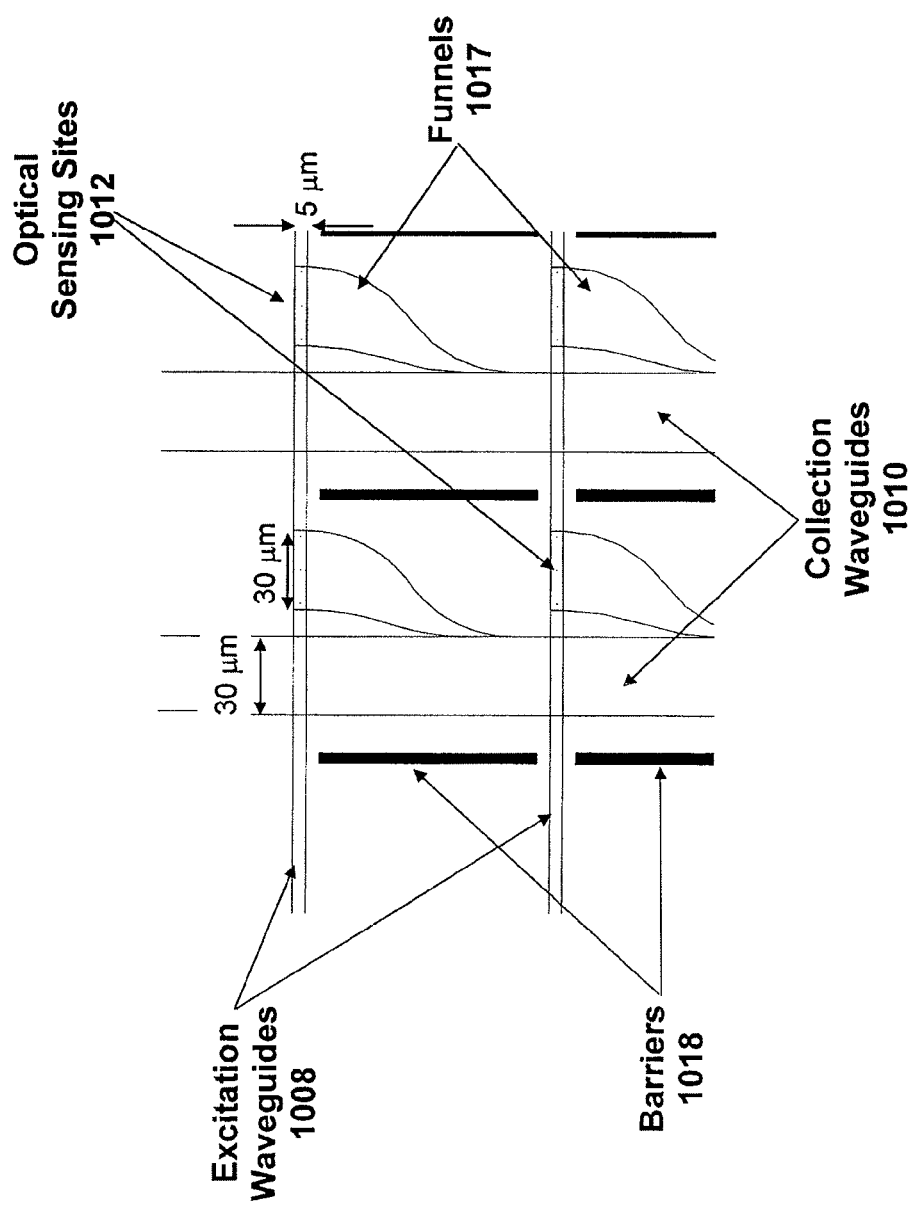
FIG. 10B is a schematic showing an enlarged view of substrate features according to an embodiment as shown in FIG. 10A.
Figure 10C:
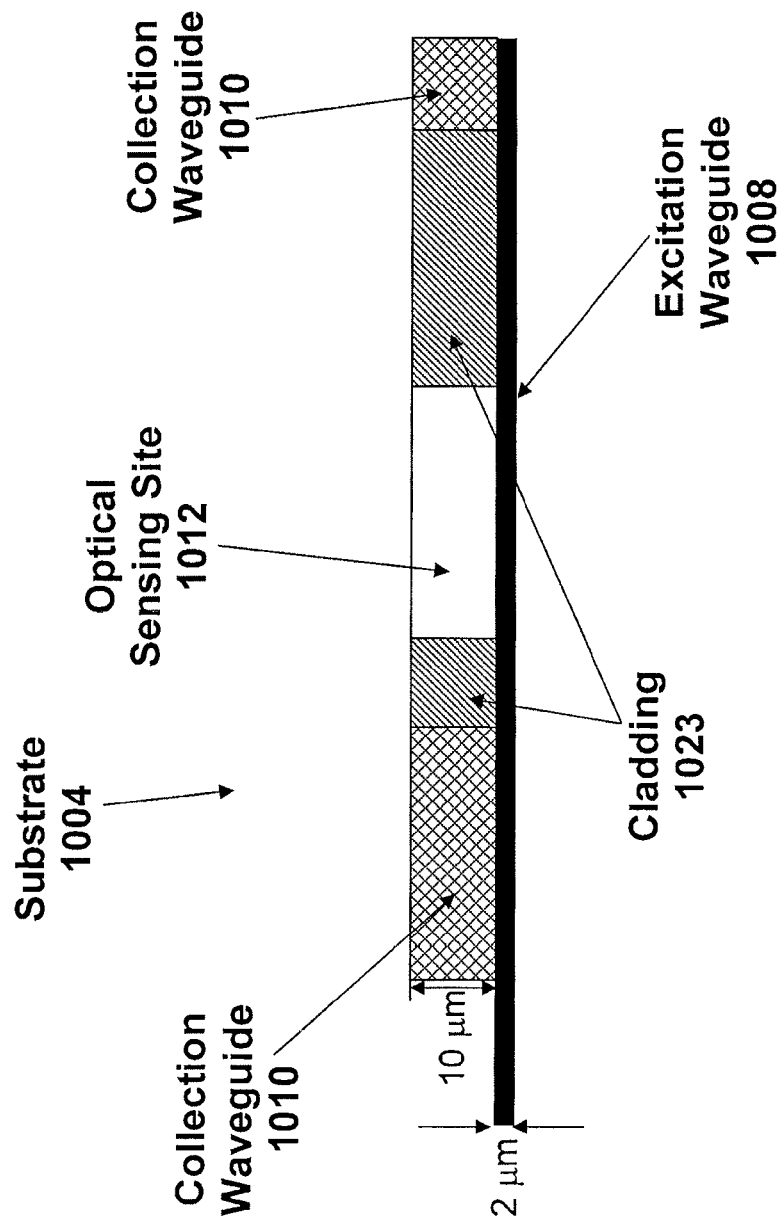
FIG. 10C is a schematic of a cross-sectional view of the substrate according to one embodiment.

As shown in cross-sectional view in FIG. 10C, in order to minimize the loss of light at the waveguide crossing points due to light coupling from the collection waveguides 1010 into the excitation waveguides 1008, the excitation waveguides 1008 can be thinner than the collection waveguides 1010. For example, as shown in FIGS. 10B and 10C, the excitation waveguides 1008 can have a width of about 5 µm (see FIG. 10B) and a height of about 2 µm (see FIG. 10C). As further shown, the collection waveguides 1010 can have a width of about 30 µm (see FIGS. 10A and 10B) and a height of about 10 µm (see FIG. 10C).

It is envisioned that light coupled at the waveguide crossing points between the excitation waveguides and the collection waveguides can shine directly into the optical sensing sites, thereby increasing light excitation rather than being lost.

As shown in FIG. 10B, the optical sensing sites can be wells that are narrow (about 5 µm) and long (about 30 µm) with light collectable along the long facet. Such a configuration increases the efficiency of light collection. In addition, light excitation coupling into the well can increase due to the long coupling length. The well dimensions (5×30×10 µm³) yield a volume of 1.5 pico-liter. Larger wells are also envisioned in a variety of sizes yielding volumes ranging from about 0.1 pico-liter to about 100 micro-liter.

The funnel can have a radius for the collection, confinement and coupling of light into the collection waveguides. Suitable ranges for radii can include from about 100 µm to about 1000 µm.

The barriers 1011 as illustrated in FIGS. 10A and 10B, can be trenches filled with light absorbing material (e.g., a metal such as gold). Where the barriers 1011 are trenches, the trenches can include openings above the excitation waveguide 1008 to avoid loss at the crossing points (not shown).

The overall dimensions of the substrate illustrated in FIG. 10A can be about 1.2 by about 1.2 mm². Margins can optionally be included around the substrate to adjust the overall dimensions as desired.

Figure 11A:
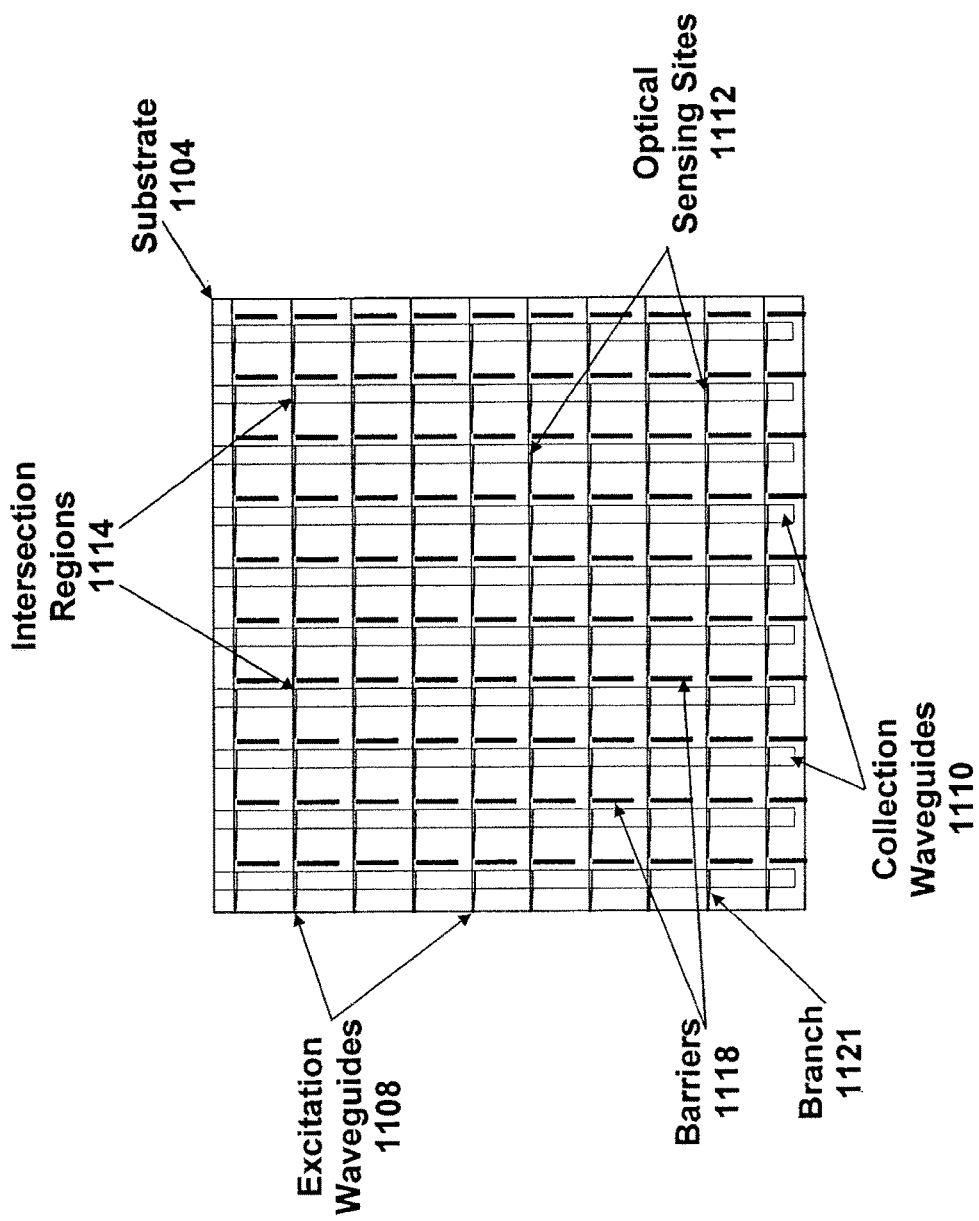
FIG. 11A is a schematic of one embodiment of the substrate of the invention including excitation and collection optical waveguides in conjunction with optical sensing sites, barriers and branches.

FIG. 11A illustrates an exemplary substrate 1104 of the system of the invention wherein the excitation waveguides 1108 include a plurality of branches 1121 (shown in detail in FIG. 11B) for tapping light from the excitation waveguides and coupling it into the sensing wells.

Figure 11B:
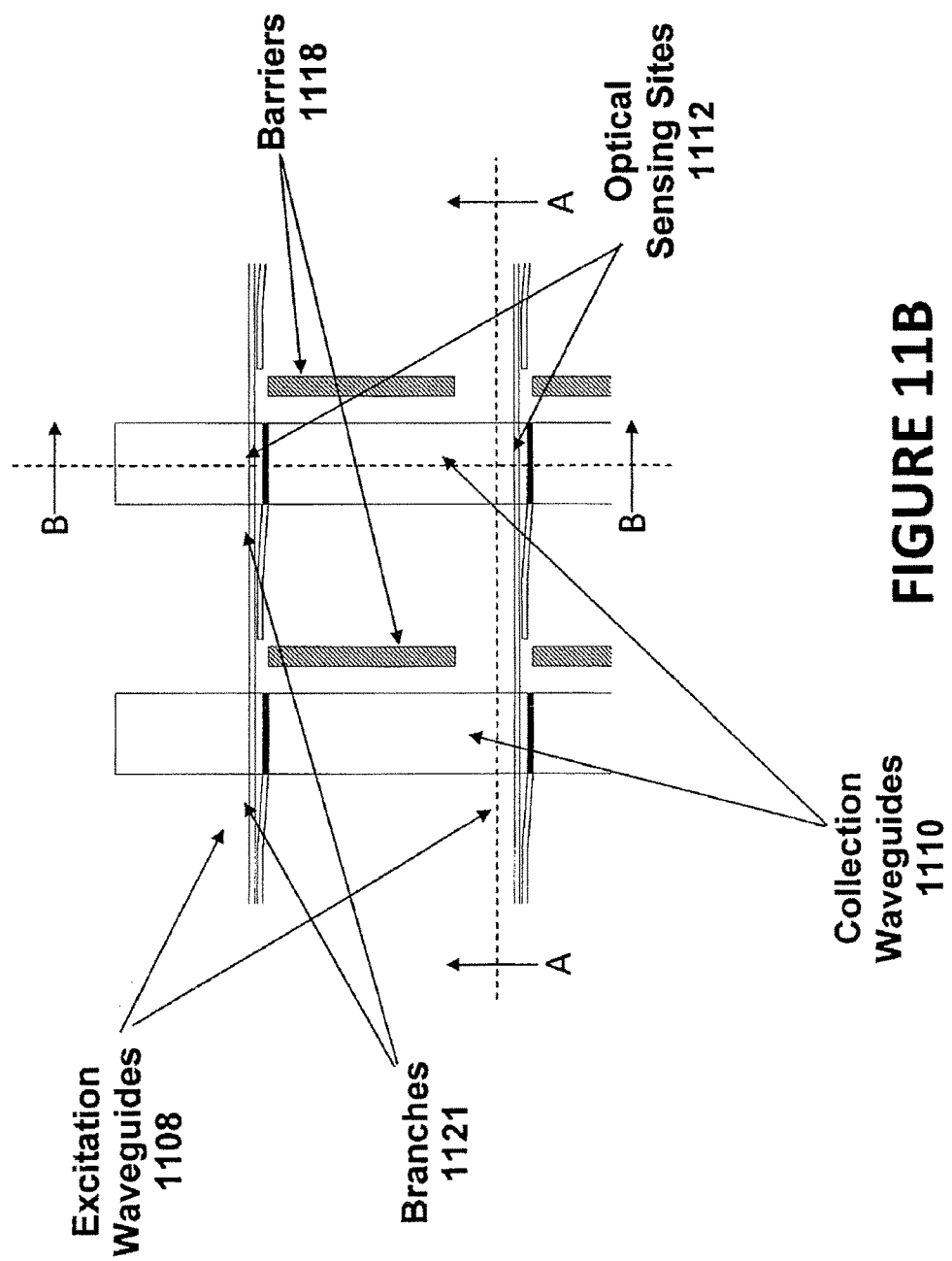
FIG. 11B is a schematic showing an enlarged view of substrate features according to an embodiment as shown in FIG. 11A.
Figure 11C:
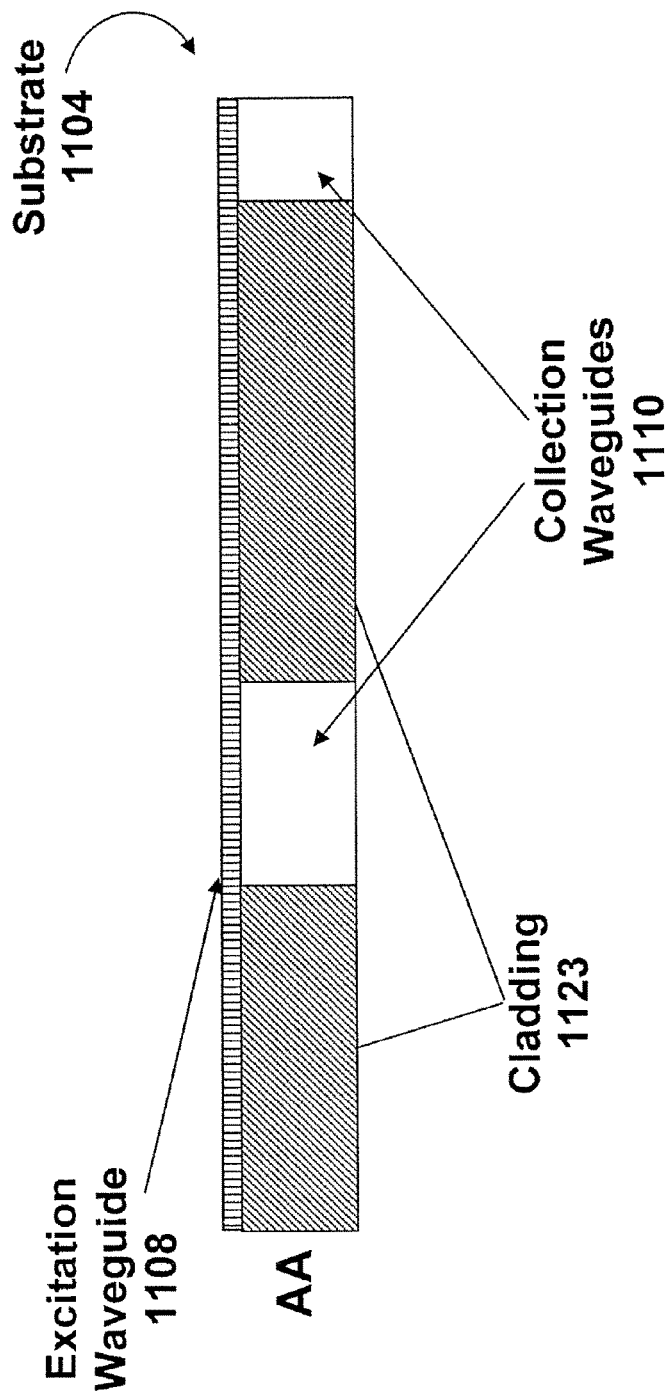
FIG. 11C is a schematic of a cross-sectional view in a plane (AA) of the substrate according to one embodiment.
Figure 11D:
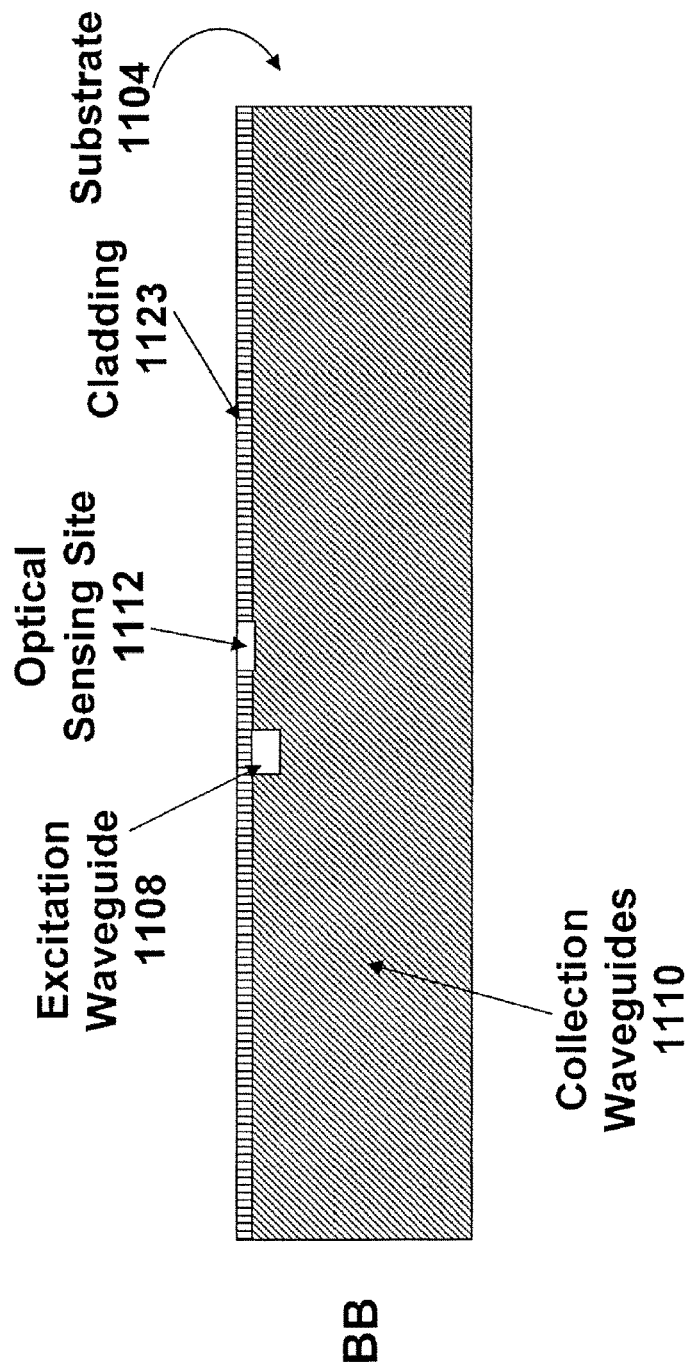
FIG. 11D is a schematic of a cross-sectional view in a plane (BB) of the substrate according to one embodiment.

In the embodiment shown in FIG. 11A, the substrate 1104 can be made up of several waveguide layers (e.g., three waveguide layers). Such a configuration can be useful, for example, to optimize excitation and fluorescence collection while minimizing loss and crosstalk. FIGS. 11C and 11D are schematic cross-section views of the substrate 1104 through planes at (AA) and (BB) respectively as indicated in FIG. 11B.

In one embodiment the substrate consists of three waveguide layers having core refractive index of 1.7 and clad reflective index of 1.4. Useful core refractive index values range from about 1.45 to about 2.1, and useful clad refractive index values range from about 1.4 to about 1.5.

As shown in FIGS. 11C and 11D, in one embodiment where the substrate 1104 includes three waveguide layers, a first bottom layer can be about 10 µm thick and include the collection waveguides 1110. In the embodiment illustrated in FIG. 11A, the collection waveguides 1110 can be about 30 µm wide, multimode and traverse the substrate 1104 from substantially edge to edge. A second middle waveguide layer can be about 0.5 µm to about 1 µm thick and include coupling waveguide branches 1121 (see FIGS. 10A and 10B). The branches 1121 can couple excited light into the optical sensing sites, which can be wells. A third top layer can be about 2 µm thick and include single-mode excitation waveguides 1108 and traverse the substrate 1104 substantially from edge to edge.

Figure 14A:
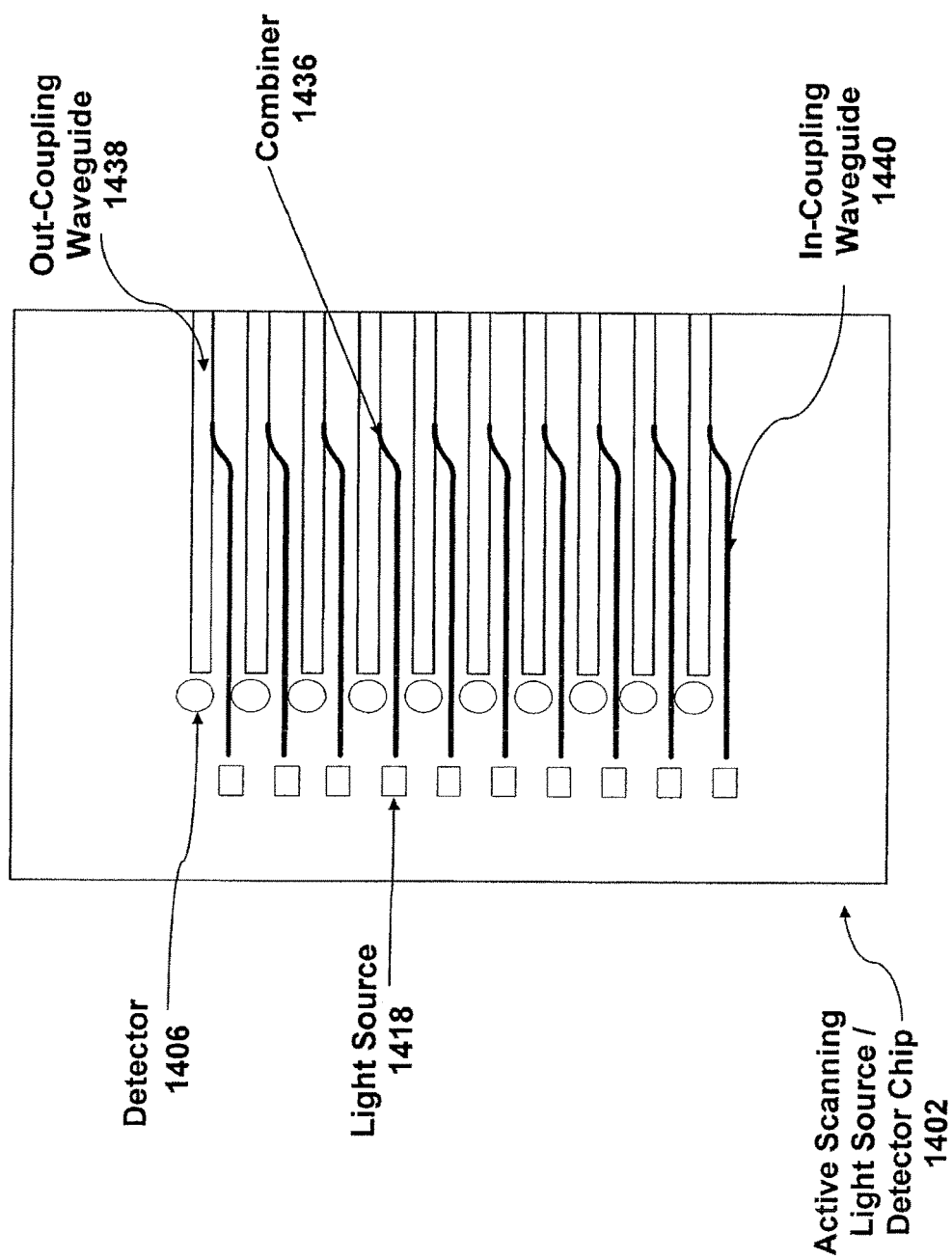
FIG. 14A is a schematic of an active scanning light source chip of the invention according to one embodiment including light source elements and optical in-coupling waveguides.

FIG. 14A illustrates an active scanning light source chip 1402 of the first embodiment (see FIG. 7A) of the detection system of the current invention. The active scanning light source chip 1402 includes light source elements 1418 and in-coupling waveguides 1440. A primary light wave generated by the light source elements is coupled from left into in-coupling waveguides 1440. Waveguides 1440 guide the primary light wave to the right edge of the active scanning light source chip 1402 and couple it out to the substrate (not shown).

Figure 14B:
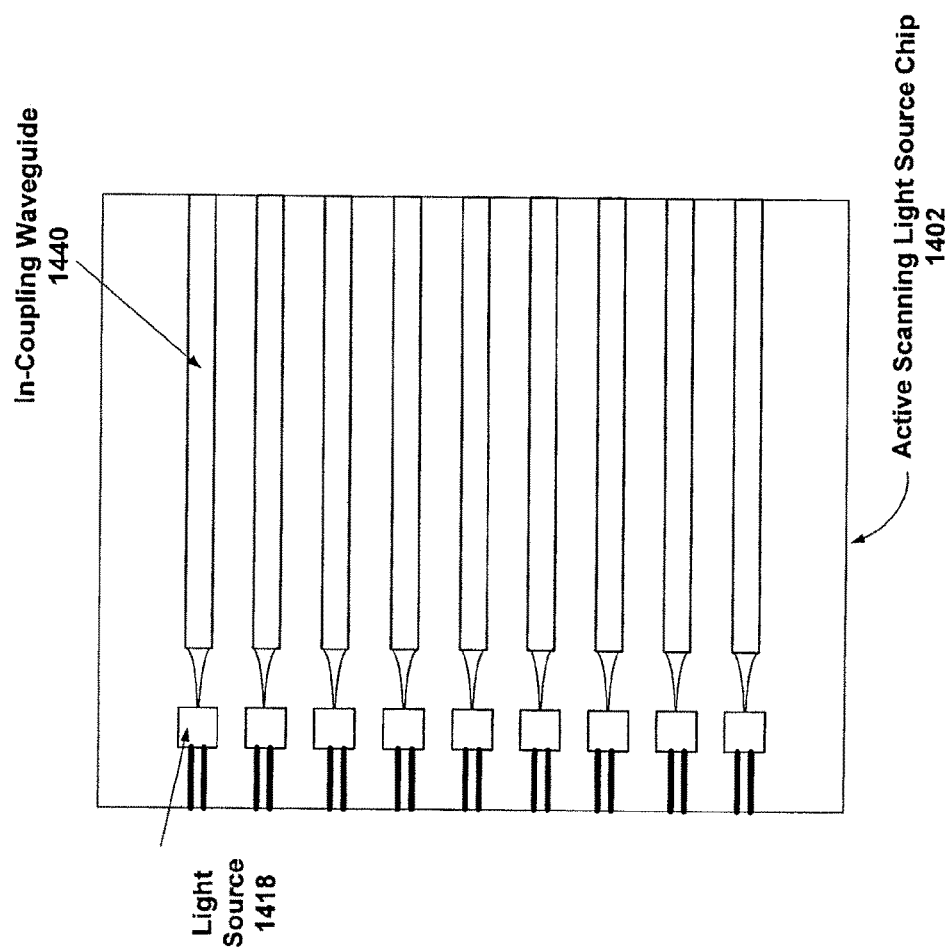
FIG. 14B is a schematic of an active scanning light source/detector chip of the invention according to one embodiment including light source elements, detector elements, optical in-coupling and out-coupling waveguides and optical combiners.

FIG. 14B illustrates an active scanning light source/detector chip 1402 of the second embodiment (see FIG. 7B) of the detection system of the current invention. The active scanning light source/detector chip 1402 includes light source elements 1418, detector elements 1416, in-coupling waveguides 1440, out-coupling waveguides 1438 and combiner 1436. A primary light wave (excitation light) generated by the light source 1418 is coupled from left into in-coupling waveguides 1440. The excitation light is then combined by combiners 1436 into out-coupling waveguides 1438 which then guide it to the right edge of active scanning light source/detector chip 1402 and couple it out to the substrate (not shown). The substrate (not shown) couples back the secondary light wave (collected at the optical sensing sites—not shown) to out-coupling waveguides 1438 at the right edge of active scanning light source/detector chip 1402. The secondary light wave is guided by the out-coupling waveguides 1438 to the detector elements 1416 on the active scanning light source/detector chip.

Figure 12A:
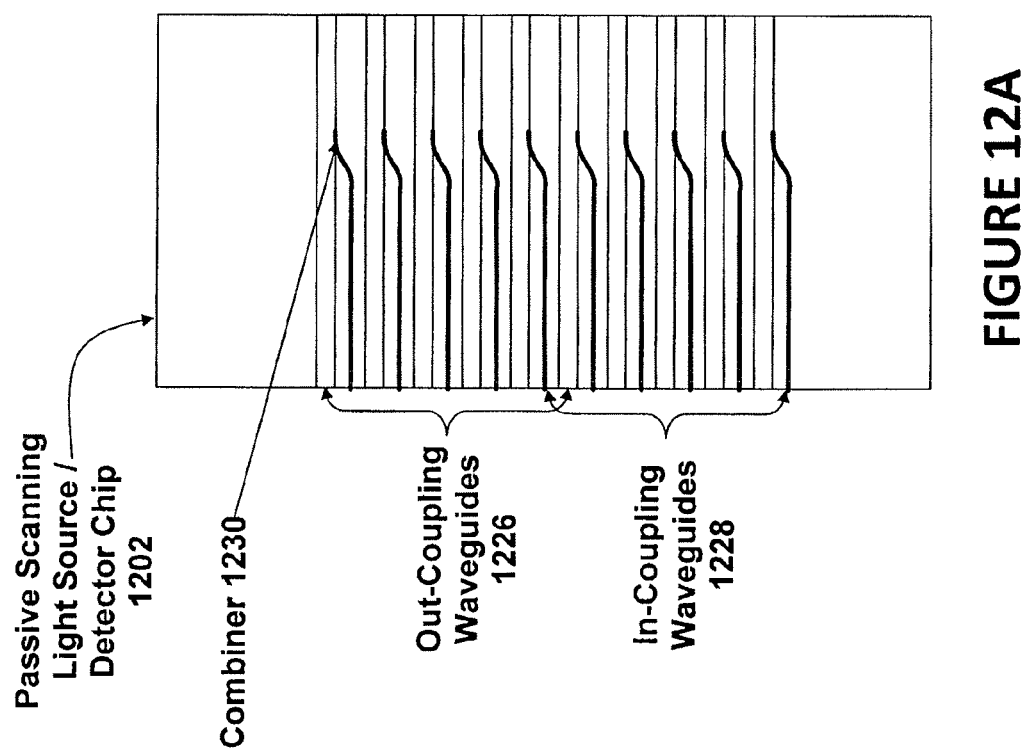
FIG. 12A is a schematic of a passive scanning light source chip of the invention according to one embodiment including optical in-coupling waveguides.

FIG. 12A illustrates a passive scanning light source chip 1202 of the third embodiment (see FIG. 7C) of the detection system of the current invention. Passive scanning light source chip 1202 includes in-coupling waveguides 1228. A primary light wave (excitation light) is coupled from left into in-coupling waveguides 1228 through a set of optical fibers (not shown). Waveguide 1228 guides the primary light wave to the right edge of the passive scanning light source chip 1202 and couples it out to the substrate (not shown).

Figure 12B:
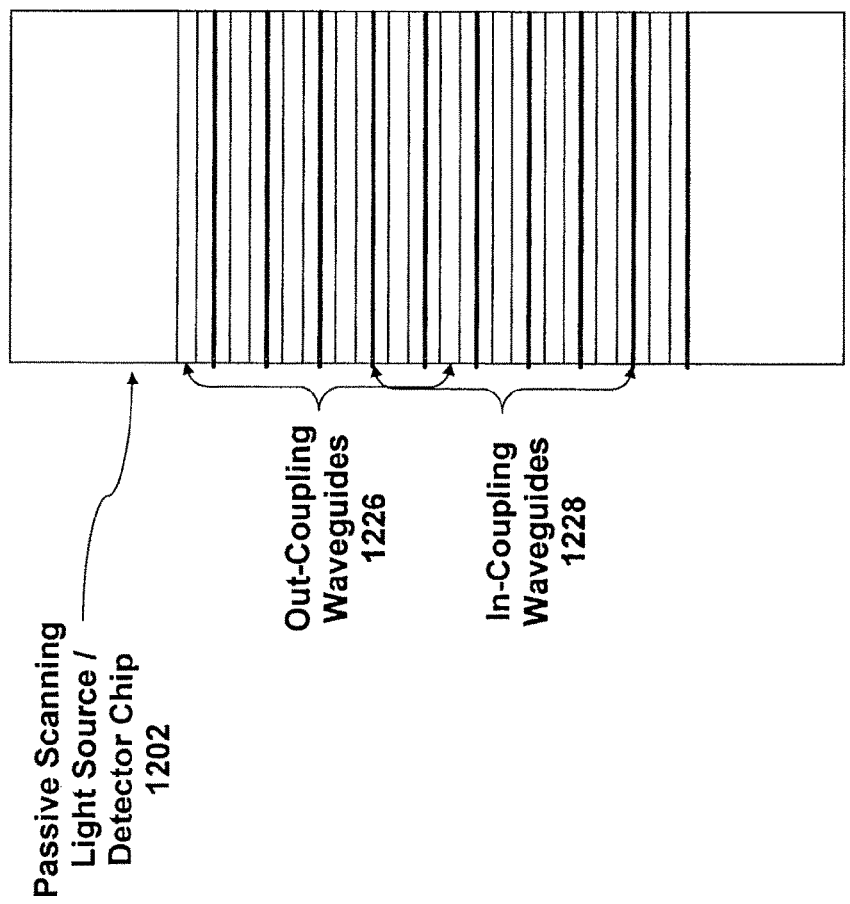
FIG. 12B is a schematic of a passive scanning light source/detector chip of the invention according to one embodiment including optical in-coupling and out-coupling waveguides and optical combiners.

FIG. 12B illustrates a passive scanning light source/detector chip 1202 of the fourth embodiment (see FIG. 7D) of the detection system of the current invention. The passive scanning light source/detector chip 1202 includes in-coupling waveguides 1228, out-coupling waveguides 1226 and combiners 1230. A primary light wave (excitation light) is coupled from the left into in-coupling waveguides 1228 through a set of optical fibers (not shown). The excitation light is then combined by combiners 1230 into the out-coupling waveguides 1226 which then guide it to the right edge of passive scanning light source/detector chip 1202 and couple it out to the substrate (not shown). The substrate (not shown) couples back the secondary light wave (collected at the optical sensing sites—not shown) to out-coupling waveguides 1226 at the right edge of passive scanning light source/detector chip 1202. The secondary light wave is guided by waveguides 1226 from right to left and is coupled out of passive scanning light source/detector chip 1202 at its left edge to the detector (not shown) through a set of optical fibers (not shown).

FIG. 12C illustrates a second possible design of a passive scanning light source/detector chip 1202 of the fourth embodiment (see FIG. 7D) of the detection system of the current invention. The passive scanning light source/detector chip 1202 includes in-coupling waveguides 1228 and out-coupling waveguides 1226. A primary light wave (excitation light) is coupled from left into in-coupling waveguides 1228 through a set of optical fibers (not shown). The excitation light is then guided to the right edge of passive scanning light source/detector chip 1202 where it is coupled out to the substrate (not shown). The substrate (not shown) couples back the secondary light wave (collected at the optical sensing sites—not shown) to out-coupling waveguides 1226 at the right edge of passive scanning light source/detector chip 1202. The secondary light wave is guided by waveguides 1226 from right to left and is coupled out of passive scanning light source/detector chip 1202 at its left edge to the detector (not shown) through a set of optical fibers (not shown).

It is envisioned that the light source elements 718 in FIGS. 7A-1D (or 1418 in FIGS. 14A and 14B) can comprise a dynamic light source allowing for selective and programmed generation of the primary light wave in one or more individual elements.

In some embodiments, the light source elements 718 can provide variable wavelengths of light. In one embodiment, the light source element is a broad-band source. In another embodiment, the light source element is a tunable source.

In some embodiments, the number of light source elements 718 will be equal to the number of excitation waveguides in the substrate of the system. The interface between the scanning light source outputs should match, in terms of pitch, the excitation waveguides in the substrate to allow these two elements at some point along the scanning path to efficiently couple and transfer light from the scanning light source chip to the excitation waveguides or to the in-coupling waveguides of the substrate.

The light source elements depicted in FIGS. 7A-D and FIGS. 14A and 14B can include different types of light generating elements. In some embodiments, the light generator elements are light emitting diodes (LEDs). In other embodiments the light generator elements are laser diodes (LDs). Each individual light generator element is separately controlled and can be turned on or off as desired. In one embodiment the scanning light source chip includes 10 or more light generator elements. In another embodiment the scanning light source chip includes 100 or more light generator elements. In yet another embodiment the scanning light source chip includes 1000 or more light generator elements. In a further embodiment the scanning light source chip includes between 10 and 100 light generator elements.

The detector elements depicted in FIGS. 7A-D and FIGS. 14A and 14B can include different types of detector elements. In some embodiments, the detector elements are PIN diodes. In some embodiments the detector elements are avalanche photo-diodes (APD). In some embodiments the detector elements are a group of pixels which are part of a CCD array. Each individual detector element is separately controlled and read. In one embodiment the scanning light source chip includes 10 or more detector elements. In another embodiment the scanning light source chip includes 100 or more detector elements. In yet another embodiment the scanning light source chip includes 1000 or more detector elements. In a further embodiment the scanning light source chip includes between 10 and 100 detector elements.

In one non-limiting example, the detector element has a spectral range of between 400 to 1000 nm, a photosensitivity (A/W) of >0.3, an active area per element of 0.005 mm$^2$, 128 elements, and a pitch of <0.1 mm.

In one embodiment, the detector is a silicon photodiode (PN, PIN, CCD or APD) array. An example of a suitable detector array is the Hamamatsu 64×2048 CCD chip (PN—S10420-1106).

In some embodiments, the light source elements and detector elements on the scanning light source chip can be integrated on a single chip which includes an array of two or more light source elements, an array of two or more detector elements, an array of two or more in-coupling waveguides, an array of two or more out-coupling waveguides and an array of two or more combiners. In one implementation each light source element is optically coupled to one in-coupling waveguide and adapted such that most of the light emitted by the light generator element propagates along that waveguide. The waveguides can extend to the edge of the chip where they can be brought at some point along the scanning path of the chip to couple the light propagating within them to the substrate. In one implementation two light source elements, each optionally emitting at a different wavelength can be coupled to a single in-coupling waveguide. In another implementation more than two light source elements, each optionally emitting at a different wavelength can be coupled to a single in-coupling waveguide.

In other embodiments, the light source elements on the scanning light source chip can be integrated on a single chip which includes an array of two or more light source elements and an array of two or more waveguides. In one implementation each light source elements is optically coupled to one waveguide and adapted such that most of the light emitted by the light source element propagates along the waveguide. The waveguides can extend to the edge of the chip where they can be brought to couple the light propagating within them to the substrate. In one implementation two light source elements, each optionally emitting at a different wavelength can be coupled to a single waveguide. In another implementation more than two light source elements, each optionally emitting at a different wavelength can be coupled to a single waveguide.

The scanning light source chip can include, in addition to light source elements, detector elements and waveguides, light manipulating features such as lenses, filters, switches, modulators, splitters, combiners, mirrors and circulators.

The control of the scanning light source chip can be either integrated on the same chip as the light source elements, detector elements and waveguides or alternatively can be external to the chip. The scanning light source chip can have an electrical interface to an external driver or external controller or logic interface to an external control system. The control of the light source elements and detector elements allows driving each light source element and each detector element separately. It further allows also control of the other features present on the scanning light source chip such as, for example, the modulators and switches.

Additional elements useful in planar lightwave circuits, including but not limited to couplers, filters, mirrors, circulators, splitters, modulators, switches and trenches are envisioned as part of the system described herein (not shown). Such elements when integrated into the substrate or into the scanning light source chip can serve to manipulate the incoming first light waves in the in-coupling waveguides or outgoing second light waves in the out-coupling waveguides. In other embodiments, such elements when integrated into the substrate or into the scanning light source chip can serve to manipulate both incoming first light waves in the excitation waveguides or outgoing second light waves in the collection waveguides.

A range of dimensions for the various features described herein include: waveguides thickness—about 20 nm to about 50 µm; waveguide width—about 1 µm to about 500 µm; waveguide length—about 1 mm to about 100 mm; optical sensing site length—about 100 µm to about 100 mm; optical sensing site width—about 1 µm to about 500 µm; optical sensing site depth—about 0 µm to about 20 µm; waveguide pitch—about 10 µm to about 10 mm; substrate thickness—about 100 µm to about 5 mm; upper cladding thickness—about 0 µm to about 20 µm; and lower cladding thickness—about 0.1 µm to about 20 µm.

The substrate of the detection system can made up of any of a number of well known materials suitable for use in planar lightwave circuits. For example, useful substrate materials include but are not limited to silica (SiO2), glass, epoxy, lithium niobate and indium phosphide as well as combinations thereof. The waveguides disclosed herein can be made up of silicon, silica (SiO2) and derivatives thereof, silicon oxynitride (SiON) and derivatives thereof, silicon nitride (SiN) and derivatives thereof, tantalum oxide ($TaO_x$) and its derivatives thereof, polymers, lithium niobate and indium phosphide as well as combinations thereof. In one embodiment, UV light is used to change the refractive index of a waveguide material after deposition.

Figure 13A:
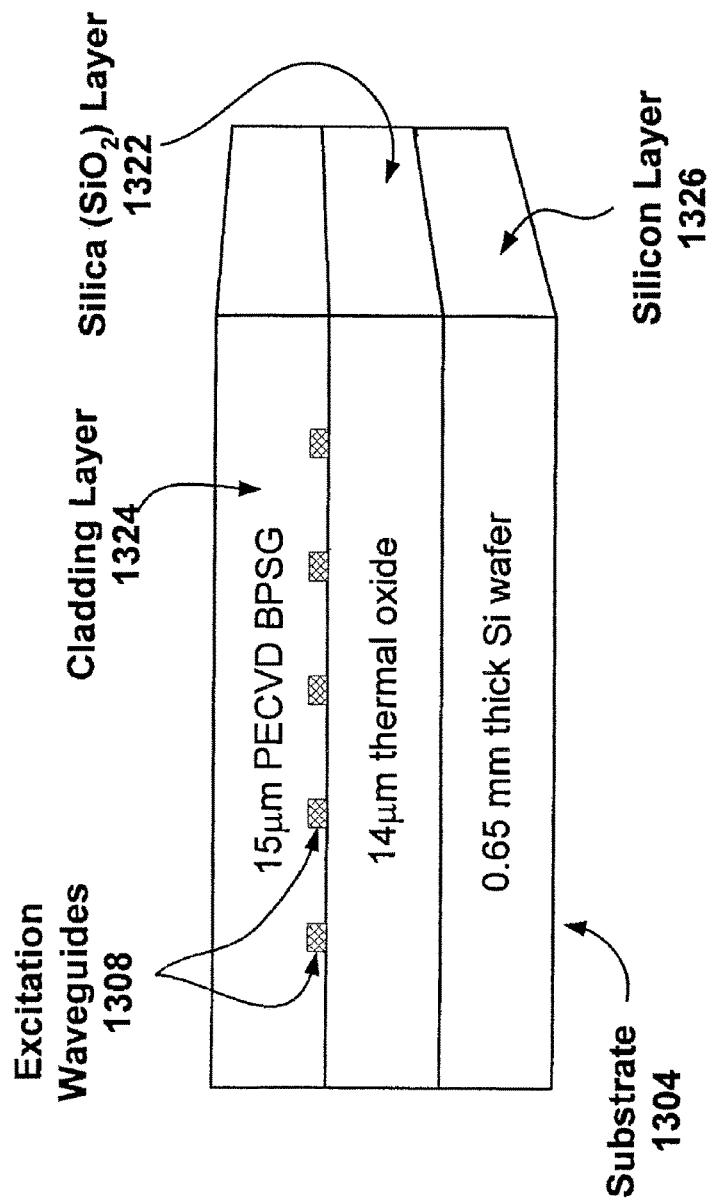
FIG. 13A is a schematic of a general substrate including typical layers and waveguides representative of those of the current invention.

FIG. 13A illustrates an exemplary silicon layer 1326 of the substrate 1304. For example, the silicon layer 1326 can be made up of a silicon wafer having a thickness from about 0.1 mm to about 10 mm. In another example the silicon wafer can have a thickness from about 0.3 to about 1 mm. In a particular example as illustrated in FIG. 13A, the silicon wafer has a thickness of 0.65 mm. As shown in FIG. 13A in one embodiment, the silica (SiO2) layer 1322 is a 14 µm thermal oxide layer of silica (SiO2) created by placing the silicon in an oxygen-rich environment inside a furnace at high temperature. The top silicon layer oxidizes over time (several hours) creating a SiO2 layer. Additionally, as shown in FIG. 13A, in one embodiment, the cladding layer 1324 is 15 µm thick and deposited by a PECVD (Plasma-Enhanced Chemical Vapor Deposition) process after etching to produce the waveguides 1308.

It is envisioned that the various layers of the substrate can include different refraction index properties. For example, a waveguide layer (e.g. SiN) has a higher refraction index than a cladding layer of silica deposited thereon.

Figure 13B:
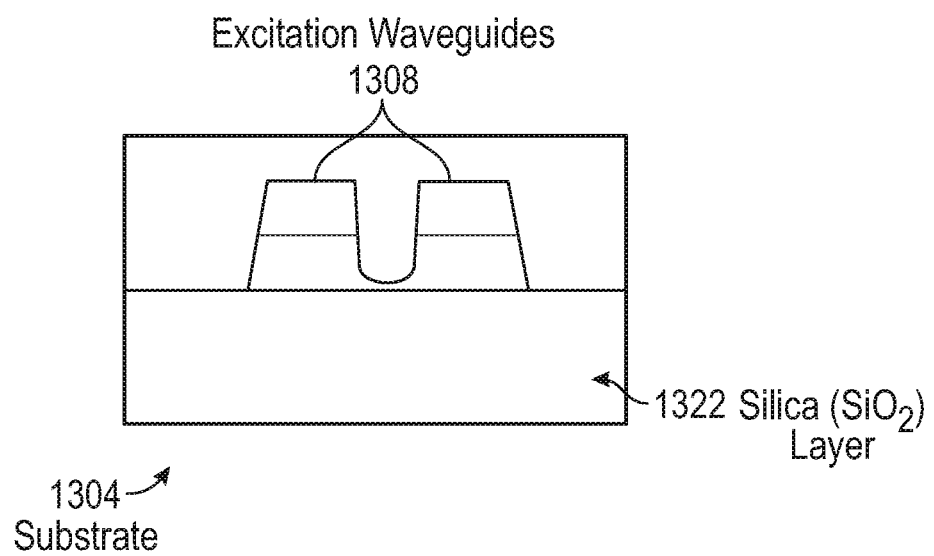
FIG. 13B is a photomicrograph image of waveguides representative of those of the invention and a silica layer.
Figure 13C:
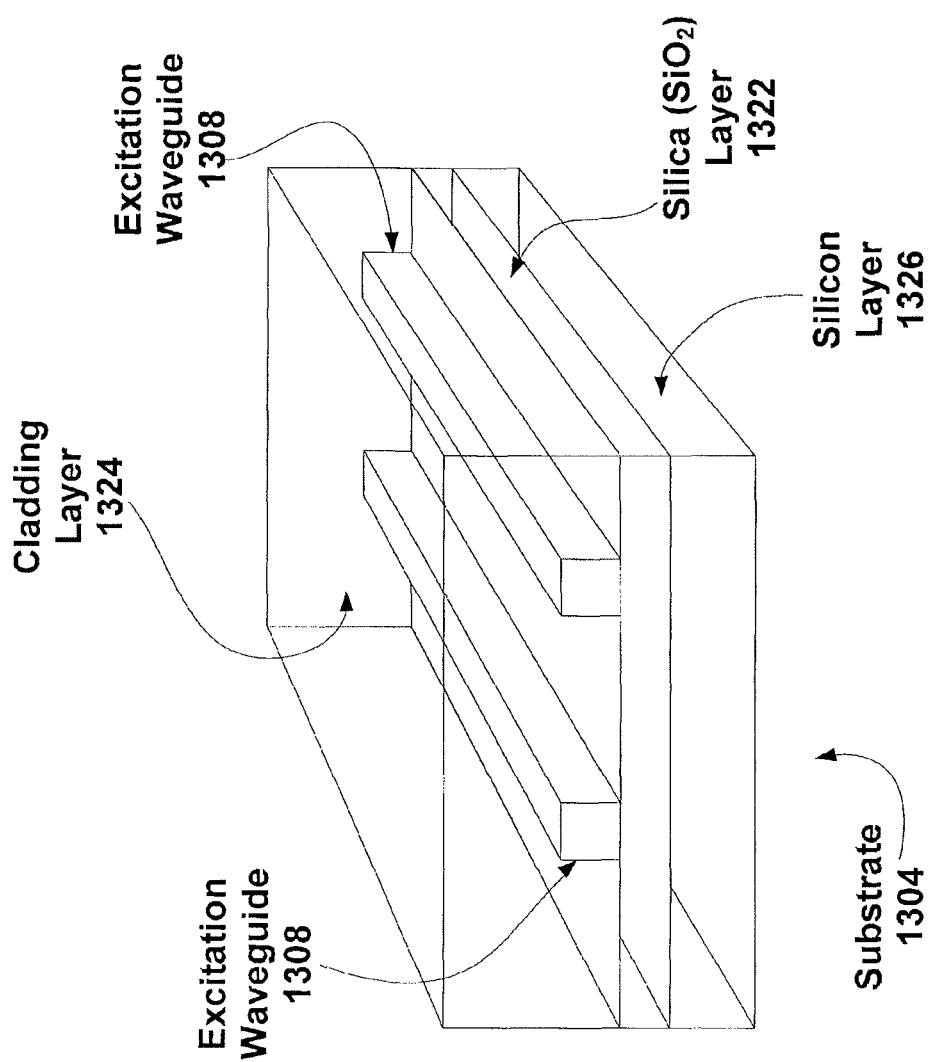
FIG. 13C is a perspective view of waveguides and associated substrate layers.

As shown in FIG. 13B (illustrated with a photomicrograph prior to deposition of a cladding layer), in some embodiments, the substrate 1304 can include two waveguides 1308 arranged for light wave coupling on a silica (SiO2) layer 1322. Alternatively, as shown in FIG. 13C, two waveguides 1308 can be arranged for guiding uncoupled light waves on a silica (SiO2) layer 1322 and over-clad with a cladding layer 1324.

The optical sensing sites in one embodiment are in the form of wells, for example, etched wells (see FIG. 9C cross-section view). Where the optical sensing site is a well, it can act as a vessel for a liquid sample. In another embodiment the optical sensing sites are a region on the surface of the substrate, for example, above the waveguides. In a further embodiment, the optical sensing sites are biochemical interaction sites. For example, where the optical sensing site is a well containing a sensor single stranded DNA oligonucleotide having a fluorescent tag attached, a solution containing a target complementary single stranded DNA added to the well could biochemically interact by base-pairing with the sensor within the optical sensing site (not shown). In another example the optical sensing site is a location or well containing one or more immunoassay reagent for conducting an immunoassay as described herein.

In a particular embodiment, the optical sensing sites comprise optical transducers (not shown). An optical transducer is defined as any device that generates a measurable change (wavelength, amplitude or phase) to the incoming primary light wave which can thus be monitored in the outgoing secondary light wave. In one embodiment the optical transducers are fluorescence wells including fluorescent or luminescent compounds, wherein light waves guided by the waveguides excite the fluorescent or luminescent compound in the wells in the presence of a target, and the same waveguides collect and guide light emitted from the wells to the detector (possibly through an adapter chip), for example at the edge of the chip (not shown).

The sensor of the optical sensing site of the system can be a sensor that discriminates or interacts with a target (e.g., a biologically active analyte) in a sample from, for example, a biological, man-made or environmental source. As discussed above, a first lightwave can induce the sensor to transduce an optical signal to a second light wave. In one embodiment where the sensor is capable of discriminating or interacting with a target in a sample, a measurable change in the second light wave can result when the sensor discriminates or interacts with the target. Upon detection of the change in the second light wave using the detector of the system, the presence of the target in the sample is indicated.

Any of a number of sensors can be used with the detection system to measure phenomena associated with the sensing of a target in a sample. Examples of suitable sensors include, but are not limited to, a fluorescence well or cell, an absorption cell, an interferometric sensor, a diffractive sensor or a surface plasmon resonance (SPR) detector. For a fluorescence well or cell, the measurable phenomenon can be light emission from luminescent or fluorescent molecular tags. For example, emitted light at an altered wavelength can be measured. In the case of an absorption cell, changes in the sample optical density (OD) can measurably affect the intensity of the light passing through the sample. For an interferometric sensor, changes in the effective refractive index of a waveguide generate a phase difference between two light waves leading to different interference patterns measurable as a difference in intensity at the detector. For a diffractive sensor, changes in the effective refractive index at the surface of a diffractive element, for example, a grating, affect the diffraction angle of the light for a given wavelength or alternatively affect the wavelength at a given diffraction angle. In the case of an SPR sensor, changes in the effective refractive index at a metal-dielectric interface affect the resonance conditions for generating surface plasmons.

A control system for managing the different steps of operating the detection system is envisioned.

The control system can manage steps such as aligning and driving the scanning light source chip to scan the edge of the substrate, in addition to switching the light output from the light source, reading the detector array and reporting the results detected.

In general in one aspect, a method of using the systems and devices described herein to detect the presence of a single biologically active analyte molecule in a sample is provided. Biologically active analyte molecules in this context include any of the biologically active analyte molecules disclosed herein.

In practicing the methods of the present invention, many conventional techniques in molecular biology are optionally utilized. These techniques are well known and are explained in, for example, Ausubel et al. (Eds.) *Current Protocols in Molecular Biology, Volumes I II, and III*, (1997), Ausubel et al. (Eds.), *Short Protocols in Molecular Biology: A Compendium of Methods from Current Protocols in Molecular Biology*, 5th Ed., John Wiley & Sons, Inc. (2002), Sambrook et al., *Molecular Cloning: A Laboratory Manual*, 3rd Ed., Cold Spring Harbor Laboratory Press (2000), and Innis et al. (Eds.) *PCR Protocols: A Guide to Methods and Applications*, Elsevier Science & Technology Books (1990), all of which are incorporated herein by reference.

Sample preparation suitable for use with the system and methods described herein can include any of a number of well known methods for collection and analysis of biological and/or environmental samples. In the case of biological samples the sample can be, for example, manipulated, treated, or extracted to any desired level of purity for a target of interest.

The sample can be a bodily fluid suspected of containing a biologically active analyte. Commonly employed bodily fluids include but are not limited to blood, serum, saliva, urine, gastric and digestive fluid, tears, stool, semen, vaginal fluid, interstitial fluids derived from tumorous tissue, and cerebrospinal fluid.

It is anticipated that the systems described herein can be used for screening a large variety of samples. In the case where the investigated subject is a living creature, the sample may originate from body fluids as discussed. Methods of obtaining samples include but are not limited to cheek swabbing, nose swabbing, rectal swabbing, skin fat extraction or other collection strategies for obtaining a biological or chemical substance. When the tested subject is a non-living or environmental body, the sample may originate from any substance in a solid phase, liquid phase or gaseous phase. The sample may be collected and placed onto the substrate or the substrate may be directly exposed to the investigated sample source (e.g. water reservoir, free air) and interact with it.

In some embodiments, the bodily fluids are used directly for detecting one or more biologically active analyte present therein without further processing. Where desired however, the bodily fluids can be pre-treated before performing the analysis with the detection system. The choice of pre-treatments will depend on the type of bodily fluid used and/or the nature of the biologically active analyte under investigation. For instance, where the biologically active analyte is present at a low level in a sample of bodily fluid, the sample can be concentrated via any conventional means to enrich the biologically active analyte. Methods of concentrating a biologically active analyte include but are not limited to drying, evaporation, centrifugation, sedimentation, precipitation, and amplification. Where the biologically active analyte is a nucleic acid, it can be extracted using various lytic enzymes or chemical solutions according to the procedures set forth in Sambrook et al. ("Molecular Cloning: A Laboratory Manual"), or using nucleic acid binding resins following the accompanying instructions provided by manufactures. Where the biologically active analyte is a molecule present on or within a cell, extraction can be performed using lysing agents including but not limited to denaturing detergents such as SDS or nondenaturing detergents such as thesit (2-dodecoxyethanol), sodium deoxylate, Triton® X-100, and Tween® 20.

In some embodiments, pretreatment can include diluting and/or mixing the sample, and filtering the sample to remove, e.g., red blood cells from a blood sample.

Targets detectable using the detection system include but are not limited to, a biologically active analyte including a nucleic acid, a protein, an antigen, an antibody, a microorganism, a gas, a chemical agent and a pollutant.

In one embodiment, the target is a nucleic acid that is DNA, for example, cDNA. In a related embodiment, the DNA target is produced via an amplification reaction, for example, by polymerase chain reaction (PCR). In another embodiment of the subject invention, the detected biologically active analyte is a protein representing a known biomarker for a disease or specific condition of the investigated organism. In another embodiment several different biologically active analytes can be proteins provided as a panel of bio-markers wherein relative concentrations of the bio-markers are indicative for a disease or other condition of the investigated organism. In a further embodiment the target is a microorganism that is a pathogen. In another embodiment the target is a chemical agent, for example, a toxic chemical agent.

Where the target is a nucleic acid, it can be single-stranded, double-stranded, or higher order, and can be linear or circular. Exemplary single-stranded target nucleic acids include mRNA, rRNA, tRNA, hnRNA, ssRNA or ssDNA viral genomes, although these nucleic acids may contain internally complementary sequences and significant secondary structure. Exemplary double-stranded target nucleic acids include genomic DNA, mitochondrial DNA, chloroplast DNA, dsRNA or dsDNA viral genomes, plasmids, phage, and viroids. The target nucleic acid can be prepared synthetically or purified from a biological source. The target nucleic acid may be purified to remove or diminish one or more undesired components of the sample or to concentrate the target nucleic acids. Conversely, where the target nucleic acid is too concentrated for the particular assay, the target nucleic acid may be diluted.

Following sample collection and optional nucleic acid extraction, the nucleic acid portion of the sample comprising the target nucleic acid can be subjected to one or more preparative reactions. These preparative reactions can include in vitro transcription (IVT), labeling, fragmentation, amplification and other reactions. mRNA can first be treated with reverse transcriptase and a primer to create cDNA prior to detection and/or amplification; this can be done in vitro with purified mRNA or in situ, e.g. in cells or tissues affixed to a slide. Nucleic acid amplification increases the copy number of sequences of interest such as the target nucleic acid. A variety of amplification methods are suitable for use, including the polymerase chain reaction method (PCR), the ligase chain reaction (LCR), self sustained sequence replication (3SR), nucleic acid sequence-based amplification (NASBA), the use of Q Beta replicase, reverse transcription, nick translation, and the like.

Where the target nucleic acid is single-stranded, the first cycle of amplification forms a primer extension product complementary to the target nucleic acid. If the target nucleic acid is single stranded RNA, a polymerase with reverse transcriptase activity is used in the first amplification to reverse transcribe the RNA to DNA, and additional amplification cycles can be performed to copy the primer extension products. The primers for a PCR must, of course, be designed to hybridize to regions in their corresponding template that will produce an amplifiable segment; thus, each primer must hybridize so that its 3' nucleotide is paired to a nucleotide in its complementary template strand that is located 3' from the 3' nucleotide of the primer used to replicate that complementary template strand in the PCR.

The target nucleic acid can be amplified by contacting one or more strands of the target nucleic acid with a primer and a polymerase having suitable activity to extend the primer and copy the target nucleic acid to produce a full length complementary nucleic acid or a smaller portion thereof. Any enzyme having a polymerase activity that can copy the target nucleic acid can be used, including DNA polymerases, RNA polymerases, reverse transcriptases, and enzymes having more than one type of polymerase activity, and the enzyme can be thermolabile or thermostable. Mixtures of enzymes can also be used. Exemplary enzymes include: DNA polymerases such as DNA Polymerase I ("Pol I"), the Klenow fragment of Pol I, T4, T7, Sequenase® T7, Sequenase® Version 2.0 T7, Tub, Taq, Tth, Pfx, Pfu, Tsp, Tfl, Tli and *Pyrococcus* sp GB D DNA polymerases; RNA polymerases such as *E. coli*, SP6, T3 and T7 RNA polymerases; and reverse transcriptases such as AMV, M MuLV, MMLV, RNAse H' MMLV (Superscript®), Superscript® II, ThermoScript®, HIV 1, and RAV2 reverse transcriptases. All of these enzymes are commercially available. Exemplary polymerases with multiple specificities include RAV2 and Tli (exo) polymerases. Exemplary thermostable polymerases include Tub, Taq, Tth, Pfx, Pfu, Tsp, Tfl, Tli and *Pyrococcus* sp. GB D DNA polymerases.

Suitable reaction conditions are chosen to permit amplification of the target nucleic acid, including pH, buffer, ionic strength, presence and concentration of one or more salts, presence and concentration of reactants and cofactors such as nucleotides and magnesium and/or other metal ions (e.g., manganese), optional cosolvents, temperature, and thermal cycling profile for amplification schemes comprising a polymerase chain reaction, and may depend in part on the polymerase being used as well as the nature of the sample. Cosolvents include formamide (typically at from about 2 to about 10%), glycerol (typically at from about 5 to about 10%), and DMSO (typically at from about 0.9 to about 10%). Techniques may be used in the amplification scheme in order to minimize the production of false positives or artifacts produced during amplification. These include "touchdown" PCR, hot start techniques, use of nested primers, or designing PCR primers so that they form stem-loop structures in the event of primer-dimer formation and thus are not amplified. Techniques to accelerate PCR can be used, for example, centrifugal PCR, which allows for greater convection within the sample, and comprising infrared heating steps for rapid heating and cooling of the sample. One or more cycles of amplification can be performed. An excess of one primer can be used to produce an excess of one primer extension product during PCR; preferably, the primer extension product produced in excess is the amplification product to be detected. A plurality of different primers may be used to amplify different target nucleic acids or different regions of a particular target nucleic acid within the sample.

Amplified target nucleic acids may be subjected to post amplification treatments. For example, in some cases, it may be desirable to fragment the target nucleic acid prior to hybridization in order to provide segments which are more readily accessible. Fragmentation of the nucleic acids can be carried out by any method producing fragments of a size useful in the assay being performed; suitable physical, chemical and enzymatic methods are known in the art.

An amplification reaction can be performed under conditions which allow a nucleic acid associated with the optical sensing site to hybridize to the amplification product during at least part of an amplification cycle. When the assay is performed in this manner, real time detection of this hybridization event can take place by monitoring for light emission during amplification.

Real time PCR product analysis (and related real time reverse-transcription PCR) provides a well-known technique for real time PCR monitoring that has been used in a variety of contexts, which can be adapted for use with the methods described herein (see, Laurendeau et al. (1999) "TaqMan PCR-based gene dosage assay for predictive testing in individuals from a cancer family with INK4 locus haploinsufficiency" Clin Chem 45(7):982-6; Bièche et al. (1999) "Quantitation of MYC gene expression in sporadic breast tumors with a real-time reverse transcription-PCR assay" *Cancer Res* 59(12):2759-65; and Kreuzer et al. (1999) "LightCycler technology for the quantitation of bcr/abl fusion transcripts" *Cancer Res* 59(13):3171-4, all of which are incorporated by reference). In addition, linear PCR and Linear-After-The Exponential (LATE)-PCR can be adapted for use with the methods described herein.

Immunoassays can be conducted on the detection system of the invention, for example, at one or more optical sensing site of the system. Suitable immunoassay systems include but are not limited to competitive and noncompetitive assay systems. Such assay systems are typically used with techniques such as western blots, radioimmunoassays, EIA (enzyme immunoassay), ELISA (enzyme-linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, and cellular immunostaining (fixed or native) assays to name but a few. Such assays are routine and well known in the art (see, e.g., Ausubel et al., supra). Immunoassay techniques particularly useful with the detection systems described herein include but are not limited to ELISA, "sandwich" immunoassays, and fluorescent immunoassays. Exemplary immunoassays are described briefly below (but are not intended by way of limitation).

ELISAs generally involve preparing antigen, coating a well (e.g., an optical sensing site of the detection system) with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest to the coated well. One of skill in the art would be knowledgeable as to the parameters that can be modified to increase the signal detected as well as other variations of ELISAs known in the art.

In one exemplary immunoassay, a sample contains an unknown amount of biologically active analyte to be measured, which may be, for example, a protein. The analyte may also be termed an antigen. The sample may be spiked with a known or fixed amount of labeled analyte. The spiked sample is then incubated with an antibody that binds to the analyte, so that the analyte in the sample and the labeled analyte added to the sample compete for binding to the available antibody binding sites. More or less of the labeled analyte will be able to bind to the antibody binding sites, depending on the relative concentration of the unlabeled analyte present in the sample. Accordingly, when the amount of labeled analyte bound to the antibody is measured, it is inversely proportional to the amount of unlabeled analyte in the sample. The amount of analyte in the original sample may then be calculated based on the amount of labeled analyte measured, using standard techniques in the art.

In one exemplary competitive immunoassay, an antibody that binds to a biologically active analyte may be coupled with or conjugated with a ligand, wherein the ligand binds to an additional antibody added to the sample being tested. One example of such a ligand includes fluorescein. The additional antibody may be bound to a solid support (e.g., an optical sensing site of the detection system). The additional antibody binds to the ligand coupled with the antibody that binds in turn to the analyte or alternatively to the labeled analyte, forming a mass complex which allows isolation and measurement of the signal generated by the label coupled with the labeled analyte.

In another type of exemplary competitive immunoassay, the biologically active analyte to be measured may be bound to a solid support (e.g., an optical sensing site of the detection system), and incubated with both an antibody that binds to the analyte and a sample containing the analyte to be measured. The antibody binds to either the analyte bound to the solid support or to the analyte in the sample, in relative proportions depending on the concentration of the analyte in the sample. The antibody that binds to the analyte bound to the solid support is then bound to another antibody, such as anti-mouse IgG, that is coupled to a label. The amount of signal generated from the label is then detected to measure the amount of antibody that bound to the analyte bound to the solid support. Such a measurement will be inversely proportional to the amount of analyte present in the sample. Such an assay may be used in the detection system of the present invention.

A wide diversity of labels are available in the art that can be employed for conducting the subject assays. In some embodiments labels are detectable by spectroscopic, photochemical, biochemical, immunochemical, or chemical means. For example, useful nucleic acid labels include fluorescent dyes, enzymes, biotin, dioxigenin, or haptens and proteins for which antisera or monoclonal antibodies are available. A wide variety of labels suitable for labeling biological components are known and are reported extensively in both the scientific and patent literature, and are generally applicable to the present invention for the labeling of biological components. Suitable labels include enzymes, substrates, cofactors, inhibitors, fluorescent moieties, chemiluminescent moieties, or bioluminescent labels. Labeling agents optionally include, for example, monoclonal antibodies, polyclonal antibodies, proteins, or other polymers such as affinity matrices, carbohydrates or lipids. Detection proceeds by any of the methods described herein, for example, by detecting an optical signal in an optical waveguide. A detectable moiety can be of any material having a detectable physical or chemical property. Such detectable labels have been well-developed in the field of gel electrophoresis, column chromatography, solid substrates, spectroscopic techniques, and the like, and in general, labels useful in such methods can be applied to the present invention. Preferred labels include labels that produce an optical signal. Thus, a label includes without limitation any composition detectable by spectroscopic, photochemical, biochemical, immunochemical, electrical, optical, thermal, or chemical means.

In some embodiments the label is coupled directly or indirectly to a molecule to be detected such as a product, substrate, or enzyme, according to methods well known in the art. As indicated above, a wide variety of labels are used, with the choice of label depending on the sensitivity required, ease of conjugation of the compound, stability requirements, available instrumentation, and disposal provisions. Non radioactive labels are often attached by indirect means. Generally, a ligand molecule is covalently bound to a polymer. The ligand then binds to an anti ligand molecule which is either inherently detectable or covalently bound to a signal system, such as a detectable enzyme, a fluorescent compound, or a chemiluminescent compound. A number of ligands and anti-ligands can be used. Where a ligand has a natural anti-ligand, for example, biotin, thyroxine, and cortisol, it can be used in conjunction with labeled anti-ligands. Alternatively, any haptenic or antigenic compound can be used in combination with an antibody.

In some embodiments the label can also be conjugated directly to signal generating compounds, for example, by conjugation with an enzyme or fluorophore. Enzymes of interest as labels will primarily be hydrolases, particularly phosphatases, esterases and glycosidases, or oxidoreductases, particularly peroxidases. Fluorescent compounds include fluorescein and its derivatives, rhodamine and its derivatives, dansyl, and umbelliferone. Chemiluminescent compounds include luciferin, and 2,3-dihydrophthalazinediones, such as luminol.

Methods of detecting labels are well known to those of skill in the art. Thus, for example, where the label is a fluorescent label, it may be detected by exciting the fluorochrome with the appropriate wavelength of light and detecting the resulting fluorescence by, for example, a detection system as described herein. Similarly, enzymatic labels are detected by providing appropriate substrates for the enzyme and detecting the resulting reaction product (e.g., a reaction product capable of producing a detectable optical signal).

In some embodiments the detectable signal may be provided by luminescent sources. "Luminescence" is the term commonly used to refer to the emission of light from a substance for any reason other than a rise in its temperature. In general, atoms or molecules emit photons of electromagnetic energy (e.g., light) when they move from an "excited state" to a lower energy state (usually the ground state); this process is often referred to as "radioactive decay". There are many causes of excitation. If the exciting cause is a photon, the luminescence process is referred to as "photoluminescence". If the exciting cause is an electron, the luminescence process is referred to as "electroluminescence". More specifically, electroluminescence results from the direct injection and removal of electrons to form an electron-hole pair, and subsequent recombination of the electron-hole pair to emit a photon. Luminescence which results from a chemical reaction is usually referred to as "chemiluminescence". Luminescence produced by a living organism is usually referred to as "bioluminescence". If photoluminescence is the result of a spin allowed transition (e.g., a single-singlet transition, triplet-triplet transition), the photoluminescence process is usually referred to as "fluorescence". Typically, fluorescence emissions do not persist after the exciting cause is removed as a result of short-lived excited states which may rapidly relax through such spin allowed transitions. If photoluminescence is the result of a spin forbidden transition (e.g., a triplet-singlet transition), the photoluminescence process is usually referred to as "phosphorescence". Typically, phosphorescence emissions persist long after the exciting cause is removed as a result of long-lived excited states which may relax only through such spin-forbidden transitions. A "luminescent label" may have any one of the above-described properties.

Suitable chemiluminescent sources include a compound which becomes electronically excited by a chemical reaction and may then emit light which serves as the detectible signal or donates energy to a fluorescent acceptor. A diverse number of families of compounds have been found to provide chemiluminescence under a variety of conditions. One family of compounds is 2,3-dihydro-1,4-phthalazinedione. A frequently used compound is luminol, which is a 5-amino compound. Other members of the family include the 5-amino-6,7,8-trimethoxy- and the dimethylamino[ca] benz analog. These compounds can be made to luminesce with alkaline hydrogen peroxide or calcium hypochlorite and base. Another family of compounds is the 2,4,5-triphenylimidazoles, with lophine as the common name for the parent product. Chemiluminescent analogs include para-dimethylamino and -methoxy substituents. Chemiluminescence may also be obtained with oxalates, usually oxalyl active esters, for example, p-nitrophenyl and a peroxide such as hydrogen peroxide, under basic conditions. Other useful chemiluminescent compounds that are also known include —N-alkyl acridinum esters and dioxetanes. Alternatively, luciferins may be used in conjunction with luciferase or lucigenins to provide bioluminescence.

In a separate embodiment, the present invention provides a method of monitoring one or more pharmacological parameter, for example, pharmacodynamic (PD) and/or pharmacokinetic (PK) parameters, useful for assessing efficacy and/or toxicity of a therapeutic agent. The method comprises subjecting a sample of bodily fluid from a subject administered with the therapeutic agent to a detection device for monitoring the one or more pharmacological parameter; using the detection device as described herein to yield detectable signals indicative of the values of the more than one pharmacological parameter from the sample; and detecting the detectable signal generated from said sample of bodily fluid.

In one implementation the samples tested can include a large number of a variety of small molecules (e.g., screening libraries) which are of interest when investigating new drugs. Accordingly, the detection system described herein is useful for screening libraries of small molecules to investigate their ability to interact with certain biologically active analytes to reveal potential new drugs. Further screening of some or all small molecule candidates may reveal adverse drug effects and toxicity.

In one implementation the samples can include molecules which are tested for toxicity.

In general in another aspect methods of using the detection systems described herein are provided.

In one embodiment, the scanning light source moves through its scanning path to a point at which it is coupled to and in optical communication with one or more in-coupling or excitation waveguides, thus generating a pulse of light within the waveguides. The light travels along the waveguides, reaches the optical sensing sites and interacts through the sensor, for example, an optical transducer. The samples are positioned at or near the waveguides. Next, the secondary light leaving the sensor couples into the out-coupling or collection waveguides and travels down the waveguide to its end at an edge of the substrate, for example, a chip facet. Light exiting the out-coupling or collection waveguides is then detected by the different elements of the detector, which can be a detector array. In some embodiments, the substrate comprises a plurality of waveguides that serve as both in/out-coupling waveguides, with the light source and the detector being coupled to and in optical communication with opposite ends of the waveguides. In other embodiments, the in/out-coupling waveguides collect light from the light source and guide the secondary light to the detector through one or more adapter.

In another embodiment, the scanning light source/detector moves through its scanning path to a point at which the light source is coupled to and in optical communication with one or more in-coupling waveguides, thus generating a pulse of light within the waveguides. At the same time, the detector is coupled to and in optical communication with one or more out-coupling waveguides. The light travels along the waveguides, reaches the optical sensing sites and interacts through the sensor, for example, an optical transducer. The samples are positioned at or near the waveguides. Next, the secondary light leaving the sensor couples into the out-coupling waveguides and travels down the waveguide to its end at an edge of the substrate, for example, a chip facet. Light exiting the out-coupling waveguides is then detected by the different elements of the detector, which can be a detector array. In some embodiments, the substrate comprises a plurality of waveguides that serve as both in/out-coupling waveguides, while the light source/detector chip comprises in-coupling and out-coupling waveguides that are coupled through at least one combiner. The light waves generated by the light source elements are coupled into the in-coupling waveguides of the light source/detector chip, then combined by combiners into the out-coupling waveguides, which couple this primary light to the waveguides of the substrate. The secondary light wave leaving the sensor travels through the same waveguides of the substrate to out-coupling waveguides of the light source/detector chip which guide the light wave to the detector elements.

In another embodiment, detection of a sample includes delivering a sample suspected of containing a target to be detected to an optical sensing site of the detection system. Delivering a sample to the system can include pipetting of a fluid to the optical sensing site. Other delivery means can include but are not limited to a robotic fluid delivery system or physically depositing a non-fluid or semi-fluid sample at the optical sensing site, either by hand or with the aid of a tool or robot manipulation system. Next, a first light wave produced by the scanning light source is provided to one or more of the plurality of waveguides in optical communication with the optical sensing site. The first light wave is transduced (e.g., measurably changed) by the sensor associated with the optical sensing site to form a second light wave carried back in one or more of the plurality of out-coupling or collection waveguides which are in optical communication with the optical sensing site. Next a measurable change in the second light wave is detected using the detector which is in optical communication with the out-coupling or collection waveguides. Detection of a measurable change in the second light wave indicates that the sensor has interacted with the target. It is envisioned that in various embodiments the waveguides described herein can be arranged substantially parallel as illustrated generally in the accompanying figures.

In a further embodiment, the detection method includes generating one or more light wave by the scanning light source which couples into the substrate at some point along its scanning path to produce the first light wave in one or more of the waveguides in a controlled manner.

In another embodiment, the different light source elements of the scanning light source can be switched on simultaneously to generate one or more input light waves.

The plurality of light waves can be coupled into the substrate to controllably produce the first light wave in one or more of the waveguides.

In one embodiment, all in-coupling waveguides are provided with a first light wave and simultaneous detection of second light waves at each out-coupling waveguide is achieved using a detector that is a photodetector array.

By controlled switching of the different light source elements, each waveguide can be individually addressed with a first light wave. The order of addressing the waveguides can be sequential, staggered, random or in any order desired. Rapid scanning of the entire array of optical sensing sites can be achieved with the aid of the photodetector array since any second light wave associated with each out-coupling waveguide can be simultaneously detected.

In another embodiment, a single excitation waveguide is provided with a first light wave and simultaneous detection of second light waves at each collection waveguide is achieved using a detector that is a photodetector array. For example, where the two-dimensional waveguide array is configured as an array of 128 excitation waveguides and 128 collection waveguides, then it would be possible to simultaneously detect second light waves (if any) generated from 128 optical sensor sites after providing a single first light-wave in a first excitation waveguide. Thus, 128 optical sensing sites can be interrogated for presence or absence of target simultaneously. Next, a second excitation waveguide can be provided thereby triggering the interrogation of a second set of 128 optical sensing sites. The process can rapidly be repeated until every excitation waveguide has been excited and the entire array of optical sensing sites have been interrogated.

In various embodiments the method of using the detection system involves the detection of a substance, including but not limited to a biologically active analyte including a nucleic acid, a protein, an antigen, an antibody, a panel of proteins, a microorganism, a gas, a chemical agent and a pollutant. In a particular embodiment, a single nucleotide polymorphism (SNP) is detected in the target. In one embodiment expression of a gene is detected upon detection of the target.

Systems using planar waveguides for optical detection of SNPs have been described before. For example, single base extension ("SBEX") with planar waveguide fluorescent biosensor technology to detect SNPs has been described by Herron and Tolley in U.S. patent application Ser. No. 10/984,629, filed Nov. 8, 2004 and titled "Single Base Extension." Briefly, total internal reflectance fluorometry (TIRF) can be used in combination with SBEX under real time detection conditions for SNP detection using planar waveguide technology. Evanescent waves generated in a waveguide substrate will only excite fluorescently labeled analyte DNA molecules that are bound to stationary capture oligonucleotides. Herron found that the depth of evanescent wave useful for measurements is within about 300 nm of the sensor surface. The SBEX approach uses a DNA polymerase to incorporate, for example, Cy5 labeled dideoxynucleotriphosphates (ddNTPs). Additional labels are discussed elsewhere herein.

Identification ("calling") of the single base added to the 3' end of the probe molecule can be done in one of three ways: parallel channels for each of the four bases using a different labeled ddNTP in each channel; sequential SBEX reactions using a different labeled ddNTP in each reaction; or wavelength discrimination of the four possibilities using a different fluorescent label for each ddNTP. The first of these methods may be preferred. SBEX may be used in oligonucleotide genotyping and SNP detection systems, and is advantageous over traditional hybridization assays, for example, due to greater base specificity, production of a covalent bond between the labeled ddNTP and the probe, and simultaneous detection of multiple bases.

By using SBEX on waveguides, simultaneous detection of several different polymorphisms can be done with ease. By patterning the waveguide with different capture sequences, different points in a sequence, for example, a genome, a chromosome and/or a gene, may be assayed. As SBEX only requires a fluorescent label on the ddNTP monomers used, all instances of a particular base will be detected. In order to do the same thing with a traditional DNA hybridization assay, each probe DNA for each capture sequence would have to be fluorescently labeled.

The enzyme-catalyzed reaction has two distinct advantages. First, a stable covalent bond forms between the stationary phase and a labeled monomer, e.g., a Cy5-labeled monomer. This increases the assay sensitivity versus traditional hybridization assays where the fluorescent label is captured by the stationary phase via non-covalent interactions (duplex formation). Optionally a stringent washing step can be employed. Second, the polymerase enzyme incorporates the dideoxynucleotide with high fidelity—due to the replication accuracy of a polymerase, in general only the base that is complementary to the target base will react. SBEX is particularly well suited for planar waveguide technology, benefiting from the increased speed of a washless assay and increased sensitivity provided by kinetic data.

Using SBEX on the waveguide platform enables rapid assays (<5 min) to be performed that are able to differentiate between single nucleotide polymorphic and wild type sequences at temperatures less than 50° C.

Fluorescence imaging is sensitive to speed, sensitivity, noise and resolution, and each may be optimized for use in the invention; for example, speed may be increased to decrease assay times. Base extension may be detected using a CCD camera, a streak camera, spectrofluorometers, fluorescence scanners, or other known fluorescence detection devices, which generally comprise four elements: an excitation source; a fluorophore; a filter to separate emission and excitation photons; and a detector to register emission photons and produce a recordable output, typically an electrical or photographic output.

Polymerase enzymes useful in the invention are known in the art and include, but are not limited to, thermostable polymerases, such as pfu, Taq, Bst, Tfl, Tgo and Tth polymerase, DNA Polymerase I, Klenow fragment, and/or T4 DNA Polymerase. The polymerase may be a DNA-dependent DNA polymerase, a DNA-dependent RNA polymerase, a RNA-dependent RNA polymerase, a RNA-dependent DNA polymerase or a mixture thereof, depending on the template, primer and NTP used. The polymerase may or may not have proofreading activity (3' exonuclease activity) and/or 5' exonuclease activity).

The capture molecule and/or the analyte molecule of the invention may be any nucleic acid, including, but not limited to, DNA and/or RNA and modifications thereto known in the art, and may incorporate 5'-O-(1-thio)nucleoside analog triphosphates, .alpha.-thiotriphosphate, 7-Deaza-.alpha.-thiotriphosphate, N6-Me-.alpha.-thiotriphosphate, 2'-O-Methyl-triphosphates, morpholino, PNA, aminoalkyl analogs, and/or phosphorothioate.

In one embodiment immunoassays can be used with the present method of using the detection system. The optical sensing site of the detection system of the invention can be adapted to support an immunoassay, for example, by including one or more immunoassay reagent at or within the optical sensing site. In this embodiment an interaction between the optical sensing site and a sample being tested for a biologically active analyte can include an immunoassay conducted at the optical sensing site. As such, the optical sensing site interacting with the biologically active analyte can include an outcome of an immunoassay. In this manner, presence or absence of the analyte can be determined. Additionally the amount of analyte can be quantified. In one embodiment the immunoassay supported is a fluorescent assay. It is envisioned that the immunoassay can be a competitive or non-competitive immunoassay. In one embodiment the immunoassay supported is an ELISA.

It is envisioned that a variety of instrumentation relating to biological or environmental sample preparation, handling and analysis can be used in conjunction with the system and methods described herein. Examples of such instrumentation include but are not limited to a cell sorter, a DNA amplification thermal cycler, or a chromatography machine (e.g., GC or HPLC). Such instrumentation is well known to those skilled in the art. It is envisioned that a robotic interface could be used between the detection system of the present invention and various instrumentation relating to biological or environmental sample preparation, handling and analysis.

The optical detection system may be used in a range of applications including biomedical and genetic research as well as clinical diagnostics. Arrays of polymers such as nucleic acids may be screened for specific binding to a target, such as a complementary nucleotide, for example, in screening studies for determination of binding affinity and in diagnostic assays. In one embodiment, sequencing of polynucleotides can be conducted, as disclosed in U.S. Pat. No. 5,547,839. The nucleic acid arrays may be used in many other applications including detection of genetic diseases such as cystic fibrosis or diagnosis of diseases such as HIV, as disclosed in U.S. Pat. No. 6,027,880 and U.S. Pat. No. 5,861,242. Genetic mutations may be detected by sequencing or by hydridization. In one embodiment, genetic markers may be sequenced and mapped using Type-IIs restriction endonucleases as disclosed in U.S. Pat. No. 5,710,000.

Other applications include chip based genotyping, species identification and phenotypic characterization, as described in U.S. Pat. No. 6,228,575. Still other applications including diagnosing a cancerous condition or diagnosing viral, bacterial, and other pathological or nonpathological infections, are described in U.S. Pat. No. 5,800,992. A further application includes chip based single nucleotide polymorphism (SNP) detection as described in U.S. Pat. No. 6,361,947.

Gene expression may be monitored by hybridization of large numbers of mRNAs in parallel using high density arrays of nucleic acids in cells, such as in microorganisms such as yeast, as described in Lockhart et al., Nature Biotechnology, 14:1675-1680 (1996). Bacterial transcript imaging by hybridization of total RNA to nucleic acid arrays may be conducted as described in Saizieu et al., Nature Biotechnology, 16:45-48 (1998). Accessing genetic information using high density DNA arrays is further described in Chee, Science 274:610-614 (1996).

In addition to the nucleic acid arrays discussed above, optical detection systems of the invention may be used in combination with protein and chemical microarrays, including arrays of proteins, antibodies, small molecule compounds, peptides, and carbohydrates, or cell or tissue arrays, as described for example in Xu, Q. and Lam, K. S., J. Biomed. Biotechnol. 5:257-266 (2003). Protein and chemical arrays may be used in combination with the methods and devices of the invention in a number of potential applications, including but not limited to proteomics (including assays of both protein-protein interactions and protein-ligand interactions), screening assays for drug discovery, and toxicology testing. In some applications these assays may utilize label-free optical sensing methods as described, for example, in U.S. Pat. No. 7,349,080 and U.S. Pat. No. 7,292,336.

A further potential application is detection of chemical and/or biological warfare agents, including but not limited to bacterial spores (for example, as described in U.S. Pat. No. 6,498,041); bacterial agents (e.g., *Bacillus anthracis, Yersinia pestis, F. tulararensis, Brucella, Clostridium botulinum, Clostridium tetani, Coxiella burnetii*, and *Vibrio cholerae*); viral agents (e.g., variola virus, viral encephalitis agents such as Venezuelan equine encephalitis, western equine encephalitis and eastern equine encephalitis; and viral hemorraghic fever agents such as arenaviridae, bunyaviridae, filoviridae, and flaviviridae) and toxins (e.g., *Staphylococcus* enterotoxin B, botulinum toxin, ricin, and mycotoxins, as well as anticrop agents (e.g., *Puccinia graministritiiti, Piricularia oryzae, Tilettia caries, Tilettia foetida, Fusarium fungus*, and herbicides). Bacterial and viral agents may be detected using, for example, nucleic acid based methods such as real-time PCR, antibody-based detection methods such as ELISA, or using antimicrobial peptides as described by Kulagina et al., Sens. Actuators B. Chem. 121:150-157 (2007).

Further potential applications are in food safety, including detection of food-borne pathogens (e.g., *Salmonella typhosa, Salmonella typhimurium, Campylobacter jejuni, Escherichia coli* 0157H:H7, *Listeria monocytogenes, Stapholococcus aureus*, and *Clostridium perfringens*); detection of chemical substances that function as indicators of deterioration, for example, those caused by the process of oxidation; and detection of traces of contaminating chemical compounds, toxins, additives, or pesticides.

Further non-limiting potential applications include detection and diagnosis of viral and bacterial infectious diseases (e.g. AIDS, Bird Flu, SARS, West Nile virus); point-of-care monitoring of patients (e.g, detection of sugar and insulin levels in diabetic patients, detection of blood gas levels or lactic acid levels); pregnancy testing; detection of drugs or narcotics (e.g., cocaine, ecstasy, methamphetamines, opiates); detection of chemical and explosive substances (e.g, RDX, TNT, nitroglycerin); and environmental monitoring of air, water or soil samples, including the detection of pesticides, heavy metals, nitrates or phosphates.

The working system described here can also be a subsystem within a much larger bio-analysis system. The bio-analysis system could include all the aspects of sample preparation prior to optical detection, the post processing of data collected in the optical detection phase and finally decision making based on these results. Sample preparation may include steps such as: extraction of the sample from the tested subject (human, animal, plant environment etc.); separation of different parts of the sample to achieve higher concentration and purity of the molecules under investigation; sample amplification (e.g. through PCR); attachment of fluorescence tags or markers to different parts of the sample; and spotting of the sample onto the substrate. The post processing of the collected data may include: normalization; background and noise reduction; and statistical analysis such as averaging over repeated tests or correlation between different tests. The decision making may include: testing against a predefined set of rules and comparison to information stored in external databases.

The applications and uses of the detection systems described herein can produce one or more result useful to diagnose a disease state of an individual, for example, a patient. In one embodiment, a method of diagnosing a disease comprises reviewing or analyzing data relating to the presence and/or the concentration level of a target in a sample. A conclusion based upon review or analysis of the data can be provided to a patient, a health care provider or a health care manager. In one embodiment the conclusion is based upon the review or analysis of data regarding a disease diagnosis. It is envisioned in another embodiment that providing a conclusion to a patient, a health care provider or a health care manager includes transmission of the data over a network.

Accordingly, business systems and methods using the detection systems and methods described herein are provided.

One aspect of the invention is a business method comprising screening patient test samples for the presence or absence of a biologically active analyte to produce data regarding the analyte, collecting the analyte data, and providing the analyte data to a patient, a health care provider or a health care manager for making a conclusion based upon review or analysis of the data regarding a disease diagnosis. In one embodiment providing a conclusion to a patient, a health care provider or a health care manager includes transmission of the data over a network.

Figure 15:
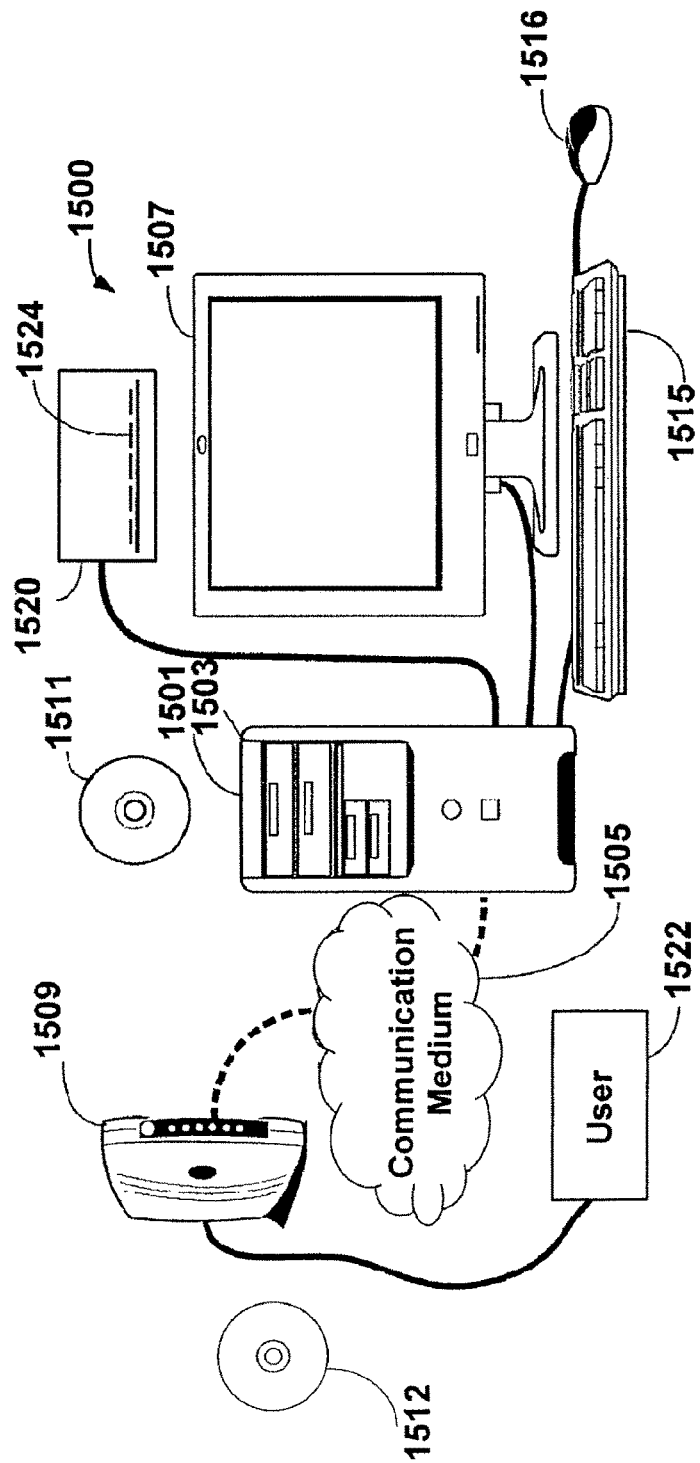
FIG. 15 is a block diagram showing a representative example logic device in communication with an apparatus for use with the detection system of the invention.

Accordingly FIG. 15 is a block diagram showing a representative example of a logic device through which reviewing or analyzing data relating to the present invention can be achieved. Such data can be in relation to a disease, disorder or condition in an individual. FIG. 15 shows a computer system (or digital device) 1500 connected to an apparatus 1520 for use with the detection system 1524 to, for example, produce a result. The computer system 1500 may be understood as a logical apparatus that can read instructions from media 1511 and/or network port 1505, which can optionally be connected to server 1509 having fixed media 1512. The system shown in FIG. 15 includes CPU 1501, disk drives 1503, optional input devices such as keyboard 1515 and/or mouse 1516 and optional monitor 1507. Data communication can be achieved through the indicated communication medium to a server 1509 at a local or a remote location. The communication medium can include any means of transmitting and/or receiving data. For example, the communication medium can be a network connection, a wireless connection or an internet connection. Such a connection can provide for communication over the World Wide Web. It is envisioned that data relating to the present invention can be transmitted over such networks or connections for reception and/or review by a party 1522. The receiving party 1522 can be but is not limited to a patient, a health care provider or a health care manager.

In one embodiment, a computer-readable medium includes a medium suitable for transmission of a result of an analysis of an environmental or biological sample. The medium can include a result regarding a disease condition or state of a subject, wherein such a result is derived using the methods described herein.

Kits comprising reagents useful for performing the methods described herein are also provided.

In some embodiments, a kit comprises detection system as described herein and reagents for detecting a target in the sample. The kit may optionally contain one or more of the following: one or more fluorescent or luminescent molecular tag, and one or more biologically active analyte including a nucleic acid, protein, microorganism or chemical agent.

The components of a kit can be retained by a housing. Instructions for using the kit to perform a described method can be provided with the housing, and can be provided in any fixed medium. The instructions may be located inside the housing or outside the housing, and may be printed on the interior or exterior of any surface forming the housing that renders the instructions legible. A kit may be in multiplex form for detection of one or more different target biologically active analyte including nucleic acid, protein, microorganism, gas, chemical agent or pollutant.

Figure 16:
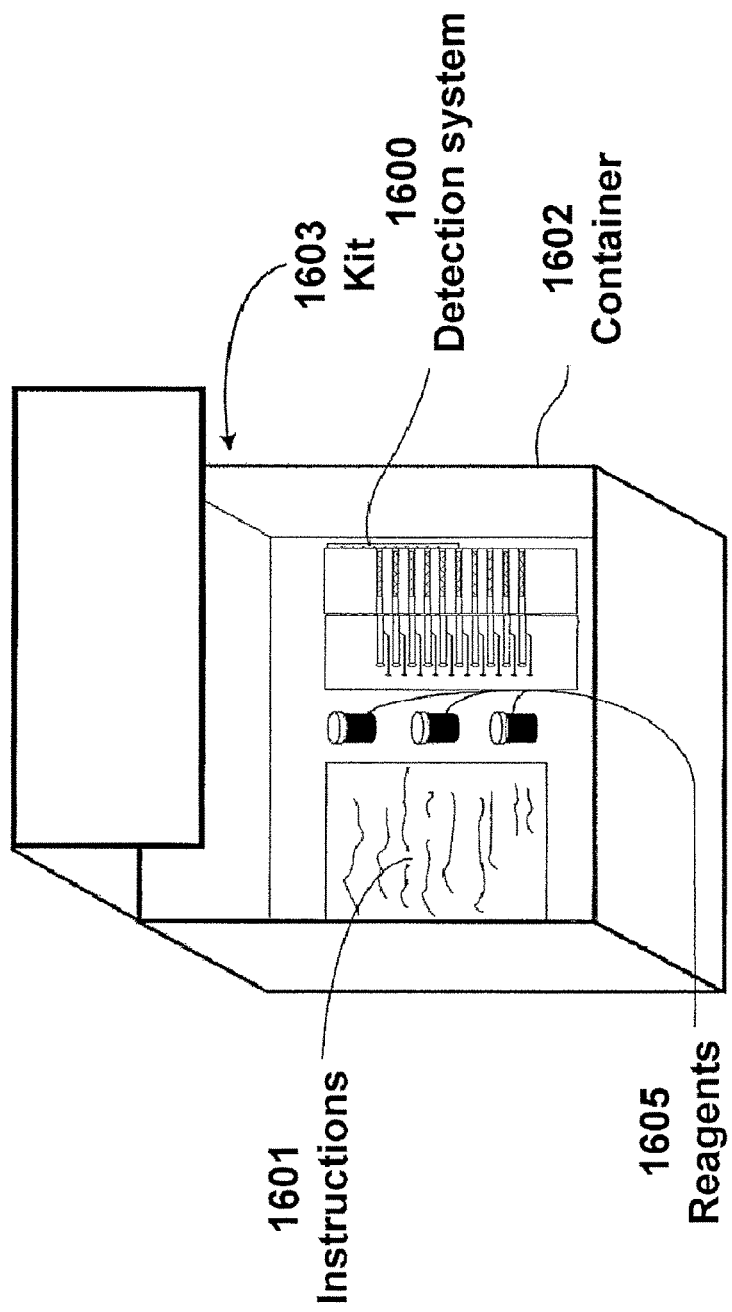
FIG. 16 is a block diagram showing a representative example of a kit.

As described herein and shown in an illustrative examples in FIG. 16, in certain embodiments a kit 1603 can include a detection system 1600, a housing or container 1602 for housing various components. As shown in FIG. 16, and described herein, the kit 1603 can optionally include instructions 1601 and reagents 1605, for example, DNA hybridization or immunoassay reagents. Other embodiments of the kit 1603 are envisioned wherein the components include various additional features described herein.

In one embodiment, a kit for assaying a sample for a target includes a detection system including a scanning light source, a detector, and a substrate. The substrate can include a plurality of excitation waveguides and a plurality of collection waveguides as described herein. The excitation waveguides and collection waveguides of the substrate cross or intersect to form intersection regions and a two-dimensional array. The system further includes a plurality of optical sensing sites. The optical sensing sites are in optical communication with one or more excitation waveguides and one or more collection waveguides. The kit further includes packaging and instructions for use of the system.

In another embodiment, the crossing of the excitation waveguides and collection waveguides is substantially perpendicular.

In another embodiment, a kit for assaying a sample for a target includes a detection system including a scanning light source, a detector, and a substrate. The substrate can include a plurality of substantially parallel in-coupling waveguides and a plurality of substantially parallel out-coupling waveguides as described herein. The system can further include a plurality of optical sensing sites. The optical sensing sites are in optical communication with one or more waveguides. The kit further includes packaging and instructions for use of the system.

In one embodiment, the kit includes a detection system that is a planar lightwave circuit (PLC).

In general, in another aspect methods of manufacturing a substrate for assaying a sample for a target are provided. In one embodiment the substrate is a PLC.

The starting material for manufacturing PLC devices is a wafer usually made of silicon (Si) or silica (SiO2). The most common wafer diameters in use are 4", 6" and 8". The manufacturing process for PLC devices involves two basic processes, namely, deposition and etching. A short description of each of them is given below.

In certain embodiments the methods of manufacturing the systems described herein can include, but are not limited to laser writing, UV writing and photonic band-gap waveguide methods. The manufacturing process in some embodiments includes one or more steps of deposition, masking and etching.

Deposition:

In the deposition step a layer of well defined material having well controlled thickness is deposited across the entire wafer. The most common materials used for waveguide layer deposition are silica (SiO2), also known as glass, and silicon nitride (Si3N4). The optical properties of the silica (mainly its refractive index) is controlled by the amount of doping (Ge, P, and B etc.) introduced during the deposition. Other materials such as silicon, glass, epoxy, lithium niobate, indium phosphide and SiON (silicon oxynitride) and its derivatives are also used. For the cladding layer, materials can include but are not limited to silicon, silica (SiO2), glass, epoxy, lithium niobate and indium phosphide.

The deposition step is done using several technologies such as PECVD (Plasma-Enhanced Chemical Vapor Deposition), LPCVD (Low Pressure CVD), APCVD (Atmospheric pressure CVD), FHD (Flame Hydrolysis Deposition) and others well known in the art.

Figure 17A:
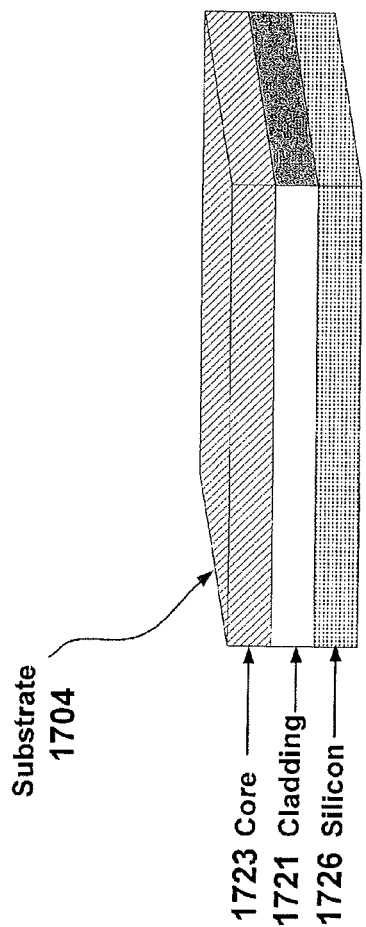
FIGS. 17A-D are schematics illustrating a representative manufacturing process for the substrate and waveguides of the invention.

FIG. 17A illustrates an exemplary substrate 1704 as a schematic structure created after two consecutive deposition steps of a cladding 1721 layer and a core 1723 layer over a silicon 1726 layer, which can be a wafer. As mentioned above, these two layers differ in the refraction index which is achieved by using different levels of doping. Typical thicknesses for the different layers are: Cladding up to about 20 µm and core up to 6 µm. The thickness of the silicon 1726 wafer can range from about 0.5 mm to 1 mm.

Figure 17B:
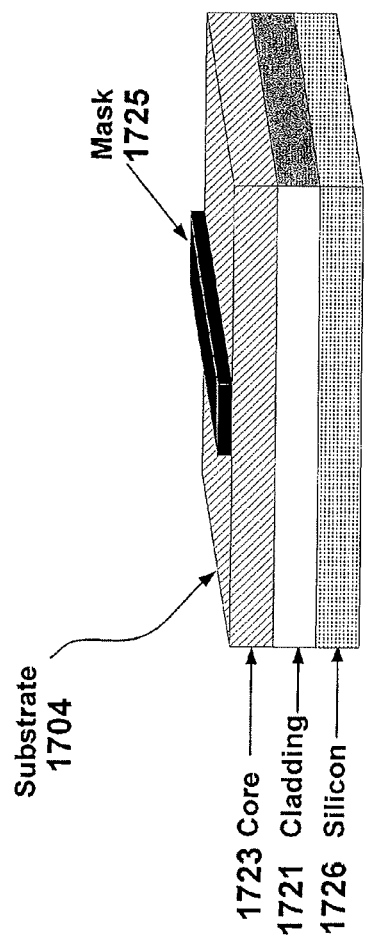

Masking:

Following the deposition and before the etching step, the desired two-dimensional structure of the PLC device is transferred to the deposited wafer by masking the areas not to be etched away. The masking is done in several steps involving covering the wafer with light sensitive material, exposing it to light through lithographic masks and removing the exposed material leaving in place the mask. The result of such steps is shown in FIG. 17B where a mask 1725 is shown on top of the core 1723 layer of the substrate 1704.

Figure 17C:
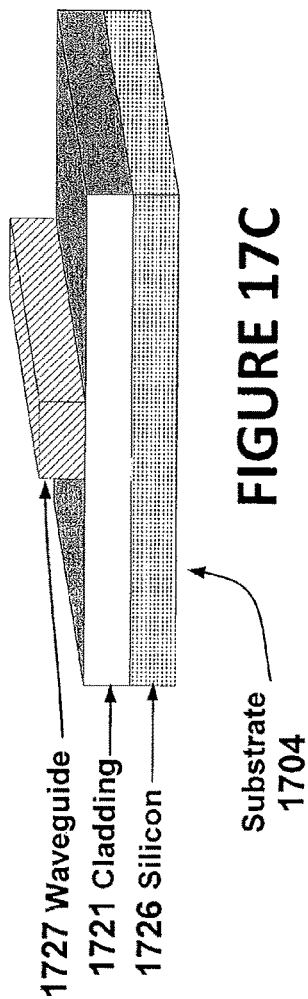

Etching:

In the etching step, material at the un-masked areas is removed from the top core 1723 layer of the substrate (see FIG. 17C). The etching rate is a known parameter, therefore the etching depth can be controlled by time. The two most common techniques for etching are wet-etching and Reactive-Ion-Etching (RIO). FIG. 17C shows the results of the etching step which results in a waveguide 1727.

Figure 17D:
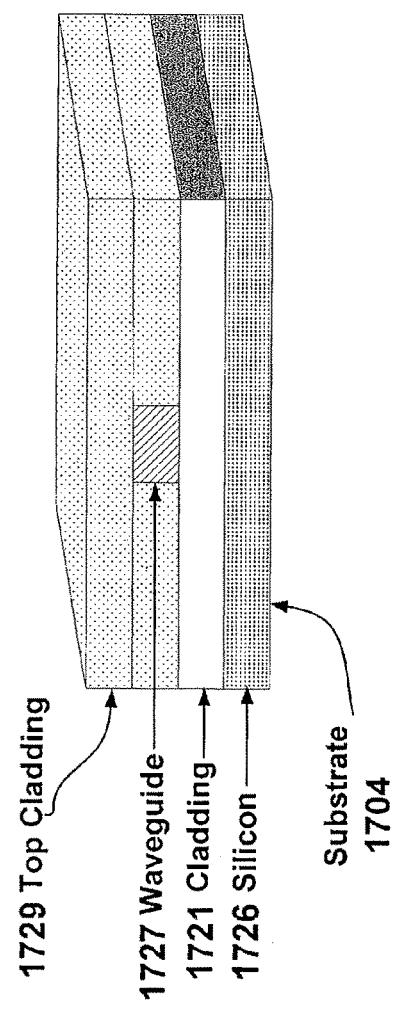

After the etching step, an over-cladding or top cladding 1729 layer is created using a deposition step similar to the one described above. The results are shown in FIG. 17D. As shown in FIG. 17D, the resulting waveguide 1727 can be surrounded by a top cladding 1729 and a cladding 1721 over a silicon 1726 layer.

The above steps can be repeated to create several waveguide layers one on top of the other. In this case, a planarization step may be required between one waveguide layer and the other. This is done using a technique known as Chemical Mechanical Planarization (CMP).

Figure 18:
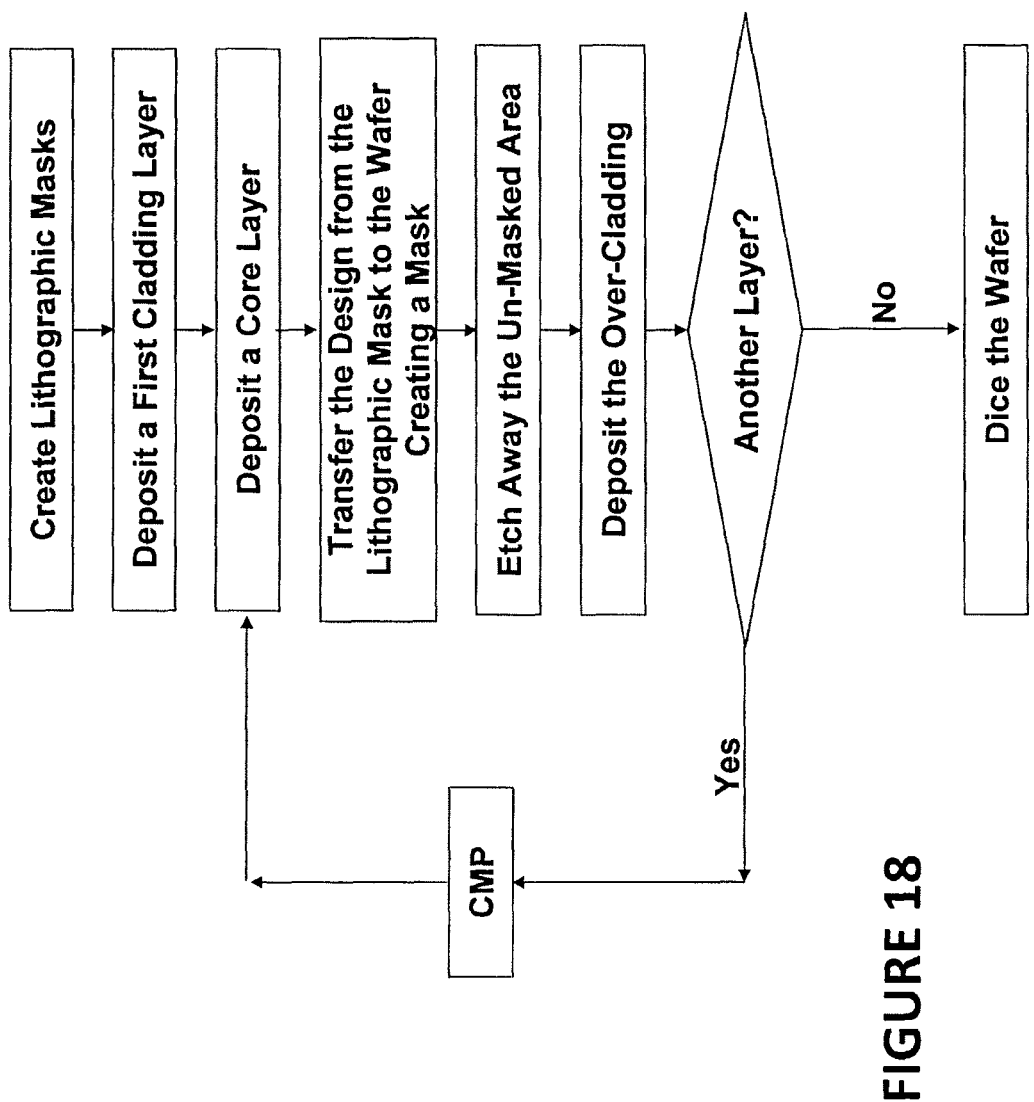
FIG. 18 is a flow chart showing a representative manufacturing process for the substrate.

When the wafer processing is completed, it can be diced into the individual chips. An exemplary simplified flowchart of the manufacturing process is shown in FIG. 18.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Signal Normalization

The present invention features methods and optical arrangements enabling the performance of two or more assays separated by time and/or separated by the color/wavelength of their emitted fluorescence on each and every sensing-well of a waveguide based bio-sensing chip. In some embodiments, at least one of the assays performed in each and every well is attempting to measure the signal generated by the presence of a target moiety. The other assays measure the signal generated by one or more secondary moieties in the sample, either naturally occurring or intentionally added, or by moieties immobilized to the sensing well, which signal indicates the level of a critical parameter such as temperature, excitation-light intensity, reagents aging, blood hematocrit and non-specific binding. These signals generated by the secondary moieties can serve to calibrate and/or normalize the signal measured from the target moiety in order to achieve a more consistent and reliable assay result which takes into account the variation of these signal affecting parameters.

The optical arrangement that can be used for the current invention may be based on the optical system as described above and further described in U.S. Pat. No. 7,951,583 and U.S. Pat. No. 8,187,866 and can include in addition:

Two or more excitation lasers, each having a different wavelength.

Combining and switching mechanisms for getting the light from each laser to every sensing well on the chip.

Interference filters allowing one or more of the fluorescent signals excited by one or more of the lasers to reach the optical detector at the output of the sensing chip while blocking all excitation light from the lasers.

Moieties labelled with different fluorescent tags which fluorescence can be excited using one or more of the excitation lasers and can be measured through one or more of the interference filters.

In general, one or more specific capture moieties (e.g. antibodies specific to a target molecules) are immobilized in each of the sensing wells of the waveguide-based sensing chip. When the sample is introduced to the surface of the chip, the specific target moieties in the sample start binding to the corresponding specific capture moieties in the sensing well. Shinning laser light having a wavelength within the excitation spectrum of one or more of the fluorescent tags, generates fluorescence with wavelengths within the emission spectrum of these fluorescent tags. This fluorescent light signal is captured in the sensing-well and directed to an optical detector through interference filters that 'filters out' most of the remaining laser light, thus allowing the measurement of only the desired fluorescent light.

In a preferred embodiment of this invention, a mix of two different capture molecules are immobilized in each of the sensing wells. The mix contains, at a given ratio (e.g. 90:10), a capture antibody specific to the target being detected and a second capture antibody which is specific to a control/normalizing moiety. While performing the test, a known concentration of the control/normalizing moiety is added to the sample, together with two detection antibodies, one specific to the target being detected and the other specific to the control/normalizing moiety. The two detection antibodies are each fluorescently labelled with a different fluorescent tag, each tag emitting at a different fluorescence wavelength. The binding to the surface of the sensing wells is monitored in given time-intervals (e.g. every 5 seconds) by shining laser-light from two different lasers, one after the other, into the excitation waveguides of the sensing chip. As a result, we get two different readings on the optical detector for every time interval. The first reading appears upon coupling laser #1 into the excitation waveguides and it is a measure of the fluorescence emitted by the labelled detection antibodies specific to the target being detected. The second reading appears upon coupling laser #2 into the excitation waveguides and it is a measure of the fluorescence emitted by the labelled detection antibodies specific to the control/normalizing moiety. At each point in time, the first reading is normalized to the second reading by dividing one by the other or by implementing any other suitable mathematical algorithm, leading to the elimination or reduction of aberrations caused by factors (such as temperature changes and reagents aging) which similarly affect the target and the control moiety. In some embodiments, the time interval using for the first laser-light may be different than the interval used for the second laser-light. For example, one of the fluorophores may be more susceptible to photo-bleaching than the other fluorophore, so longer time intervals can be used with the photo-sensitive fluorophore in order to reduce photo-bleaching.

In a second preferred embodiment of this invention, a mix of two different capture molecules are immobilized in the each of the sensing wells. The mix contains, at a given ratio (e.g. 90:10), a capture antibody specific to the target being detected and a second capture antibody which is specific to a control/normalizing moiety. The test is performed in two steps. In the first step, a fluorescently labelled detector antibody specific to the target is added to the sample at a known concentration and the mix is presented to the sensing chip. The binding to the surface of the sensing wells is monitored in given time-intervals (e.g. every 5 seconds) by shining laser-light from a single laser, into the excitation waveguides of the sensing chip. As a result, we get the time dependent fluorescent signal for the first step on the optical detector. In the second step, the control/normalizing moiety together with its specific fluorescently labelled detector antibody are added to buffer or other selected matrix (e.g. serum, plasma, oral fluid) at a known concentration and the mix is presented to the sensing chip. The binding to the surface of the sensing wells is monitored in given time-intervals (e.g. every 5 seconds) by shining laser-light from the same single laser, into the excitation waveguides of the sensing chip. As a result, we get the time dependent fluorescent signal for the second step on the optical detector. The results of the first step are normalized at the end of the second step by the results of the second step. The normalization can be done by dividing point-by-point or by dividing each point of the first step by the average or slope (over time) of the second step, or by dividing the signal slope (over time) of the first step by the slope (over time) of the second step or any other mathematical algorithm that helps in the elimination of aberrations caused by factors (such as temperature changes and reagents aging) which similarly affect the target and the control moiety.

In a third preferred embodiment of the invention, a single capture molecule is immobilized in the each of the sensing wells. The capture molecule is specific to the target being detected. The test is performed in two steps. In the first step, a fluorescently labelled detector antibody specific to the target is added to the sample at a known concentration and the mix is presented to the sensing chip. The binding to the surface of the sensing wells is monitored in given time-intervals (e.g. every 5 seconds) by shining laser-light from a single laser, into the excitation waveguides of the sensing chip. As a result, we get the time dependent fluorescent signal for the first step on the optical detector. In the second step, the target moiety together with its specific fluorescently labelled detector antibody are added to buffer or other selected matrix (e.g. serum, plasma, oral fluid) at a known concentration and the mix is presented to the sensing chip. The binding to the surface of the sensing wells is monitored in given time-intervals (e.g. every 5 seconds) by shining laser-light from the same single laser, into the excitation waveguides of the sensing chip. As a result, we get the time dependent fluorescent signal for the second step on the optical detector. The results of the first reading are normalized at the end of the second step by the results of the second reading. The normalization can be done by dividing point-by-point or by dividing each point of the first step by the slope (over time) of the second step, or any other mathematical algorithm that helps in the elimination of abenations caused by factors (such as temperature changes and reagents aging).

In yet another preferred embodiment of this invention, a mix of three different capture molecules are immobilized in the each of the sensing wells. The mix contains, at a given ratio (e.g. 80:10:10), the capture antibody specific to the target being detected and a two other capture antibodies which are each specific to one control/normalizing moiety. While performing the test, a known concentrations of the two control/normalizing moieties, preferably one at low concentration and the other at high concentration, are added to the sample, together with three detection antibodies, one specific to the target being detected and the two other specific to the two control/normalizing moieties. Using two or more normalization points allows the generation of a calibration line or curve that reflects more accurately the effect that is being normalized for across the range measured, particularly when the effect, such as temperature or aging reagents, affects low concentrations differently than high concentrations. In some embodiments, the low concentration and the high concentration can be chosen to span the entire range to be measured. In some embodiments, the low concentration can be within 10, 20, 30, 40, or 50% of the low end of the range to be measured, and the high concentration can be within 10, 20, 30, 40, or 50% of the high end of the range to be measured. The three detection antibodies are each fluorescently labelled with a different fluorescent tag, each tag emitting at a different fluorescence wavelength. The binding to the surface of the sensing wells is monitored in given time-intervals (e.g. every 5 seconds) by shining laser-light from three different lasers, one after the other, into the excitation waveguides of the sensing chip. As a result, we get three different readings on the optical detector for each time interval. The first reading appears upon coupling laser #1 into the excitation waveguides and it is a measure of the fluorescence emitted by the labelled detection antibodies specific to the target being detected. The second reading appears upon coupling laser #2 into the excitation waveguides and it is a measure of the fluorescence emitted by the first labelled detection antibody specific to the first control/normalizing moiety. The third reading appears upon coupling laser #3 into the excitation waveguides and it is a measure of the fluorescence emitted by the second labelled detection antibody specific to the second control/normalizing moiety. At each point in time, the signal from the two control/normalizing moieties are used for normalizing the first reading using a suitable mathematical algorithm. Alternatively, at the end of test, the signal from the two control/normalizing moieties are used to generate a 'calibration curve/line' which is used to calculate the unknown concentration of the target.

Software Based Auto-Alignment of Cartridge with Optical Head

In some embodiments, the substrate 804 of the sensing chip as shown in FIG. 8, for example, can be incorporated into a cartridge with a fluid port for introducing a sample, a flow path for directing the sample to the substrate 804, and a waste reservoir for collecting the sample after is passes over the substrate, as further described in U.S. Patent Publication No. 20160033412, which is herein incorporated by reference in its entirety. When the substrate 804/cartridge is inserted into the reader, it is aligned with the detector 806, which can be an optical laser head.

As shown in FIG. 7H, the substrate can be modified to include a loop back waveguide 713. A software and control system can be used to align the cartridge with the optical head.

When the cartridge is inserted, a sensor detects the insertion of the cartridge and triggers the light source to send a signal to the substrate and begin the alignment process. In some embodiments, the sensor can be a mechanical, electrical, or optical switch that is triggered when the cartridge is inserted into the reader.

The light travels through the loop back waveguide and a detector, such as a CMOS detector, at the other end of the loop back waveguide 713 receives the light.

If the cartridge is aligned properly or partially aligned, the detector receives the light transmitted through the loopback waveguide. The amount of light received determines the status of the alignment.

If the amount of light crosses a predetermined threshold for complete alignment, the alignment process stops and is complete and the system is ready for the actual testing of the sample.

When the system is not properly aligned, initially the system uses broad passes of the optical head to rapidly detect the location of the loopback channel. Using a closed loop feedback control system the auto-alignment software controls the X & Y axis motion of the optical head and repeats this process till the alignment is done. In case of partial light detection, a smart algorithm is developed to optimize the alignment through X Y movement of the optical head till complete alignment happens.

Time outs can be put in place to detect error conditions.

A home position can be provided to bring the head to a fixed location in case the process has to be restarted.

With this automated system, no human intervention is needed to align the cartridge within the reader, making it a robust system.

Figure 23:
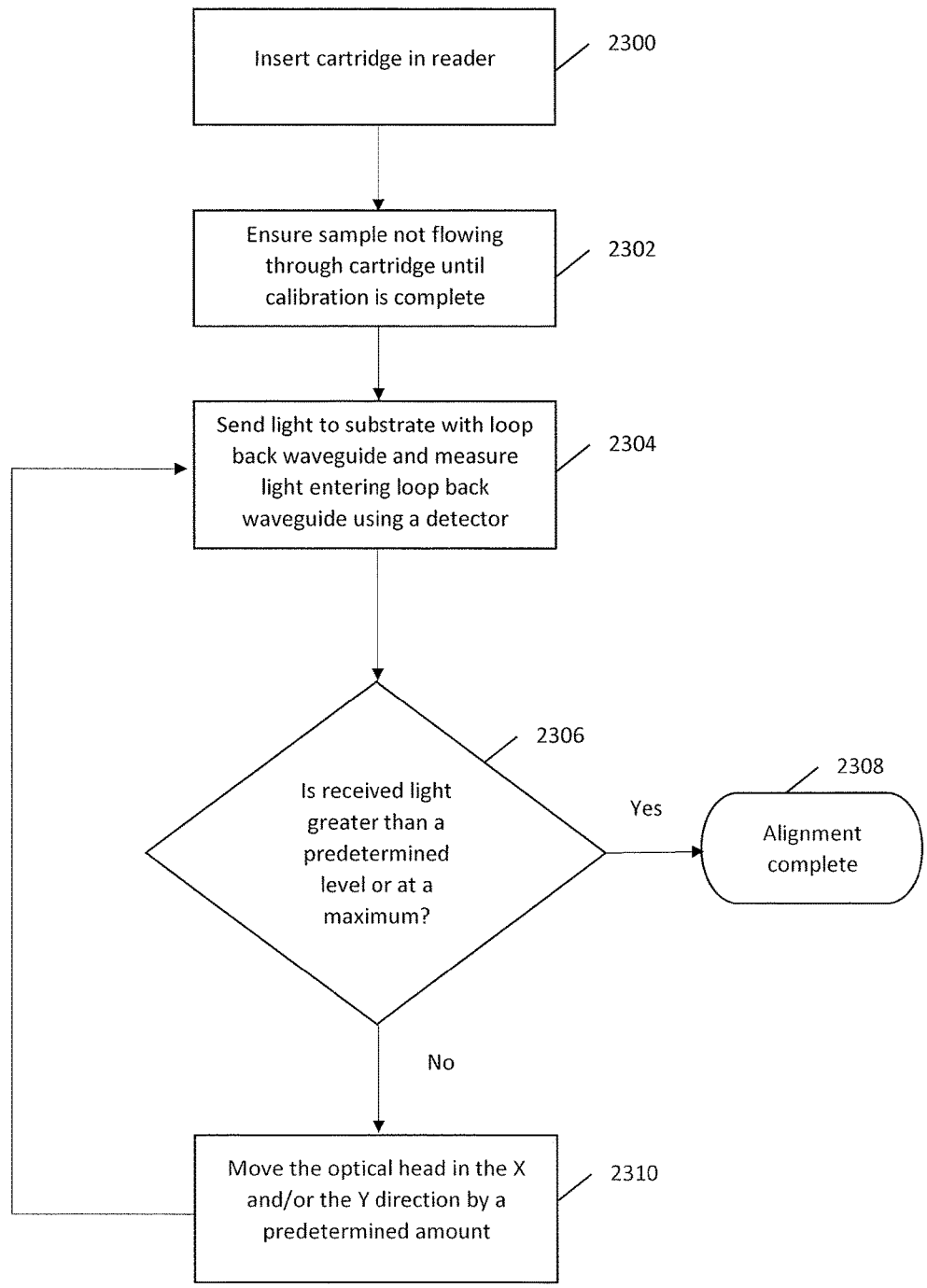
FIG. 23 is a flow chart illustrating a procedure for aligning a cartridge in a reader.

FIG. 23 illustrates a flowchart of an embodiment of the automated alignment procedure that can be implemented through a control system and/or software in the reader. In step 2300, a cartridge is inserted into a reader. As shown in step 2302, the reader system can ensure that the sample does not flow through the cartridge until after alignment is successfully completed. This can be accomplished, for example, by not applying a vacuum or activating a pump until alignment is successfully completed. After the cartridge is inserted into the reader, as shown in step 2304, light is sent to one end of the loop back waveguide of the substrate. A light detector at the other end of the loop back waveguide is used to measure the amount of light that is entering the loop back waveguide. As shown in step 2306, if the light measured by the loop back waveguide detector is greater than a predetermined level or at a maximum, the alignment is complete 2308. If the light measured by the detector is less than the predetermined level or less than a maximum detected level, then the optical head that is providing the light to the substrate is moved in the X and/or the Y direction by a predetermined amount, which may be on the order of microns, as shown in step 2310. The procedure then returns to step 2304, where light is again sent to the loop back waveguide and measured with the detector. In some embodiments, the optical head can be moved along a single axis, such as the X direction, until alignment is achieved along the X axis, and then the optical head can be moved along the second axis, such as the Y axis, until alignment is achieved along the Y axis. In some embodiments, the increase or decrease in light measured by the detector as the optical head is moved in a particular direction can be used to determine whether the optical head is being moved in the correct direction for achieving alignment. An increase in measured light indicates that the movement of the optical head is proceeding in the correct direction, while a decrease in measured light indicates that the movement of the optical head is proceeding in the wrong direction. In some embodiments, the optical head can be alternately moved in the X and Y directions during alignment.

Precision in Printing Antibodies on the Detection Chip

Very small volumes of antibodies in solution (~200 Pico liters) can be dispensed as droplets on the optical sensing sites of the substrate with high precision and high accuracy as described below. Dispensing of multiple layers of different samples, antibodies, ligands, oligonucleotides, or reagents on a plurality of locations on a substrate is a significant challenge as it requires greater level of precision and flexibility. Although the printing method is described with antibodies, other molecules, reagents, proteins, ligands, oligonucleotides, etc. can be also printed.

A use of specialized printer with hardware and software that supports a non-contact method of printing antibodies and a method to dry, detect and test the micro-structures formed by loading the antibody droplets on the specific spots, such as the sensing sites, on the bio-sensor chip, also called more generically as a substrate.

Special software is used to do on-line measurement of droplet volumes. A microscope with CCD camera is used to take images of the dispensed antibodies on the detection spots. A special image analysis software is used for spot detection, analysis of microstructures and post spotting Quality Control, making sure that the size and shapes and location of the spots are per specification and that the adjacent spots don't overlap with each other, which may create interference in the detection results.

Figure 24:
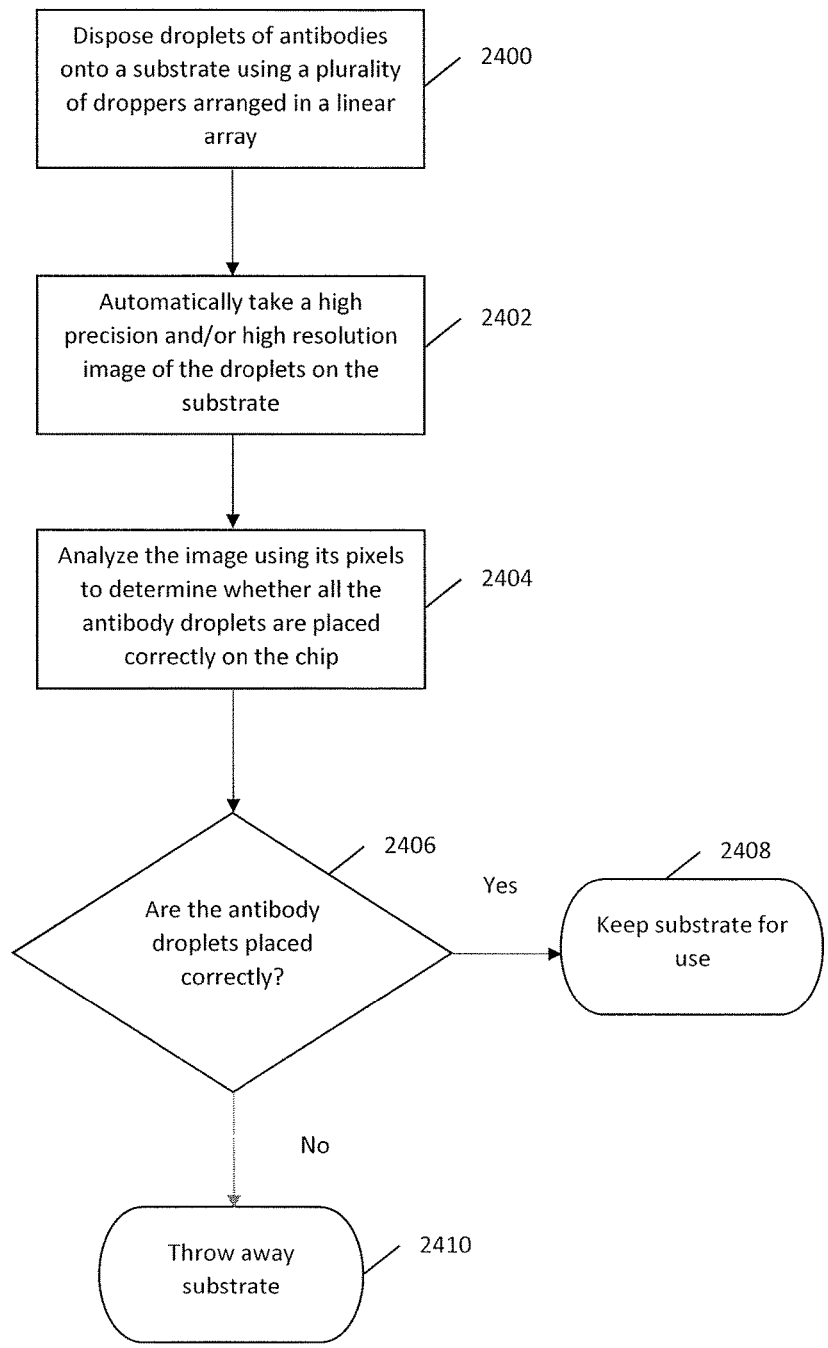
FIG. 24 is a flow chart illustrating a procedure for immobilizing antibodies to a substrate.
Figure 25A:
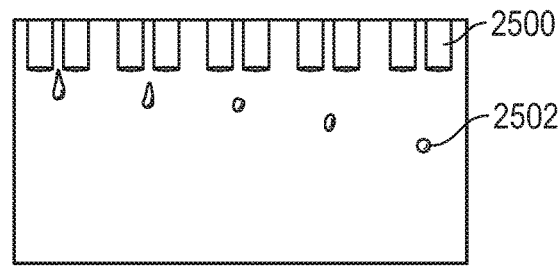
FIGS. 25A-25D illustrate an array of droppers that can dispense droplets of antibodies onto a substrate.
Figure 25B:
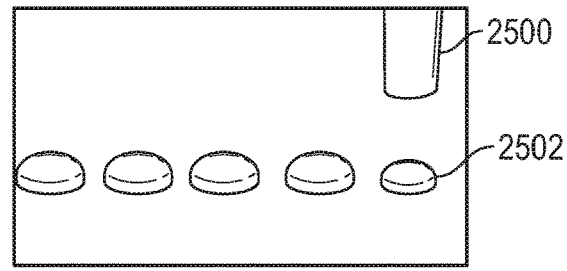
Figure 25C:
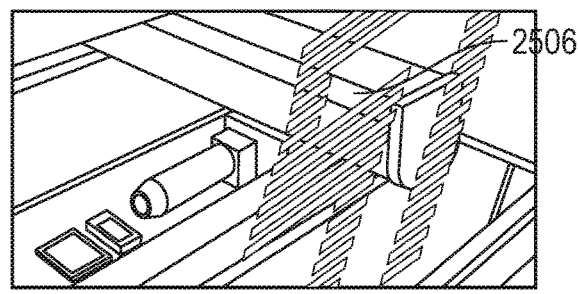
Figure 25D:
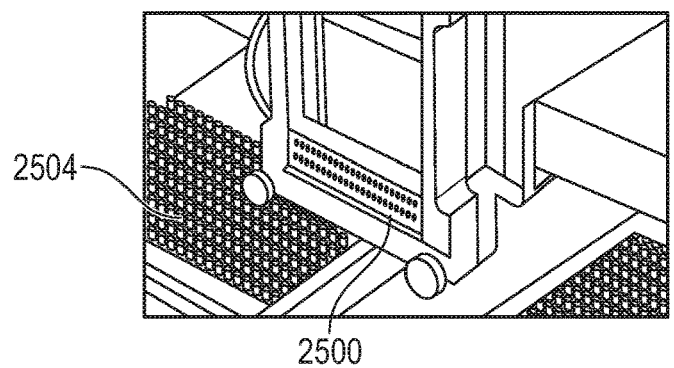

FIG. 24 illustrates a flowchart of the antibody printing procedure. In step 2400, droplets of antibodies are disposed onto a substrate using a plurality of droppers arranged in anay. In some embodiments, the array is linear. In other embodiments, the array can be two dimensional. As noted above, the droppers can dispose the droplets in a non-contact manner, meaning that the droplets are disposed above the surface of the substrate and then fall onto the substrate. The droppers never contact the substrate. In step 2402, a high resolution and high precision image of the droplets on the substrate can be automatically taken. In step 2404, image processing software can be used to analyze the image to determine the size, volume, shape, and location of the droplets which can be used in step 2406 to determine whether all the antibody droplets are placed correctly on the substrate. If the droplets are placed correctly, then the substrate can be kept for use and further processing in step 2408. If the droplets are not placed correctly, then the substrate can be thrown away in step 2410.

FIGS. 25A-25D illustrate a linear array of droppers 2500 that are dispensing droplets 2502 onto a substrate 2504. The linear array of droppers are part of a specialized printer 2506 and imager.

EXAMPLES

Example 1

Establishing the Limit of Detection

One feature of the sensors of the current invention is the ability to detect low numbers of biologically active analyte molecules. The following experiments demonstrate this capability. The limit of detection (LOD) of the sensors was determined by measuring fluorescently labeled ovalbumin in solution. The dye used was Alexa Fluor 660; it was excited at 658 nm and emission was measured at 690 nm. All measurements were made at room temperature (25° C.). LOD was assayed using two different methods: 1) determination of the lowest concentration of labeled ovalbumin detectable above buffer background with better than 95% confidence ($P<0.05$, Student's t-test); and 2) determination of the analytical sensitivity from a standard curve of sensor response vs. concentration (MDL=2*SD/slope, where SD is the standard deviation of the buffer background measurement and slope is the initial slope of the standard curve). These methods are comparable in that both determine the 95% confidence level for LOD. Values for LOD from three different step isotherms are shown in Table 1.

TABLE 1

| Isotherm | Chip Format | MDL Method 1 | MDL Method 2 |
| --- | --- | --- | --- |
| Experiment 1 | 100 × 100 μm sensors | 3.0 pM | 4.1 pM |
| Experiment 2 | 52.5 × 4,500 μm sensors | 0.1 pM | 0.33 pM |
| Experiment 3 | 52.5 × 4,500 μm sensors | 0.1 pM | 0.13 pM |

The number of molecules detected per sample was calculated as follows. The sample volume used in all experiments was 50 microliters. Thus, at a concentration of 0.1 pM for example, there were $3 \times 10^6$ molecules per sample. Since all molecules were evenly distributed across the entire volume, the number of molecules available per sensor was ~1000. The thickness of the fluid containing this number of molecules was ~1.7 mm. Using the diffusion parameters, it can be estimated that 0.1% to 1% of these molecules were able to bind to the surface of each sensor, or 1 to 10 molecules.

Example 2

Detection of Protein-Protein Interactions

The present invention is useful for measuring protein-protein interactions. In this example, the waveguide-based optical detection technology was used to measure the binding of ovalbumin to anti-ovalbumin antibodies. Before the experiment was conducted, chips with 52.5×4,500 μm sensing elements were dip-coated with anti-ovalbumin antibodies. This procedure involved several steps. First, the chips were cleaned. A chip fabricator coated the active surface of the chips with a thin polymer layer to protect it during wafer dicing. The polymer layer was removed by immersing chips in acetone for 5 minutes, followed by isopropanol for 5 minutes and a second isopropanol rinse for an additional minute. Chips were then washed in deionized water three times and dried in a vacuum desiccator. Next, the surface was activated. To immobilize capture molecules to the waveguides, a thin layer (~10 nm) of silicon dioxide was created on the chips by Piranha treatment. Chips were immersed in a Piranha solution containing 9% (v/v) $H_2O_2$ and 66.5% (v/v) $H_2SO_4$ for 45 minutes with agitation. This step removed organic contaminants and produced a thin (1-2 nanometer) layer of reactive silanol groups that were used for coupling antibodies. Chips were then rinsed four times in deionized water, followed by a final rinse in doubled distilled water.

Antibodies specific to ovalbumin were immobilized to the chips using an avidin/biotin chemistry that forms self-assembling monolayers. (Herron, J. N., H.-K. Wang, V. Janatová, J. D. Durtschi, K. D. Caldwell, D. A. Christensen, I.-N. Chang and S.-C. Huang (2003) Orientation and Activity of Immobilized Antibodies. In: *Biopolymers at Interfaces, 2nd Edition* (M. Malmsten, ed.), Surfactant Science Series, Vol. 110, Marcel Dekker, new York, pp. 115-163.) Avidin can adsorb to surfaces containing silanol groups due to electrostatic interactions. Antibody immobilization proceeded in two steps: adsorption of avidin to the Piranha treated chips (100 nM avidin in phosphate buffered saline, pH 7.4, adsorption time of 1 hr, followed by five PBS rinses) followed by binding of biotinylated anti-ovalbumin antibody (e.g. US Biological, polyclonal) to the adsorbed avidin (100 nM biotinylated anti-ovalbumin antibody in PBS). Chips were then rinsed three times in PBS, five more times in deionized water, then postcoated with a xeroprotectant (0.1 mg/mL trehalose in deionized water) and dried by nitrogen stream, followed by vacuum desiccation.

It was estimated that the capture antibody density at the end of the process was 1 pM per square centimeter.

To assay the interaction of ovalbumin with the anti-ovalbumin antibodies, fluorescently labeled ovalbumin in a solution containing phosphate buffered saline, pH 7.4, and 0.1 mg/mL bovine serum albumin, was added to a sample well on the surface of a chip as depicted in FIG. 7D. An ovalbumin concentration range of four orders of magnitude (from 0.1 pM to 1,000 pM) was used. The kinetics of the binding reaction were then monitored over a period of 10 minutes at room temperature, and fluorescence intensity was measured at 690 nm.

Figure 19:
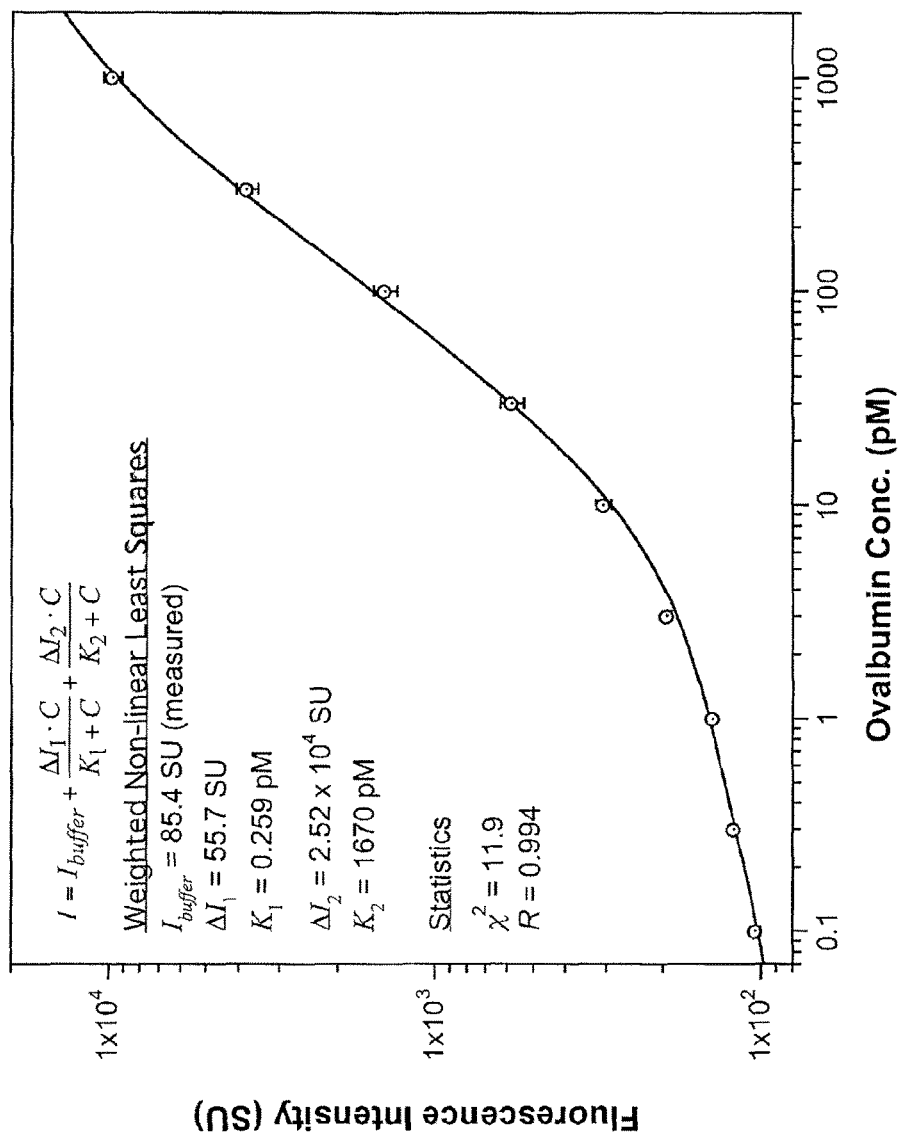
FIG. 19 is a plot of data for fluorescently labeled ovalbumin binding to immobilized antibodies specific for ovalbumin.

FIG. 19 shows the quantitative sensor response for the binding reaction. Fluorescence intensity at each ovalbumin concentration used is indicated with plot symbols and error bars and is plotted on a graph with log based abscissa and ordinate axes. The solid line in FIG. 19 is a curve fit. A two-constant model fit the binding data, representing binding behavior that is consistent with results from experiments using ultrasensitive (femtomolar) sensors in conjunction with 1-μm thick excitation waveguides (Plowman, T. E., W. M. Reichert, C. R. Peters, H. K. Wang, D. A. Christensen and J. N. Herron (1996), "Femtomolar Sensitivity using a Channel-etched Thin Film Waveguide Fluoroimmunosensor," *Biosensors & Bioelectronics* 11, 149-160). A small percentage of ovalbumin molecules (0.22%) simultaneously bound two different immobilized antibody molecules, while the overwhelming majority (>99%) of ovalbumin molecules bound to a single immobilized antibody. The small percentage of bivalent binding gives rise to the higher affinity binding constant ($K_1$), as well as the "foot" observed in the subpicomolar portion of the binding curve. Only a small percentage of high affinity binding was observed owing to the exquisite sensitivity and excellent precision of the sensor in the subpicomolar range. Precision was generally good across the 4-log concentration range of the assay.

Example 3

Detection of Polymerization of Nucleic Acids

The waveguide-based optical detection system can be used to quantify the polymerization of DNA in a primer extension assay. In a primer extension reaction, an mRNA target hybridizes to a DNA primer, and reverse transcriptase uses the mRNA target as a template to add deoxynucleotides (dATP, dTTP, dGTP, dCTP) to the 3' end of the DNA primer.

High sensitivity using a waveguide-based optical detection system requires that the hybridization in the primer extension reaction occur at concentrations in the low femtomolar range. Thus, it was first established that hybridization occurs at low concentrations on the surface of the chip. For this experiment, a capture oligonucleotide primer was immobilized to the chip, and a complementary synthetic DNA labeled at the 5' end with Cy5.5 was incubated with the primer. For experimental rigor, the sequences of both the captured oligonucleotide and a complementary synthetic DNA were verified by mass spectrometry.

Before the experiment was conducted, the capture oligonucleotide was immobilized on the surface of the chip by a dip-coating process. First, the chips were cleaned. A chip fabricator coated the active surface of the chips with a thin polymer layer to protect it during wafer dicing. The polymer layer was removed by immersing chips in acetone for 5 minutes, followed by isopropanol for 5 minutes and a second isopropanol rinse for an additional minute. Chips were then washed in deionized water three times and dried in a vacuum desiccator.

Next the surface was activated. To immobilize capture molecules to the waveguides, a thin layer (~10 nm) of silicon dioxide was deposited on the chips by either Piranha treatment or oxygen plasma treatment. Piranha treated chips were immersed in a Piranha solution containing 9% (v/v) H2O2 and 66.5% (v/v) H2SO4 for 45 minutes with agitation. This step produced a thin (1-2 nanometer) layer of reactive silanol groups. Chips were then rinsed four times in deionized water, followed by a final rinse in doubled distilled water. Oxygen plasma treated chips were exposed to oxygen plasma (100 W, 0.15 Torr) for 5 minutes using a plasma oven.

To attach oligonucleotides, activated chips (either Piranha or plasma treated) were derivatized with (3-Glycidyloxypropyl) trimethoxysilane (GPS) to form a reactive monolayer of epoxide groups on the surface of the chip. Chips were immersed in 0.1% (v/v) GPS in anhydrous toluene for 30 minutes at 40° C., followed by washing three times in 99.9% toluene. Chips were then dried in nitrogen and cured at 110° C. for 20 minutes. GPS-coated chips were immersed for 6 hours at 40° C. in a 5 micromolar solution of capture oligonucleotide dissolved in 0.1 M carbonate-bicarbonate buffer (pH 9) with 1 mM EDTA. The capture oligonucleotides were synthesized with a flexible spacer at the 5' end that terminated in a primary amino group, which reacts readily to the epoxy groups on the chip to form a stable covalent linkage. Chips were washed after the coupling reaction in 0.2% SDS, followed by three rinses in deionized water. Chips were then incubated in deionized water at 40° C. for 30 minutes and then dried in a nitrogen stream followed by vacuum desiccation overnight.

It was estimated that the density of capture oligonucleotides at the end of the process was 10 pM per square centimeter.

Hybridization reactions were performed for 10 minutes at room temperature over a synthetic DNA analyte concentration range of 10 femtomolar (10 fM) to 10 picomolar (10 pM). Analyte solutions were prepared in 3× sodium chloride-sodium citrate buffer (0.45 M NaCl, 45 mM sodium citrate, pH 7) with 0.01% sodium dodecyl sulfate and 1 mM EDTA. Limit of detection (LOD) was assessed using analysis of variance (ANOVA) with Dunnett's post-hoc test in which hybridization data from each concentration were compared to that of the negative control (buffer). Results are shown in Table 2 for two different experiments (Experiment 1 and Experiment 2):

TABLE 2

Dunnett's Multiple Comparison

| Comparison | Mean Difference | \|q\| (Dunnett's Statistic) | Probability |
| --- | --- | --- | --- |
| Experiment 1 | | | |
| Buffer vs 10 fM | −2.58 | 1.53 | 0.4881 |
| Buffer vs 30 fM | −6.66 | 3.94 | 0.0008 |
| Buffer vs 100 fM | −9.15 | 5.41 | <.0001 |
| Buffer vs 300 fM | −21.3 | 12.6 | <.0001 |
| Buffer vs 1 pM | −29.1 | 17.2 | <.0001 |
| Buffer vs 3 pM | −37.7 | 21.0 | <.0001 |
| Buffer vs 10 pM | −147 | 86.7 | <.0001 |
| Experiment 2 | | | |
| Buffer vs 10 fM | −19.5 | 2.30 | 0.1148 |
| Buffer vs 30 fM | −40.5 | 4.78 | <.0001 |
| Buffer vs 100 fM | −53.1 | 6.27 | <.0001 |
| Buffer vs 300 fM | −115 | 13.6 | <.0001 |
| Buffer vs 1 pM | −93.9 | 11.1 | <.0001 |
| Buffer vs 3 pM | −126 | 14.9 | <.0001 |
| Buffer vs 10 pM | −305 | 36.0 | <.0001 |

Mean Difference values were negative because the sensor response for each concentration was subtracted from that of the negative control (Buffer). Probability values are for the null hypothesis that the sensor response observed for a given concentration is not statistically different from that observed for the negative control. Using $P<0.05$ as the criterion for rejecting the null hypothesis, concentrations of 30 fM and above were statistically different from buffer in both experiments (i.e., MDL=30 fM). Comparison of the P values for the 10 fM concentrations in Experiments 1 & 2 (P=0.4881 for Experiment 1 and P=0.1148 for Experiment 2) show that sensitivity was better in the second experiment, approaching 10 fM.

Recycling chips by stripping off their layer of capture molecule with the aforementioned hydrogen peroxide/sulfuric acid cleaning solution and then immobilizing a new layer of capture molecules once resulted in diminished, but measurable hybridization levels with reduced sensitivity (in the low picomolar range; data not shown).

Figure 20:
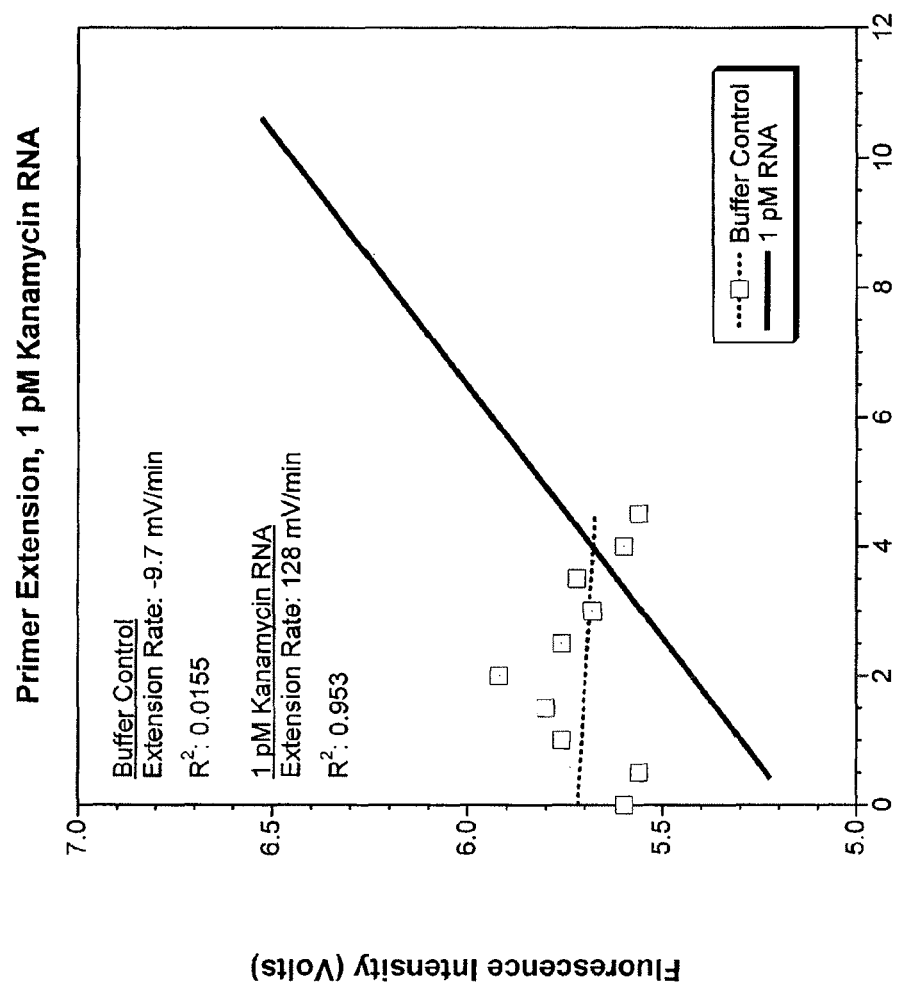
FIG. 20 is a plot of data for incorporation of Cy5.5-labeled cytosines into a DNA molecule during a primer extension reaction as detected using one embodiment of a detection system of the invention.

A primer extension experiment was conducted using an RNA standard (kanamycin control RNA) purchased from Promega, Inc. The capture oligonucleotide primer was complementary to a 24 base sequence near the 3' end of the RNA standard. This sequence is located 971 bases downstream from the 5' end of the RNA standard and contains 224 guanines. The cytosine deoxynucleotides were labeled with a fluorescent dye (Cy5.5). Roche's Transcriptor Reverse Transcriptase was used to extend the primer. The primer extension reaction was carried out at 48° C., which yielded reduced non-specific hybridization. Results from primer extension of 1 pM kanamycin RNA are shown in FIG. 20. The extension rate for the control is slightly negative (−9.7 mV/min), which is probably due to instrument noise. The extension rate of 1 pM kanamycin RNA is 128 mV/min, significantly higher than that of the control. Moreover, the signal increases linearly over the 10.5-minute reaction period with no sign of saturation. The initial signal level of the 1 pM RNA reaction was somewhat lower than that of the control run, and potentially due to a temperature difference (1-2° C.) between the two runs.

Example 4

Quantitative Real-Time PCR Detection of Transcripts

Quantitative real-time PCR detection of transcripts, for example, bcr/abl fusion transcripts, can be achieved using the detection system of the invention, using a PCR assay protocol modified from that described by Kreuzer et al. (supra). The system includes a substrate chip with excitation waveguides, collection waveguides and intersection regions. The intersection regions where the excitation waveguides and collection waveguides cross include optical sensing sites with sensing wells for conducting quantitative real-time PCR. The detection system further includes a scanning light source which is coupled to and in optical communication with the excitation waveguides of the substrate at some point along its scanning path. The system further includes an optical detector.

Samples suspected of containing RNA transcripts of interest (e.g., blood from a subject) are treated to obtain a source of total RNA which is subsequently reverse transcribed using reverse transcriptase into cDNA using techniques well known in the art. cDNA samples are delivered to sensing sites on the substrate of the system. As desired, suitable controls and different dilutions of a particular cDNA sample can be delivered to different sensing wells.

Reagents for real-time reverse transcriptase PCR are provided at the sensing sites. PCR reactions are conducted using primers/probes specific for one or more bcr/abl breakpoint cluster region. Such primers/probes are well known in the art (e.g., see Kreuzer et al. supra) and can be labeled with 6-carboxy-fluorescein phosphoramidite at the 5' end, and as a quencher, 5-carboxy-tetramethyl-rhodamine can be incorporated further along the primer/probe sequence. As the primer/probe is hydrolyzed through the 5'-nuecalse activity of Taq DNA polymerase, unquenched fluorescence from the fluorescein (reporter) dye can be induced. Phosphate groups are attached to primers/probes 3' end to prevent probe extension. A 10-ul PCR reaction mix contains 1 µl of 10×PCR buffer, 4.5 mM MgCl2, 0.8 mM dNTP, 0.5 µM each primer, 1 µM probe, 0.2 units of a temperature-release Taq DNA polymerase (Platinum® Pfx DNA Polymerase; Invitrogen, Corp.), and 20 ng of sample cDNA. PCR amplification is started with a 5-min denaturation step at 94° C., followed by 45 cycles of denaturation at 94° C. for 30 s and annealing/extension at 65° C. for 60 s.

While PCR amplification proceeds excitation light at a wavelength of about 658 nm is generated by the scanning light source and is directed to each sensing well by the excitation waveguides. If the cDNA samples include a transcript for bcr/abl fusion transcripts, annealing of primers/probes to the cDNA should occur. Subsequent hydrolysis of the probe by polymerase and unquenching of the fluorescein reporter results in fluorescence in the sensing well.

As the number of cycles increases, the amount of unquenched fluorescein increases in relation to the amount of bcr/abl fusion transcript cDNA in the reaction.

By way of the collection waveguides fluorescence in the sensing wells is detectable by the optical detector of the system. Thus, detection of bcr/abl fusion transcripts can be measured in real-time and based on appropriate controls and analysis the amount of bcr/abl fusion transcripts in a sample can be quantified.

Example 5

Detection of HIV Status of Multiple Subjects

Fluorescent immunoassay-based detection of HIV+ status of multiple subjects can be achieved using a detection system such as the example illustrated in FIG. 7A. The system includes a substrate chip with excitation waveguides, collection waveguides and intersection regions. The intersection regions where the excitation waveguides and collection waveguides cross include optical sensing sites with sensing wells for conducting fluorescent immunoassays. The detection system further includes a scanning light source which is coupled to and in optical communication with the substrate at some point along its scanning path and the excitation waveguides. The system further includes an optical detector.

A partially purified antigen, for example, inactivated HIV protein p29 antigen, is pre-coated onto the sensing wells of the optical sensing sites. Next, a number of subject serums which may contain antibodies to HIV p29 are delivered to separate sensing sites. It is also envisioned that samples from multiple patients are pooled and that each pool is delivered to separate sensing sites. If a subject is HIV+, then their serum may contain antibodies to HIV protein p29, and those antibodies will bind to the HIV p29 antigens on the sensing sites. After a washing step, anti-human immunoglobulin coupled to a fluorescent dye (fluorescein) is added to the sensing sites. This secondary antibody binds to human antibodies in the sensing sites (i.e., the anti-p29 antibodies). Next an excitation light at a wavelength of about 658 nm is generated by the scanning light source and is directed to each sensing well by the excitation waveguides. If the secondary antibody is present the coupled fluorescein will fluoresce in the presence of the excitation light in the well.

By way of the collection waveguides fluorescence in the sensing wells is detectable by the optical detector of the system. Signal received by the optical detectors can be interpreted to determine if a given subject, or a sample pooled from multiple subjects, has antibodies to HIV p29. Suitable controls can be used to validate the results of the assay. Thus, the presence or absence of HIV p29 can be measured in a sample and HIV+ or HIV(−) status of multiple subjects or pools can be determined.

Example 6

Two-Site Sandwich Immunoassays

A two-site sandwich immunoassay can be employed in assays using the detection system of the invention (e.g., the systems as illustrated in FIG. 7A-7E). Antibodies fulfill two different roles in such assays, in which an immobilized antibody captures the analyte, while a soluble, fluorescently labeled antibody detects or "traces" analyte binding. To prevent competitive binding, capture and tracer antibodies must bind to different sites on the analyte molecule. For large analytes with repetitive epitopes (e.g., viruses and bacteria), a single antibody (specific for the repetitive epitope) can usually be employed in both capture and tracer roles. Smaller analytes (e.g. proteins and polysaccharides) expressing multiple, unique epitopes require two different antibodies, each specific for a unique epitope.

Three two-site sandwich immunoassay tests are envisioned: 1) serial testing of optical sensing sites; 2) low complexity parallel testing of optical sensing sites; and 3) sensitivity testing. In the first of these, a small volume (1-5 µL) of sample (containing analyte and tracer antibody) is spotted directly at a optical sensing site containing capture antibody using a microliter pipette. Binding kinetics at the site are monitored over a 5-min period at room temperature. Translation of optical detection to excitation and collection waveguides in connection with a different optical sensing site is effected and the assay is repeated at the new site. It is envisioned that at least 10 optical sensing sites can be tested using this serial procedure. Such tests can demonstrate sensitivity and intra-assay precision of the system.

In the second form of testing, using a substrate of the system that includes a 10×10 array of excitation waveguides and collection waveguides (see e.g., FIG. 7A), a single excitation waveguide of the substrate is excited, while output signals are monitored from all 10 collection waveguides using a linear detector array. Equal volumes (e.g., 50 µL) of sample containing analyte and tracer antibody (e.g., 10 nM, final concentration) can be pre-mixed and then injected into a sample well of the optical sensing site that contains capture antibody. Binding kinetics are monitored simultaneously in 10 optical sensing sites over a 5-mM period at room temperature. This form of testing can demonstrate the parallel assay capabilities of the system, as well as providing more detailed information about intra-assay precision.

In the third form of testing, the sensitivity, precision and linearity of the device can be demonstrated by constructing a standard curve of average reaction rate versus analyte concentration. Device configuration is the same as described above for the second form of testing (i.e., 10 simultaneous assays). Analyte concentration is varied over at least a 100-fold range, e.g. 10 pM to 1 nM, though the exact range can be adjusted depending on the clinical concentration range of the analyte being examined. A separate substrate chip is used for each concentration to be tested. Six to eight concentrations are examined. Resulting standard curves are typically linear at low concentration, but saturate at higher concentrations.

The Herron lab has developed immunoassays for many different analytes including human cardiac troponin I (cTnI), chorionic gonadotrophin (hCG), creatine phosphokinase isoform MB (CKMB), myoglobin, ovalbumin (used by the military as a "simulant" for toxins such as ricin and SEB), ricin, Staphylococcal enterotoxin B (SEB). (See Herron, J. N. et al. (2003). Orientation and Activity of Immobilized Antibodies. In: Biopolymers at Interfaces, 2nd Edition (M. Malmsten, ed.), Surfactant Science Series, Vol. 110, Marcel Dekker, New York, pp. 115-163; and Herron, J. N. et al. (2005). Planar Waveguide Biosensors for Point-Of-Care Clinical and Molecular Diagnostics. In: Fluorescence Sensors and Biosensors (R. B. Thompson, Ed.), CRC Press Taylor & Francis Group, Boca Raton, Fla. pp. 283-332).

The ovalbumin assay of Herron can be used in the first and second immunoassays described above. Advantageously, reagents for this assay are relatively inexpensive and no special handling is required. Detection requirements for cTnI and SEB are the most stringent, and thus immunoassays specific for these analytes are useful for the sensitivity testing immunoassays. However, since the CDC, NIH, and USDA all list SEB as a select agent requiring special handling it may be preferable to use cTnI in sensitivity testing. cTnI can be paired with two other cardiac markers (CKMB and myoglobin) for simultaneous immunoassay sensitivity testing.

Figure 21:
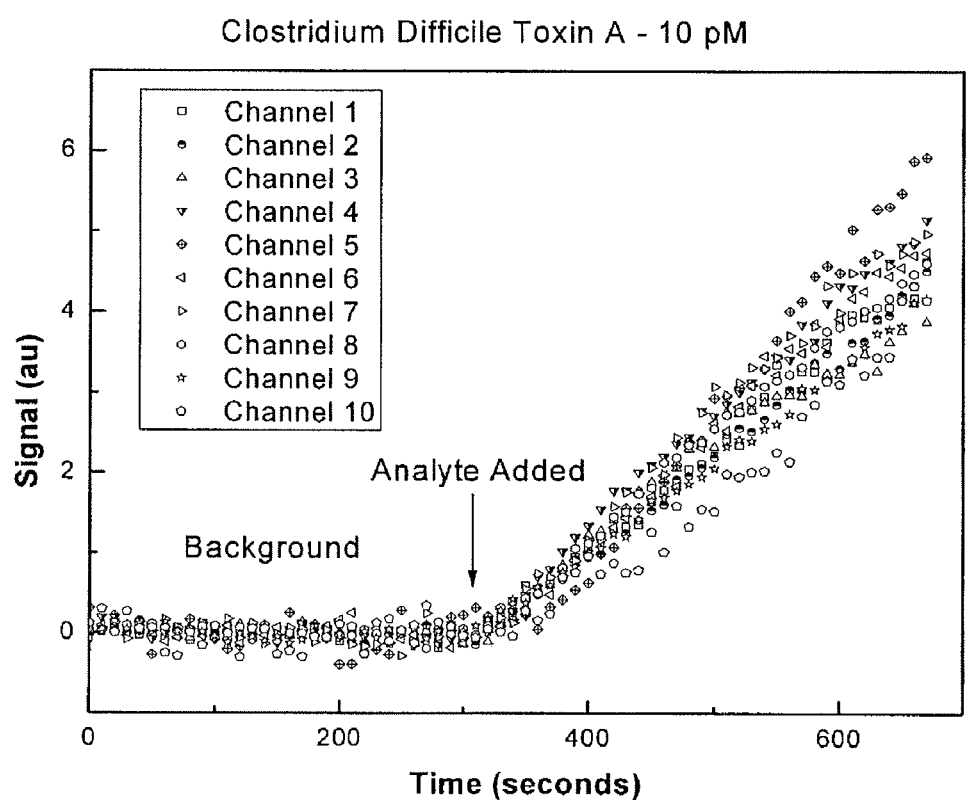
FIG. 21 is a graph showing a real-time detection of *Clostridium difficile* toxin A in bovine serum on a 10-channel chip using a detection system of the invention.

Detection of *Clostridium difficile* toxin A was used in the second and third immunoassays described above to demonstrate the rapidity and sensitivity of the detection system of the current invention. FIG. 21 depicts a real-time detection of *Clostridium difficile* toxin A in bovine serum on a 10-channel chip. In the first 5 minutes (300 seconds) no analyte is present and thus the signal is flat. After 5-minutes analyte is added to reach a concentration of 10 pM. As the analyte binds to the capture antibody immobilized to the chip surface, and a second labeled antibody binds to the complex in a sandwich assay format, the optical signal in all channels increases. The slope of the increasing signal is proportional to the analyte concentration.

Figure 22:
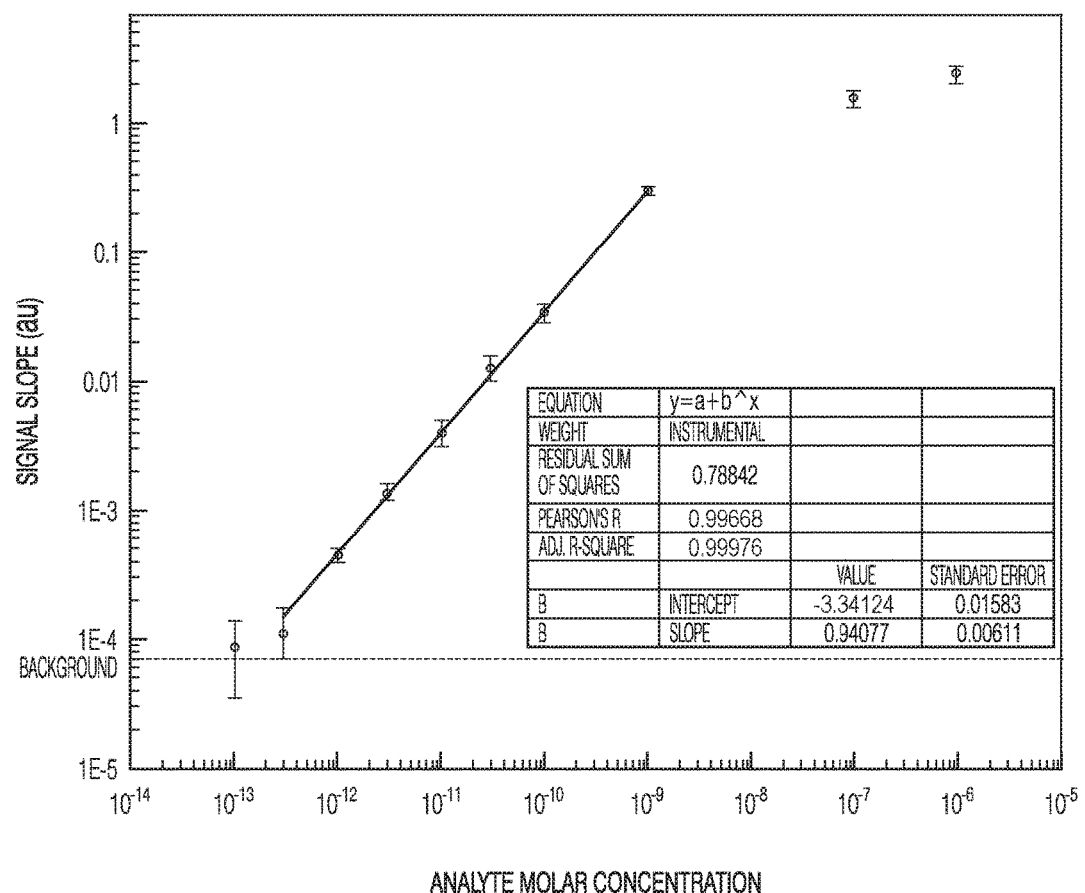
FIG. 22 is a graph showing a standard curve for *Clostridium difficile* toxin A as measured on a series of ten 10-channel chips using a detection system of the invention.

FIG. 22 shows a standard curve for *Clostridium difficile* toxin A as measured on a series of ten 10-channel chips. The optical signal slope increases as a function of the increasing concentration. Ten different concentrations were measured, starting from 0.1 pM and up to 1 µM. As can be seen, the slope concentration relation is linear between 0.3 pM and 1 nM. The limit of detection (LOD) is approximately 0.1 pM. These results demonstrate significant improvements in rapidity and sensitivity as compared to commercially available tests for *Clostridium difficile* toxin A, which have assay times ranging from 15 to 75 minutes and LODs ranging from 2.7 to 133 pM.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of measuring a concentration of an analyte using a waveguide chip, the method comprising:
   adding a known amount of one or more normalizing moieties to a sample;
   adding a first detection molecule labelled with a first fluorescent tag to the sample, the first detection molecule specific to the analyte;
   adding one or more secondary detection molecules, each secondary detection molecule labelled with a distinct secondary fluorescent tag, to the sample, the one or more secondary detection molecules specific to the one or more normalizing moieties, wherein the first fluorescent tag and the one or more secondary fluorescent tags emit at different fluorescence wavelengths;
   introducing the sample to an array of sensing sites on the waveguide chip, each sensing site of the array having a first capture molecule specific to the analyte and one or more secondary capture molecules specific to the one or more normalizing moieties, wherein the first capture molecule and the one or more secondary capture molecules are both immobilized in each sensing site of the array at a predetermined ratio;

introducing a first light pulse into one or more excitation waveguides on the waveguide chip at a first predetermined interval, the one or more excitation waveguides in optical communication with the array of sensing sites, the first light pulse configured to excite the first fluorescent tag;

introducing one or more secondary light pulses into the one or more excitation waveguides on the waveguide chip at one or more secondary predetermined intervals, wherein the first light pulse and the one or more secondary light pulses have different wavelengths, the one or more secondary light pulses configured to excite the one or more secondary fluorescent tags;

measuring the fluorescence emitted by the first detection molecule and the one or more secondary detection molecules through a plurality of collection waveguides in optical communication with the array of sensing sites; and normalizing the measured fluorescence emitted by the first detection molecule using the measured fluorescence emitted by the one or more secondary detection molecules.

2. The method of claim 1, wherein the step of normalizing the measured fluorescence emitted by the first detection molecule comprises dividing the measured fluorescence emitted by the first detection molecule by the measured fluorescence emitted by the one or more secondary detection molecules.

3. The method of claim 1, wherein the first detection molecule, the one or more secondary detection molecules, the first capture molecule, and the one or more secondary capture molecules are antibodies.

4. The method of claim 1, wherein the step of normalizing the measured fluorescence emitted by the first detection molecule further comprises generating one or more calibration curves from the measured fluorescence emitted by the one or more secondary detection molecules.

5. The method of claim 1, wherein the one or more normalizing moieties comprises at least a first normalizing moiety and a second normalizing moiety, wherein the amount of the first normalizing moiety added to the sample is greater than the amount of the second normalizing moiety added to the sample.

6. The method of claim 1, wherein the step of normalizing the measured fluorescence emitted by the first detection molecule comprises dividing the measured fluorescence emitted by the first detection molecule by a slope of the measured fluorescence emitted by the one or more secondary detection molecules.

7. The method of claim 1, wherein the step of normalizing the measured fluorescence emitted by the first detection molecule comprises dividing a slope of the measured fluorescence emitted by the first detection molecule by a slope of the measured fluorescence emitted by the one or more secondary detection molecules.

\* \* \* \* \*